(12) United States Patent
Holson et al.

(10) Patent No.: US 10,793,538 B2
(45) Date of Patent: Oct. 6, 2020

(54) CYCLOALKENYL HYDROXAMIC ACID DERIVATIVES AND THEIR USE AS HISTONE DEACETYLASE INHIBITORS

(71) Applicant: The Broad Institute, Inc., Cambridge, MA (US)

(72) Inventors: Edward Holson, Newton, MA (US); Fanny Lazzaro, Cambridge, MA (US); David Olson, Boston, MA (US); Florence Fevrier Wagner, Ashland, MA (US); Michel Weiwer, Cambridge, MA (US)

(73) Assignee: The Broad Institute, Inc., Cambridge, MA (US)

( * ) Notice: Subject to any disclaimer, the term of this patent is extended or adjusted under 35 U.S.C. 154(b) by 0 days.

(21) Appl. No.: 15/878,694

(22) Filed: Jan. 24, 2018

(65) Prior Publication Data

US 2018/0215726 A1    Aug. 2, 2018

Related U.S. Application Data

(63) Continuation of application No. 14/654,296, filed as application No. PCT/US2013/076618 on Dec. 19, 2013, now Pat. No. 9,914,717.

(60) Provisional application No. 61/739,967, filed on Dec. 20, 2012.

(51) Int. Cl.
| | |
|---|---|
| C07D 309/28 | (2006.01) |
| C07C 259/08 | (2006.01) |
| C07C 323/61 | (2006.01) |
| C07D 209/08 | (2006.01) |
| C07D 211/78 | (2006.01) |
| C07D 211/96 | (2006.01) |
| C07D 263/16 | (2006.01) |

(52) U.S. Cl.
CPC .......... *C07D 309/28* (2013.01); *C07C 259/08* (2013.01); *C07C 323/61* (2013.01); *C07D 209/08* (2013.01); *C07D 211/78* (2013.01); *C07D 211/96* (2013.01); *C07D 263/16* (2013.01); *C07C 2601/10* (2017.05); *C07C 2601/16* (2017.05); *C07C 2602/08* (2017.05); *C07C 2602/10* (2017.05)

(58) Field of Classification Search
CPC .. C07D 309/28; C07D 209/08; C07D 211/78; C07D 211/96; C07D 263/16; C07C 259/08; C07C 323/61
USPC ........................................................ 514/355
See application file for complete search history.

(56) References Cited

U.S. PATENT DOCUMENTS

| | | |
|---|---|---|
| 3,689,550 A | 9/1972 | Schellenbaum et al. |
| 3,850,931 A | 11/1974 | Kim et al. |
| 4,404,356 A | 9/1983 | Andrews |
| 5,135,949 A | 8/1992 | von der Saal et al. |
| 5,137,918 A | 8/1992 | Weiershausen et al. |
| 5,284,656 A | 2/1994 | Platz et al. |
| 5,451,569 A | 9/1995 | Wong et al. |
| 5,525,727 A | 6/1996 | Bodor |
| 5,618,803 A | 4/1997 | Bodor |
| 5,635,503 A | 6/1997 | Poindexter et al. |
| 5,783,522 A | 7/1998 | Schaefer et al. |
| 5,886,044 A | 3/1999 | Widdowson et al. |
| 6,313,122 B1 | 11/2001 | Beight et al. |
| 6,407,137 B2 | 6/2002 | Shashoua |
| 6,645,990 B2 | 11/2003 | Askew et al. |
| 6,653,309 B1 | 11/2003 | Saunders et al. |
| 6,946,462 B2 | 9/2005 | Haag et al. |
| 7,119,074 B2 | 10/2006 | Ekwuribe et al. |
| 7,550,490 B2 | 6/2009 | Lu et al. |
| 8,138,168 B1 | 3/2012 | Jones |
| 8,158,825 B2 | 4/2012 | Grimm et al. |
| 8,211,901 B2 | 7/2012 | Lu et al. |
| 8,450,525 B2 | 5/2013 | Rajagopal et al. |
| 8,598,168 B2 | 12/2013 | Moradei et al. |
| 8,957,066 B2 | 2/2015 | Jacques et al. |
| 9,265,734 B2 | 2/2016 | Rusche et al. |
| 9,365,498 B2 | 6/2016 | Holson et al. |
| 9,447,030 B2 | 9/2016 | Holson et al. |

(Continued)

FOREIGN PATENT DOCUMENTS

| | | |
|---|---|---|
| BE | 891537 | 4/1982 |
| DE | 670 584 C | 1/1939 |

(Continued)

OTHER PUBLICATIONS

Capkova et al., Bioorganic & Medicinal Chemistry Letters, 2007, 17(23), 6463-6466 (Year: 2007)*

(Continued)

*Primary Examiner* — Yevgeny Valenrod
(74) *Attorney, Agent, or Firm* — Wolf, Greenfield & Sacks, P.C.

(57) ABSTRACT

The present invention provides compounds of formula (I):

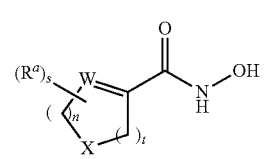

(I)

or a pharmaceutically acceptable salt, solvate, or prodrug thereof, wherein W, X, n, s, t, and $R^a$ are as described herein. The present invention relates generally to selective inhibitors of histone deacetylase and to methods of making and using them.

20 Claims, 1 Drawing Sheet

(56) References Cited

U.S. PATENT DOCUMENTS

| | | |
|---|---|---|
| 9,790,184 B2 | 10/2017 | Holson et al. |
| 9,890,172 B2 | 2/2018 | Holson et al. |
| 9,914,717 B2 | 3/2018 | Holson et al. |
| 9,988,343 B2 | 6/2018 | Mazitschek et al. |
| 2002/0173507 A1 | 11/2002 | Santora et al. |
| 2002/0193367 A1 | 12/2002 | Adam et al. |
| 2003/0027862 A1 | 2/2003 | Haning et al. |
| 2003/0159221 A1 | 8/2003 | Lang |
| 2003/0166639 A1 | 9/2003 | Adam et al. |
| 2006/0008517 A1 | 1/2006 | Lynch et al. |
| 2007/0054904 A1 | 3/2007 | Knolle et al. |
| 2008/0070954 A1 | 3/2008 | Lim et al. |
| 2008/0132503 A1 | 6/2008 | Moradei et al. |
| 2009/0118303 A1 | 5/2009 | Jikyo et al. |
| 2010/0009990 A1 | 1/2010 | Venkataramani et al. |
| 2010/0029615 A1 | 2/2010 | Munchhof et al. |
| 2010/0144732 A1 | 6/2010 | Krueger et al. |
| 2010/0216806 A1 | 8/2010 | Liang et al. |
| 2010/0298358 A1 | 11/2010 | Lu et al. |
| 2010/0324046 A1 | 12/2010 | Harrington et al. |
| 2014/0080800 A1 | 3/2014 | Holson et al. |
| 2014/0080802 A1 | 3/2014 | Holson et al. |
| 2014/0335550 A1 | 11/2014 | Zhang et al. |
| 2015/0191427 A1 | 7/2015 | Holson et al. |
| 2015/0368221 A1 | 12/2015 | Holson et al. |
| 2016/0251351 A1 | 9/2016 | Holson et al. |
| 2016/0272579 A1 | 9/2016 | Mazitschek et al. |
| 2016/0347761 A1 | 12/2016 | Holson et al. |
| 2018/0016282 A9 | 1/2018 | Holson et al. |
| 2018/0072671 A1 | 3/2018 | Holson et al. |
| 2018/0099977 A1 | 4/2018 | Holson et al. |

FOREIGN PATENT DOCUMENTS

| | | |
|---|---|---|
| DE | 1108213 | 6/1961 |
| DE | 2163381 | 7/1972 |
| EP | 0 196 005 A1 | 10/1986 |
| EP | 0 199 393 A1 | 10/1986 |
| EP | 0 309 423 | 3/1989 |
| EP | 1 402 888 A1 | 3/2004 |
| GB | 2 086 905 A | 5/1982 |
| JP | 3-232868 A | 10/1991 |
| JP | H06-122669 A | 5/1994 |
| JP | 9-503748 A | 4/1997 |
| JP | 9-227495 A | 9/1997 |
| JP | 2000-302765 | 10/2000 |
| JP | 2004-521072 A | 7/2004 |
| JP | 2005-508311 A | 3/2005 |
| JP | 2005-522440 A | 7/2005 |
| JP | 2007-506785 | 3/2007 |
| JP | 2008-502719 | 1/2008 |
| JP | 2008-509075 A | 3/2008 |
| JP | 2008-094847 A | 4/2008 |
| JP | 2009-523726 A | 6/2009 |
| JP | 2009-536615 A | 10/2009 |
| JP | 2010-531359 A | 9/2010 |
| JP | 2011-528039 | 11/2011 |
| JP | 2012-510512 A | 5/2012 |
| JP | 2012-518612 A | 8/2012 |
| WO | WO 01/70675 | 9/2001 |
| WO | WO 2002/14311 A2 | 2/2002 |
| WO | WO 02/46181 A2 | 6/2002 |
| WO | WO 03/013484 | 2/2003 |
| WO | WO 2003/066623 A1 | 8/2003 |
| WO | WO 2004/073599 A2 | 9/2004 |
| WO | WO 2005/025557 | 3/2005 |
| WO | WO 2005/030705 A1 | 4/2005 |
| WO | WO 2005/034880 A2 | 4/2005 |
| WO | WO 2005/066151 A2 | 7/2005 |
| WO | WO 2006/001958 | 1/2006 |
| WO | WO 2006/016680 A1 | 2/2006 |
| WO | WO 2007/087130 A2 | 8/2007 |
| WO | WO 2007/118137 A1 | 10/2007 |
| WO | WO 2008/113255 | 9/2008 |
| WO | WO 2009/002534 A1 | 12/2008 |
| WO | WO 2009/055917 A1 | 5/2009 |
| WO | WO 2009/076234 A2 | 6/2009 |
| WO | WO 2009/104819 A1 | 8/2009 |
| WO | WO 2010/014054 A1 | 2/2010 |
| WO | WO 2010/028192 | 3/2010 |
| WO | WO 2010/065117 A1 | 6/2010 |
| WO | WO 2010/094678 A1 | 8/2010 |
| WO | WO 2010/142426 A1 | 12/2010 |
| WO | WO 2011/009084 A2 | 1/2011 |
| WO | WO 2011/053876 | 5/2011 |
| WO | WO 2012/112447 A2 | 8/2012 |
| WO | WO 2012/118782 A1 | 9/2012 |
| WO | WO 2012/149540 | 11/2012 |
| WO | WO 2012/155806 A1 | 11/2012 |
| WO | WO 2013/059582 A2 | 4/2013 |
| WO | WO 2013/067391 A1 | 5/2013 |
| WO | WO 2015/134973 A1 | 9/2015 |

OTHER PUBLICATIONS

CAplus abstract of Bredt et al J. Chem Soc 1914, 103, 2182-2225 (Year: 1914).*

Canadian Office Action dated Apr. 17, 2018 for Application No. 2,834,548.

Canadian Office Action dated Nov. 19, 2018 for Application No. 2,834,548.

European Communication dated Jul. 17, 2018 Application No. 13194971.1.

[No Author Listed] Chemical Abstracts STN Database Record for RN 1153257-67-0. Jun. 7, 2009. 1 page.

[No Author Listed] Chemical Abstracts STN Database Record for RN 737809-68-6 Sep. 2, 2004. 1 page.

[No Author Listed] Chemical Abstracts STN Database Record for RN 11812848-11-2. Sep. 8, 2009. 1 page.

[No Author Listed] Chemical Abstracts STN Database Record for RN 1218208-54-8. Apr. 11, 2010. 1 page.

[No Author Listed] Chemical Abstracts STN Database Record for RN 926231-00-7. Mar. 13, 2007. 1 page.

[No Author Listed] Chemical Abstracts STN Database Record for RN 926250-54-6. Mar. 13, 2007. 1 page.

[No Author Listed] Chemical Abstracts STN Database Record for RN 695166-87-1. Jun. 18, 2004. 1 page.

[No Author Listed] Chemical Abstracts STN Database Record for RN 926217-21-2. Mar. 13, 2007. 1 page.

El-Sayed, Bulletin of the Chemical Society of Japan. 1979(52)3092-3095.

Supplementary European Search Report dated Apr. 13, 2015 for Application No. EP 12775936.3.

Office Communication dated May 30, 2016 for Application No. EP 12775936.3.

European Search Report dated Mar. 4, 2014 for Application No. EP 13194971.1.

Office Communication dated Jul. 15, 2015 for Application No. EP 13194971.1.

European Communication Pursuant to Article 94(3) EPC dated Nov. 20, 2017 for Application No. 13194971.1.

Japanese Office Action dated Oct. 14, 2015 for Application No. JP 2014-508179.

International Search Report and Written Opinion dated Jul. 20, 2012 for Application No. PCT/US2012/035814.

International Preliminary Report on Patentability dated Nov. 7, 2013 for Application No. PCT/US2012/035814.

European Office Communication for European Application No. 13745773.5 dated Dec. 21, 2016.

International Search Report and Written Opinion dated Oct. 22, 2013 for Application No. PCT/US2013/052572.

International Preliminary Report on Patentability dated Feb. 5, 2015 for Application No. PCT/US2013/052572.

European Communication Pursuant to Article 94(3) EPC dated Mar. 27, 2018 with Office Action Annex for Application No. 13745773.5.

International Search Report and Written Opinion dated Mar. 13, 2014 for Application No. PCT/US2013/076618.

(56) References Cited

OTHER PUBLICATIONS

International Preliminary Report on Patentability dated Jul. 2, 2015 for Application No. PCT/US2013/076618.
[No Author Listed], Database Accession No. 341032-95-9. Database Registry Chemical Abstracts Service. Jun. 14, 2001. STN File CASREACT: XP002720214. 2 pages.
Abramson et al., Blocking the effects of IL-1 in rheumatoid arthritis protects bone and cartilage. Rheumatology (Oxford). Sep. 2002;41(9):972-80. Review.
Abuchowski et al., Soluble Polymer-Enzyme Adducts. In: Enzymes as Drugs. 1981. Hocenberg et al., Eds. 367-83.
Acharya et al., Rational development of histone deacetylase inhibitors as anticancer agents: a review. Mol Pharmacol. Oct. 2005;68(4):917-32. Epub Jun. 14, 2005. Review.
Adjei et al., Bioavailability of leuprolide following intratracheal administration to beagle dogs. Int J Pharm. Jun. 11, 1990;61:135-44.
Adjei et al., Pulmonary delivery of peptide drugs: effect of particle size on bioavailability of leuprolide acetate in healthy male volunteers. Pharm Res. Jun. 1990;7(6):565-9.
Alberini, Transcription factors in long-term memory and synaptic plasticity. Physiol Rev. Jan. 2009;89(1):121-45. doi: 10.1152/physrev.00017.2008. Review.
Alenghat et al., Nuclear receptor corepressor and histone deacetylase 3 govern circadian metabolic physiology. Nature. Dec. 18, 2008;456(7224):997-1000. doi: 10.1038/nature07541. Epub Nov. 26, 2008.
Arts et al., Histone deacetylase inhibitors: from chromatin remodeling to experimental cancer therapeutics. Curr Med Chem. Nov. 2003;10(22):2343-50. Review.
Banker et al., Modern Pharmaceutics, 3rd ed. Marcel Dekker. 1996;451, 596.
Bannister et al., Regulation of chromatin by histone modifications. Cell Res. Mar. 2011;21(3):381-95. doi: 10.1038/cr.2011.22. Epub Feb. 15, 2011. Review.
Bantscheff et al., Chemoproteomics profiling of HDAC inhibitors reveals selective targeting of HDAC complexes. Nat Biotechnol. Mar. 2011;29(3):255-65. doi: 10.1038/nbt.1759. Epub Jan. 23, 2011.
Barrett et al., Beyond transcription factors: the role of chromatin modifying enzymes in regulating transcription required for memory. Learn Mem. Jun. 26, 2008;15(7):460-7. doi: 10.1101/lm.917508. Print Jul. 2008. Review.
Berge et al., Pharmaceutical salts. J Pharm Sci. Jan. 1977;66(1):1-19.
Blanchard et al., Histone deacetylase inhibitors: new drugs for the treatment of inflammatory diseases? Drug Discov Today. Feb. 1, 2005;10(3):197-204. Review.
Bradner et al., Chemical genetic strategy identifies histone deacetylase 1 (HDAC1) and HDAC2 as therapeutic targets in sickle cell disease. Proc Natl Acad Sci U S A. Jul. 13, 2010;107(28):12617-22. doi: 10.1073/pnas.1006774107. Epub Jun. 28, 2010.
Bradner et al., Chemical phylogenetics of histone deacetylases. Nat Chem Biol. Mar. 2010;6(3):238-243. Epub Sep. 1, 2010. 14 pages.
Braquet et al., Effect of endothelin-1 on blood pressure and bronchopulmonary system of the guinea pig. J Cardiovasc Pharmacol. 1989;13 Suppl 5:S143-6.
Bredt et al., 1-Epicamphor (1-β-camphor). Chemical Abstracts STN Database Record for RN 1914:9447. Oxford and Manchester. J. Chem. Soc. 1914;103:2182-25. Abstract Only.
Bredt et al., 1-Epicamphor (1-β-camphor). J Chem Soc Trans. 1913;103:2182-225.
Broide et al., Distribution of histone deacetylases 1-11 in the rat brain. J Mol Neurosci. 2007;31(1):47-58.
Brukshtus et al., Synthesis of N-acetyl derivatives of 5-and 6-ethoxy-2-methylthiobenzimidazole and their cardiotonic activity. Chem Heterocyclic Compounds. Jun. 1, 1997;33(6):665-71.
Bunn, Pathogenesis and treatment of sickle cell disease. N Engl J Med. Sep. 11, 1997;337(11):762-9. Review.
Burger et al., Is IL-1 a good therapeutic target in the treatment of arthritis? Best Pract Res Clin Rheumatol. Oct. 2006;20(5):879-96. Review.
Cargin et al., Mild memory impairment in healthy older adults is distinct from normal aging. Brain Cogn. 2006;60(2):146-55.
Chang et al., Differential response of cancer cells to HDAC inhibitors trichostatin A and depsipeptide. Br J Cancer. Jan. 3, 2012;106(1):116-25. doi: 10.1038/bjc.2011.532. Epub Dec. 8, 2011.
Chang et al., Synthesis and bioevaluation of novel 3,4,5-trimethoxybenzylbenzimidazole derivatives that inhibit Helicobacter pylori-induced pathogenesis in human gastric epithelial cells. European Journal of Medicinal Chemistry. Feb. 2012;48:244-54.
Charache et al., Effect of hydroxyurea on the frequency of painful crises in sickle cell anemia. Investigators of the Multicenter Study of Hydroxyurea in Sickle Cell Anemia. N Engl J Med. May 18, 1995;332(20):1317-22.
Chemical Abstracts STN Database Record for RN 1019377-02-6. May 6, 2008. 1 page.
Chemical Abstracts STN Database Record for RN 1038237-56-7. Aug. 3, 2008. 1 page.
Chemical Abstracts STN Database Record for RN 1095240-42-8. Jan. 22, 2009. 1 page.
Chemical Abstracts STN Database Record for RN 1152996-49-0. Jun. 7, 2009. 1 page.
Chemical Abstracts STN Database Record for RN 1153085-77-8. Jun. 7, 2009. 1 page.
Chemical Abstracts STN Database Record for RN 1154691-98-1. Jun. 9, 2009. 1 page.
Chemical Abstracts STN Database Record for RN 1156303-71-7. Jun. 12, 2009. 1 page.
Chemical Abstracts STN Database Record for RN 1182778-35-3. Sep. 11, 2009. 1 page.
Chemical Abstracts STN Database Record for RN 1262320-49-9. Feb. 8, 2011. 1 page.
Chemical Abstracts STN Database Record for RN 128691-95-2. Aug. 10, 1990. 1 page.
Chemical Abstracts STN Database Record for RN 1350126-66-7. Dec. 7, 2011. 1 page.
Chemical Abstracts STN Database Record for RN 157026-22-7. Aug. 16, 1994. 1 page.
Chemical Abstracts STN Database Record for RN 169604-52-8. Nov. 3, 1995. 1 page.
Chemical Abstracts STN Database Record for RN 22380-13-8. Nov. 16, 1984. 1 page.
Chemical Abstracts STN Database Record for RN 76280-05-2. Nov. 16, 1984. 1 page.
Chemical Abstracts STN Database Record for RN 865837-30-5. Oct. 24, 2005. 1 page.
Chemical Abstracts STN Database Record for RN 926186-52-9. Mar. 13, 2007.
Chemical Abstracts STN Database Record for RN 926189-39-1. Mar. 13, 2007.
Chemical Abstracts STN Database Record for RN 926194-42-5. Mar. 13, 2007. 1 page.
Chemical Abstracts STN Database Record for RN 926196-62-5. Mar. 13, 2007. 1 page.
Chemical Abstracts STN Database Record for RN 926204-50-4. Mar. 13, 2007.
Chemical Abstracts STN Database Record for RN 926206-09-9. Mar. 13, 2007. 1 page.
Chemical Abstracts STN Database Record for RN 926214-21-3. Mar. 13, 2007.
Chemical Abstracts STN Database Record for RN 926217-10-9. Mar. 13, 2007. 1 page.
Chemical Abstracts STN Database Record for RN 926219-65-0. Mar. 13, 2007.
Chemical Abstracts STN Database Record for RN 926219-90-1. Mar. 13, 2007. 1 page.
Chemical Abstracts STN Database Record for RN 926233-05-8. Mar. 13, 2007. 1 page.
Chemical Abstracts STN Database Record for RN 926246-05-1. Mar. 13, 2007. 1 page.

(56) References Cited

OTHER PUBLICATIONS

Chemical Abstracts STN Database Record for RN 926247-11-2. Mar. 13, 2007.
Chemical Abstracts STN Database Record for RN 926260-48-2. Mar. 13, 2007.
Chemical Abstracts STN Database Record for RN 926260-89-1. Mar. 13, 2007.
Chemical Abstracts STN Database Record for RN 926264-98-4. Mar. 13, 2007. 1 page.
Chemical Abstracts STN Database Record for RN 926272-49-3. Mar. 13, 2007.
Chemical Abstracts STN Database Record for RN 937607-77-7. Jun. 17, 2007. 1 page.
Chemical Abstracts STN Database Record for RN 937619-64-2. Jun. 17, 2007. 1 page.
Chemical Abstracts STN Database Record for RN 937624-40-3. Jun. 17, 2007. 1 page.
Chemical Abstracts STN Database Record for RN 953731-76-5 Nov. 15, 2007. 1 page.
Chemical Abstracts STN Database Record for RN 953741-80-5. Nov. 15, 2007. 1 page.
Chemical Abstracts STN Database Record for RN 953747-99-4. Nov. 15, 2007. 1 page.
Chou et al., Pimelic diphenylamide 106 is a slow, tight-binding inhibitor of class I histone deacetylases. J Biol Chem. Dec. 19, 2008;283(51):35402-9. doi: 10.1074/jbc.M807045200.
Citrome, Schizophrenia and valproate. Psychopharmacol Bull. 2003;37 Suppl 2:74-88. Review.
Conti et al., Design and synthesis of novel isoxazole-based HDAC inhibitors. Eur J Med Chem. Sep. 2010;45(9):4331-8. doi: 10.1016/j.ejmech.2010.06.035. Epub Jun. 30, 2010.
Dayer et al., Anti-interleukin-1 therapy in rheumatic diseases. Curr Opin Rheumatol. May 2001;13(3):170-6. Review.
Debs et al., Lung-specific delivery of cytokines induces sustained pulmonary and systemic immunomodulation in rats. J Immunol. May 15, 1988;140(10):3482-8.
Dehaene et al., Reward-dependent learning in neuronal networks for planning and decision making. Brain Res. 2000;126:217-29.
Diao et al., Assembly of substituted 1H-benzimidazoles and 1,3-dihydrobenzimidazol-2-ones via CuI/L-proline catalyzed coupling of aqueous ammonia with 2-iodoacetanilides and 2-iodophenylcarbamates. J Org Chem. Oct. 16, 2009;74(20):7974-7. doi: 10.1021/jo9017183.
Dörwald, Chapter 1: Organic Synthesis: General Remarks. Side Reactions in Organic Synthesis. A Guide to Successful Synthesis Design. Wiley-VCH Verlag GmbH & Co. KGaA. 2005. 32 pages.
D'Ydewalle et al., Charcot-Marie-Tooth disease: emerging mechanisms and therapies. Int J Biochem Cell Biol. Aug. 2012;44(8):1299-304. doi: 10.1016/j.biocel.2012.04.020. Epub Apr. 30, 2012. Review.
D'Ydewalle et al., HDAC6 at the Intersection of Neuroprotection and Neurodegeneration. Traffic. Jun. 2012;13(6):771-9. doi: 10.1111/j.1600-0854.2012.01347.x. Epub Mar. 26, 2012. Review.
Fischer et al., Cyclin-dependent kinase 5 is required for associative learning. J Neurosci. May 1, 2002;22(9):3700-7.
Fischer et al., Recovery of learning and memory is associated with chromatin remodelling. Nature. May 10, 2007;447(7141):178-82. Epub Apr. 29, 2007.
Fischle et al., Enzymatic activity associated with class II HDACs is dependent on a multiprotein complex containing HDAC3 and SMRT/N-CoR. Mol Cell. Jan. 2002;9(1):45-57.
Foster, Deuterium Isotope Effects in the Metabolism of Drugs and Xenobiotics: Implications for Drug Design. Adv Drug Res. 1985;14:1-40.
Fray et al., CANTAB battery: proposed utility in neurotoxicology. Neurotoxicol Teratol. Jul.-Aug. 1996;18(4):499-504. Review.
Glaser et al., Differential protein acetylation induced by novel histone deacetylase inhibitors. Biochem Biophys Res Commun. Dec. 17, 2004;325(3):683-90.
Govindarajan et al., Reducing HDAC6 ameliorates cognitive deficits in a mouse model for Alzheimer's disease. EMBO Mol Med. Jan. 2013;5(1):52-63. Doi: 10.1002/emmm.201201923. Epub Nov. 26, 2012.
Grundmann et al., Nitrile Oxides. XII. Cycloaliphatic and Aliphatic Stable Nitrile Oxides. J Org Chem. Jan. 1, 1969;34(6):2016-8.
Guan et al., HDAC2 negatively regulates memory formation and synaptic plasticity. Nature. May 7, 2009;459(7243):55-60. doi: 10.1038/nature07925.
Guenther et al., A core SMRT corepressor complex containing HDAC3 and TBL1, a WD40-repeat protein linked to deafness. Genes Dev. May 1, 2000;14(9):1048-57.
Hancock et al., HDAC inhibitor therapy in autoimmunity and transplantation. Ann Rheum Dis. Apr. 2012;71 Suppl 2:i46-54. doi: 10.1136/annrheumdis-2011-200593. Review.
Hnilicová et al., Histone deacetylase activity modulates alternative splicing. PloS One. Feb. 2, 2011;6(2):e16727. Doi: 10.1371/journal.pone.0016727. 11 pages.
Hubbard et al., Anti-neutrophil-elastase defenses of the lower respiratory tract in alpha 1-antitrypsin deficiency directly augmented with an aerosol of alpha 1-antitrypsin. Ann Intern Med. Aug. 1, 1989;111(3):206-12.
Iverson, Interpreting change on the WAIS-III/WMS-III in clinical samples. Arch Clin Neuropsychol. Feb. 2001;16(2):183-91.
Jochems et al., Antidepressant-like properties of novel HDAC6-selective inhibitors with improved brain bioavailability. Neuropsychopharmacology. Jan. 2014;39(2):389-400. doi: 10.1038/npp.2013.207. Epub Aug. 19, 2013.
Johannessen et al., Valproate: past, present, and future. CNS Drug Rev. 2003 Summer;9(2):199-216. Review.
Kalin et al., Development and therapeutic implications of selective histone deacetylase 6 inhibitors. J Med Chem. Aug. 22, 2013;56(16):6297-313. doi: 10.1021/jm4001659. Epub May 15, 2013. Review.
Karagianni et al., HDAC3: taking the SMRT-N-CoRrect road to repression. Oncogene. Aug. 13, 2007;26(37):5439-49. Review.
Katragadda et al., Hydrophobic effect and hydrogen bonds account for the improved activity of a complement inhibitor, compstatin. J Med Chem. Jul. 27, 2006;49(15):4616-22.
Katsura et al., Studies on antiulcer drugs. II. Synthesis and antiulcer activities of imidazo[1,2-alpha]pyridinyl-2-alkylaminobenzoxazoles and 5,6,7,8-tetrahydroimidazo[1,2-alpha]pyridinyl derivatives. Chem Pharm Bull (Tokyo). Feb. 1992;40(2):371-80.
Kilgore et al., Inhibitors of class 1 histone deacetylases reverse contextual memory deficits in a mouse model of Alzheimer's disease. Neuropsychopharmacology. Mar. 2010;35(4):870-80. doi:10.1038/npp.2009.197. Epub Dec. 9, 2009.
Kouzarides, Chromatin modifications and their function. Cell. Feb. 23, 2007;128(4):693-705. Review.
Kreutzberger et al., Antiinflammatory Agents, VII: Aroylation of 5-Chlorobenzotriazole [Published in German as Entzündungshemmende Wirkstoffe, 7. Mitt. Aroylierung von 5-Chlorbenzotriazol]. Arch. Pharm. 1980;313(3): 255-259. doi: 10.1002/ardp.19803130311.
Kuhn et al., Stalling of spliceosome assembly at distinct stages by small-molecule inhibitors of protein acetylation and deacetylation. RNA. Jan. 2009;15(1):153-75. doi: 10.1261/rna.1332609. Epub Nov. 24, 2008.
Lane et al., Histone deacetylase inhibitors in cancer therapy. J Clin Oncol. Nov. 10, 2009;27(32):5459-68. doi: 10.1200/JCO.2009.22.1291. Epub Oct. 13, 2009.
Langer, New methods of drug delivery. Science. Sep. 28, 1990;249(4976):1527-33. Review.
Langley et al., Remodeling chromatin and stress resistance in the central nervous system: histone deacetylase inhibitors as novel and broadly effective neuroprotective agents. Curr Drug Targets CNS Neurol Disord. Feb. 2005;4(1):41-50. Review.
Lattal et al., Systemic or intrahippocampal delivery of histone deacetylase inhibitors facilitates fear extinction. Behav Neurosci. Oct. 2007;121(5):1125-31.

(56) References Cited

OTHER PUBLICATIONS

Leoni et al., The antitumor histone deacetylase inhibitor suberoylanilide hydroxamic acid exhibits antiinflammatory properties via suppression of cytokines. Proc Natl Acad Sci U S A. Mar. 5, 2002;99(5):2995-3000. Epub Feb. 26, 2002.

Lettre et al., DNA polymorphisms at the BCL11A, HBS1L-MYB, and beta-globin loci associate with fetal hemoglobin levels and pain crises in sickle cell disease. Proc Natl Acad Sci U S A. 2008;105(33):11869-74. doi: 10.1073/pnas.0804799105. Epub Jul. 30, 2008.

Letvin et al., Augmentation of fetal-hemoglobin production in anemic monkeys by hydroxyurea. N Engl J Med. Apr. 5, 1984;310(14):869-73.

Levenson et al., Regulation of histone acetylation during memory formation in the hippocampus. J Biol Chem. Sep. 24, 2004;279(39):40545-59. Epub Jul. 23, 2004.

Li et al., Both corepressor proteins SMRT and N-CoR exist in large protein complexes containing HDAC3. EMBO J. Aug. 15, 2000;19(16):4342-50.

Locock et al., γ-aminobutyric acid(C) ($GABA_C$) selective antagonists derived from the bioisosteric modification of 4-aminocyclopent-1-enecarboxylic acid: amides and hydroxamates. J Med Chem. Jul. 11, 2013;56(13):5626-30. doi: 10.1021/jm4006548. Epub Jun. 27, 2013.

Malvaez et al., Modulation of chromatin modification facilitates extinction of cocaine-induced conditioned place preference. Biol Psychiatry. Jan. 1, 2010;67(1):36-43. doi: 10.1016/j.biopsych.2009.07.032. Epub.

Marks et al., Histone deacetylase inhibitors. Adv Cancer Res. 2004;91:137-68. Review.

Marks et al., Histone deacetylases and cancer: causes and therapies. Nat Rev Cancer. Dec. 2001;1(3):194-202. Review.

Matsushita et al., Smart cleavage reactions: the synthesis of benzimidazoles and benzothiazoles from polymer-bound esters. Tetrahedron Lett. 2004;45(2):313-6.

McKay et al., A bird's-eye view of post-translational modifications in the spliceosome and their roles in spliceosome dynamics. Mol Biosyst. Nov. 2010;6(11):2093-102. doi: 10.1039/c002828b. Epub Jun. 22, 2014. 20 pages.

McQuown et al., HDAC3 is a critical negative regulator of long-term memory formation. J Neurosci. Jan. 12, 2011;31(2):764-74. doi: 10.1523/JNEUROSCI.5052-10.2011.

Menzel et al., A QTL influencing F cell production maps to a gene encoding a zinc-finger protein on chromosome 2p15. Nat Genet. Oct. 2007;39(10):1197-9. Epub Sep. 2, 2007.

Methot et al., Exploration of the internal cavity of histone deacetylase (HDAC) with selective HDAC1/HDAC2 inhibitors (SHI-1:2). Bioorg Med Chem Lett. Feb. 1, 2008;18(3):973-8. doi: 10.1016/j.bmcl.2007.12.031. Epub Jan. 7, 2008.

Miller et al., Histone deacetylase inhibitors. J Med Chem. Nov. 20, 2003;46(24):5097-116. Review.

Monfils et al., Extinction-reconsolidation boundaries: key to persistent attenuation of fear memories. Science. May 15, 2009;324(5929):951-5. doi: 10.1126/science.1167975. Epub Apr. 2, 2009.

Mullin, Crystallization and precipitation. In: Ullmann's encyclopedia of industrial chemistry. 2002;1-51.

Mullin, Crystallization. In: Kirk-Othmer encyclopedia of chemical technology. 2002;95-147.

Namdar et al., Selective inhibition of histone deacetylase 6 (HDAC6) induces DNA damage and sensitizes transformed cells to anticancer agents. Proc Natl Acad Sci U S A. Nov. 16, 2010;107(46):20003-8. doi: 10.1073/pnas.1013754107. Epub Oct. 29, 2010.

Newmark et al., Preparation and properties of adducts of streptokinase-plasmin complex with polyethylene glycol and pluronic polyol F 38. J Appl Biochem. 1982;4:185-9.

Ogino et al., Syntheses and structure-activity relationships of novel, potent, and selective trans-2-[3-oxospiro[isobenzofuran-1(3H),1'-cyclohexan]-4'-yl]benzimidazole NPY Y5 receptor antagonists. Bioorg Med Chem Lett. Sep. 15, 2008;18(18):4997-5001. doi: 10.1016/j.bmcl.2008.08.021.

O'Malley et al., Virtual medicinal chemistry: in silico pre-docking functional group transformation for discovery of novel inhibitors of botulinum toxin serotype A light chain. Bioorg Med Chem Lett. May 1, 2013;23(9):2505-11. doi: 10.1016/j.bmcl.2013.03.030. Epub Mar. 18, 2013.

Oehme et al., Histone deacetylase 8 in neuroblastoma tumorigenesis. Clin Cancer Res. Jan. 1, 2009;15(1):91-9. doi: 10.1158/1078-0432.CCR-08-0684.

Olson et al., Discovery of the first histone deacetylase 6/8 dual inhibitors. J Med Chem. Jun. 13, 2013;56(11):4816-20. doi: 10.1021/jm400390r. Epub May 29, 2013. Supplementary Information. S1-20.

Oswein et al., Aerosolization of Protein Pharmaceuticals. Proceedings of Symposium on Respiratory Drug Delivery II. Keystone, Colorado. Mar. 1990. 34 pages.

Park et al., Histone deacetylases 1, 6 and 8 are critical for invasion in breast cancer. Oncol Rep. Jun. 2011;25(6):1677-81. doi: 10.3892/or.2011.1236. Epub Mar. 28, 2011.

Platt et al., Hydroxyurea enhances fetal hemoglobin production in sickle cell anemia. J Clin Invest. Aug. 1984;74(2):652-6.

Rai et al., Two new pimelic diphenylamide HDAC inhibitors induce sustained frataxin upregulation in cells from Friedreich's ataxia patients and in a mouse model. PLoS One. Jan. 21, 2010;5(1):e8825. doi: 10.1371/journal.pone.0008825.

Rivieccio et al., HDAC6 is a target for protection and regeneration following injury in the nervous system. Proc Natl Acad Sci U S A. Nov. 17, 2009;106(46):19599-604. doi: 10.1073/pnas.0907935106. Epub Nov. 2, 2009.

Roozendaal et al., Membrane-associated glucocorticoid activity is necessary for modulation of long-term memory via chromatin modification. J Neurosci. Apr. 7, 2010;30(14):5037-46. doi: 10.1523/JNEUROSCI.5717-09.2010.

Rouhi, The right stuff, from research and development to the clinic, getting drug crystals right is full of pitfalls. Chem. Eng. News. Feb. 24, 2003;81(8):32-5.

Sankaran et al., Developmental and species-divergent globin switching are driven by BCL11A. Nature. Aug. 27, 2009;460(7259):1093-7. doi: 10.1038/nature08243. Epub Aug. 5, 2009.

Sankaran et al., Human fetal hemoglobin expression is regulated by the developmental stage-specific repressor BCL11A. Science. Dec. 19, 2008;322(5909):1839-42. doi: 10.1126/science.1165409. Epub Dec. 4, 2008.

Schultz et al., Kinetics and comparative reactivity of human class I and class IIb histone deacetylases. Biochemistry. Aug. 31, 2004;43(34):11083-91.

Silverman, Prodrugs and drug delivery systems. In: The organic chemistry of drug design and drug action. 1992. Chapter 8:354-5.

Smith et al., Pulmonary deposition and clearance of aerosolized alpha-1-proteinase inhibitor administered to dogs and to sheep. J Clin Invest. Oct. 1989;84(4):1145-54.

Song et al., Synthesis of New Crown Ethers Containing Appended Pyridine, 10-hydroxybenzoquinoline, 8-hydroxyquinoline and 2-amino-1-hydroxybiphenyl Sidearms. Supramolecular Chemistry. 2002;14(2-3):263-269.

Stefanko et al., Modulation of long-term memory for object recognition via HDAC inhibition. Proc Natl Acad Sci U S A. Jun. 9, 2009;106(23):9447-52. doi: 10.1073/pnas.0903964106. Epub May 26, 2009.

Steinberg et al., Effect of hydroxyurea on mortality and morbidity in adult sickle cell anemia: risks and benefits up to 9 years of treatment. JAMA. Apr. 2, 2003;289(13):1645-51. Erratum in: JAMA. Aug. 13, 2003;290(6):756.

Steinberg et al., Management of sickle cell disease. N Engl J Med. Apr. 1, 1999;340(13):1021-30. Review.

Suuronen et al., Regulation of microglial inflammatory response by histone deacetylase inhibitors. J Neurochem. Oct. 2003;87(2):407-16.

Tsankova et al., Sustained hippocampal chromatin regulation in a mouse model of depression and antidepressant action. Nat Neurosci. Apr. 2006;9(4):519-25. Epub Feb. 26, 2006.

(56) References Cited

OTHER PUBLICATIONS

Turconi et al., Synthesis of a New Class of 2,3-Dihydro-2-oxo-1H-benzimidazole-1-carboxylic Acid Derivatives as Highly Potent 5-HT$_3$ Receptor Antagonists. J Med Chem. 1990;33:2101-8.

Uda et al., Genome-wide association study shows BCL11A associated with persistent fetal hemoglobin and amelioration of the phenotype of beta-thalassemia. Proc Natl Acad Sci U S A. Feb. 5, 2008;105(5):1620-5. doi: 10.1073/pnas.0711566105. Epub Feb. 1, 2008.

Vecsey et al., Histone deacetylase inhibitors enhance memory and synaptic plasticity via CREB:CBP-dependent transcriptional activation. J Neurosci. Jun. 6, 2007;27(23):6128-40.

Wagner et al., An Isochemogenic Set of Inhibitors to Define the Therapeutic Potential of Histone Deacetylases in β-Cell Protection. ACS Chem Biol. Feb. 19, 2016;11(2):363-74. doi: 10.1021/acschembio.5b00640.

Wagner et al., Potent and selective inhibition of histone deacetylase 6 (HDAC6) does not require a surface-binding motif. J Med Chem. Feb. 28, 2013;56(4):1772-6. doi: 10.1021/jm301355j. Epub Feb. 18, 2013.

Wagner et al., Small molecule inhibitors of zinc-dependent histone deacetylases. Neurotherapeutics. Oct. 2013;10(4):589-604. doi: 10.1007/s13311-013-0226-1.

Weïwer et al., Therapeutic potential of isoform selective HDAC inhibitors for the treatment of schizophrenia. Future Med Chem. Sep. 2013;5(13):1491-508. doi: 10.4155/fmc.13.141.

Wolff, Burger's Medicinal Chemistry, 5th ed. Part I. John Wiley & Sons. 1995;975-7.

Xiong et al., HDAC6 mutations rescue human tau-induced microtubule defects in *Drosophila*. Proc Natl Acad Sci U S A. Mar. 19, 2013;110(12):4604-9. doi: 10.1073/pnas.1207586110. Epub Mar. 4, 2013. 6 pages.

Canadian Office Action dated Jul. 15, 2019 for Application No. 2834548.

Japanese Decision of Rejection dated Jun. 10, 2019 for Application No. JP 2017-212845.

Canadian Examination Report dated Jul. 30, 2019 for Application No. 2880117.

[No Author Listed] Chemical Abstracts STN Database Record for 1218056-74-6. Apr. 11, 2010. 1pg.

[No Author Listed] Chemical Abstracts STN Database Record for RN 926190-69-4 and 926236-00-2. Mar. 13, 2007.

[No Author Listed] Chemical Abstracts STN Database Record for RN 1039887-48-3. Aug. 20, 2008.

Charon et al, Synthesis and biological evaluation of benzimidazole derivatives as potent AMP-activated protein kinase activators. Bioorg Med Chem. Jul. 1, 2006;14(13):4490-518. Epub Mar. 2, 2006.

Dobrota et al., Expedient access to fused quinoxalines via Dess—Martin periodinane-mediated cyclization of unsymmetrical phenylenediamide derivatives. Tetrahedron Letters 51(9):1262-1264.

\* cited by examiner

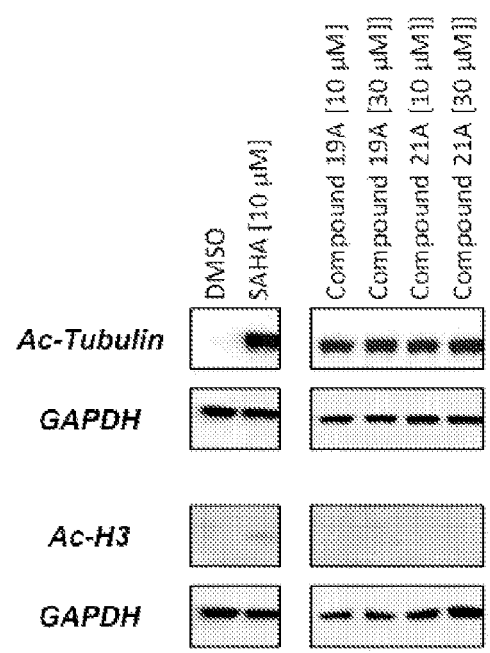

CYCLOALKENYL HYDROXAMIC ACID DERIVATIVES AND THEIR USE AS HISTONE DEACETYLASE INHIBITORS

CROSS REFERENCE TO RELATED APPLICATION

This application is a continuation of and claims priority under 35 U.S.C. § 120 to U.S. Application, U.S. Ser. No. 14/654,296, filed Jun. 19, 2015, which is a national stage filing under 35 U.S.C. § 371 of International PCT Application, PCT/US2013/076618, filed Dec. 19, 2013, which claims priority to, and the benefit of, U.S. Application No. 61/739,967, filed on Dec. 20, 2012, the entire contents of each of which are incorporated herein by reference.

FIELD OF THE INVENTION

The present invention relates generally to selective inhibitors of histone deacetylase and to methods of making and using them. These compounds are useful for treating, and/or preventing various diseases, disorders, or conditions, including for example, neurological disorders, infectious diseases, inflammatory diseases, neoplastic diseases, metabolic disorders, autoimmune and heteroimmune diseases in humans and animals.

BACKGROUND OF THE INVENTION

Histone deacetylases (HDACs) are enzymes that catalyze the removal of acetyl groups from the ε-nitrogen of lysine residues on histone as well as non-histone proteins. Such posttranslational modifications can regulate numerous cellular processes, including gene expression, making these enzymes attractive targets for the treatment of cancer as well as neurological, metabolic, neoplastic, inflammatory, autoimmune, heteroimmune, and infectious diseases. These important enzymes can be divided into the NAD+-dependent Sirtuins (class III) and the Zn-dependent HDACs. The latter can be further divided into three classes, one of which is split into two subclasses class I (HDACs 1, 2, 3, and 8), class IIa (HDACs 4, 5, 7, and 9), class IIb (HDACs 6 and 10), and class IV (HDAC11). Currently, most of the clinically relevant HDAC inhibitors (i.e., vorinostat, romidepsin, and valproic acid) inhibit multiple HDAC isoforms and exhibit significant toxicity. However, it is believed that selective inhibition of only the desired HDAC isoforms can lead to drugs that are better tolerated and results in fewer side effects.

There is much to be understood about the family of HDACs, including the varying functions of different HDACs and the range of HDAC substrates. In order to learn more about the role that the individual HDACs play, it is important to develop compounds showing selectivity for individual isoforms or small subsets of these isoforms. While some degree of isoform selectivity has been shown by a few compounds, this problem of identifying selective inhibitors is far from solved, and is complicated by the interactions of the HDACs with each other as well as other proteins (cofactors) that can possibly alter their interaction with various inhibitors (Glaser, et al., Biochem. Biophys. Res. Commun., 325, 683-690 (2004)). Additionally, until now, medicinal chemists have focused on developing compounds selective for either a single isoform or a few isoforms within the same class. The possibility of achieving selectivity for HDAC isoforms belonging to different classes is also an important problem to be solved. Clinically, the optimal dose, timing and duration of therapy, as well as the most appropriate agents to combine with HDAC inhibitors, are also still to be defined.

There is a need to identify specific/selective HDAC inhibitors and to identify the structural features required for potent HDAC inhibitory activity.

SUMMARY OF THE INVENTION

The problem to be solved by the present invention is the identification of selective HDAC inhibitors and methods of making and using them in the treatment and/or prevention of diseases. Various HDAC inhibitors belonging to different structural classes have been developed. Many inhibitors are characterized by a pan-HDAC inhibitory profile. The potential advantages of isoform selective inhibitors over pan-HDAC inhibitors in terms of efficacy and/or toxicity remain to be defined. However, it is thought that the selective inhibition of only the desired HDAC inhibitors will lead to better tolerated and less toxic drugs.

Many HDAC inhibitors are designed as structural mimics of acetyl-lysine, and as a result, often contain a zinc-binding group (ZBG), a linker and a cap group. These pharmacophoric elements are exemplified by the structure of SuberoylAnilide Hydroxamic Acid (SAHA), a non-selective inhibitor of HDACs 1, 2, 3, 6 and 8, which possesses a 6-carbon alkyl chain linking a hydroxamic acid to a capping moiety. The solution of the present invention is the development of compounds selective for either a single HDAC isoform or a few HDAC isoforms. In one aspect, the solution of the present invention is the development of HDAC inhibitors which are small in size and possess a core cyclic-nonaromatic ring structure. Furthermore, the compounds of the invention contain a hydroxamic moiety which is directly attached to the core cyclic-nonaromatic ring. This structural feature is much different compared to SAHA where the hydroxamic acid moiety is directly attached to an acyclic alkyl chain. This structure is also much different compared to other selective HDAC 6 inhibitors such as tubacin and tubastatin A.

A major challenge in the area of central nervous system (CNS) drug discovery is the efficient delivery of small molecules across the blood brain barrier (BBB). The concept of ligand efficiency (lig E) which is defined as biological activity per molecular size has become a beneficial tool in medicinal chemistry. The solution of the present invention is the development of compounds which possess preferable lead-like characteristics for CNS drug discovery. In one aspect, the solution of the present invention is the development of HDAC inhibitors which may have one or more characteristics associated with high ligand efficiency. In one aspect, the solution of the present invention is compounds that may efficiently cross the BBB.

The invention provides compounds useful for the inhibition of histone deacetylase. Specifically, the invention provides a compound having the formula I:

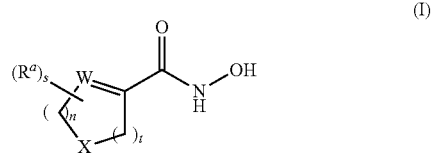

or a pharmaceutically acceptable salt, solvate, or prodrug thereof. In formula I, the variables W, X, n, s, t, and $R^a$ can be selected from the respective groups of chemical moieties later defined in the detailed description.

In addition, the invention provides pharmaceutical compositions comprising an effective amount of a compound of the invention and a pharmaceutical carrier, diluent, or excipient.

In one aspect, the invention provides methods for the use of compounds of the invention. In one aspect, the invention provides a method of treating or preventing a disease, disorder, or condition in a subject comprising administering to the subject in need thereof an effective amount of a compound of the invention or a pharmaceutically acceptable salt, solvate, tautomer, or prodrug thereof. In one aspect, the invention provides treating a disease, disorder, or condition. In one aspect, the invention provides preventing a disease, disorder, or condition.

In one aspect, the invention provides a method of treating or preventing a disease, disorder, or condition in a subject comprising administering to the subject in need thereof an effective amount of a compound of the invention or a pharmaceutically acceptable salt, solvate, tautomer, or prodrug thereof, wherein the disease, disorder, or condition is selected from neurological disorder, infectious disease, inflammatory disease, neoplastic disease, metabolic disease, autoimmune disease, heteroimmune disease, and a disease, disorder, or condition mediated by or linked to T-cell dysregulation.

In one aspect, the invention provides a method of treating or preventing a neurological disorder in a subject comprising administering to the subject in need thereof an effective amount of a compound of the invention or a pharmaceutically acceptable salt, solvate, tautomer, or prodrug thereof. In one aspect, the invention provides treating a neurological disorder. In one aspect, the invention provides preventing a neurological disorder.

In one aspect, the invention provides a method of treating or preventing a neurological disorder in a subject comprising administering to the subject in need thereof an effective amount of a compound of the invention or a pharmaceutically acceptable salt, solvate, tautomer, or prodrug thereof, wherein the neurological disorder is selected from Charcot-Marie-Tooth disease, Alzheimer's disease, Parkinson's diseases, Huntington's disease, multiple sclerosis, amyotrophic lateral sclerosis, Creutzfeldt-Jakob disease, Lewy body dementia, vascular dementia, muscular atrophy, seizure induced memory loss, schizophrenia, Rubinstein Taybi syndrome, Rett Syndrome, Fragile X, ADHD, dyslexia, bipolar disorder and social, cognitive and learning disorders associated with autism, traumatic head injury, and attention deficit disorder.

In one aspect, the invention provides a method of treating or preventing a neurological disorder in a subject comprising administering to the subject in need thereof an effective amount of a compound of the invention or a pharmaceutically acceptable salt, solvate, tautomer, or prodrug thereof, wherein the neurological disorder is a neuropsychiatric disorder.

In one aspect, the invention provides a method of treating or preventing an infectious disease in a subject comprising administering to the subject in need thereof an effective amount of a compound of the invention or a pharmaceutically acceptable salt, solvate, tautomer, or prodrug thereof. In one aspect, the invention provides treating an infectious disease. In one aspect, the invention provides preventing an infectious disease.

In one aspect, the invention provides a method of treating or preventing an infectious disease in a subject comprising administering to the subject in need thereof an effective amount of a compound of the invention or a pharmaceutically acceptable salt, solvate, tautomer, or prodrug thereof, wherein the infectious disease is a fungal disease or infection.

In one aspect, the invention provides a method of treating or preventing an infectious disease in a subject comprising administering to the subject in need thereof an effective amount of a compound of the invention or a pharmaceutically acceptable salt, solvate, tautomer, or prodrug thereof, wherein the infectious disease is a protozoal infection.

In one aspect, the invention provides a method of treating or preventing an inflammatory disease in a subject comprising administering to the subject in need thereof an effective amount of a compound of the invention or a pharmaceutically acceptable salt, solvate, tautomer, or prodrug thereof. In one aspect, the invention provides treating an inflammatory disease. In one aspect, the invention provides preventing an inflammatory disease.

In one aspect, the invention provides a method of treating or preventing an inflammatory disease in a subject comprising administering to the subject in need thereof an effective amount of a compound of the invention or a pharmaceutically acceptable salt, solvate, tautomer, or prodrug thereof, wherein the inflammatory disease is selected from osteoarthritis, rheumatoid arthritis, lupus, inflammatory bowel disease, Crohn's Disease, ulcerative colitis, anemia, leukocytosis, asthma, chronic obstructive pulmonary disease, appendicitis, bronchitis, bursitis, conjunctivitis, dermatitis, encephalitis, myelitis myocarditis, sinusitis, dermatitis, psoriasis, eczema, and acne.

In one aspect, the invention provides a method of treating or preventing a neoplastic disease in a subject comprising administering to the subject in need thereof an effective amount of a compound of the invention or a pharmaceutically acceptable salt, solvate, tautomer, or prodrug thereof. In one aspect, the invention provides treating a neoplastic disease. In one aspect, the invention provides preventing a neoplastic disease.

In one aspect, the invention provides a method of treating or preventing a neoplastic disease in a subject comprising administering to the subject in need thereof an effective amount of a compound of the invention or a pharmaceutically acceptable salt, solvate, tautomer, or prodrug thereof, wherein the neoplastic disease is cancer.

In one aspect, the invention provides a method of treating or preventing cancer in a subject comprising administering to the subject in need thereof an effective amount of a compound of the invention or a pharmaceutically acceptable salt, solvate, tautomer, or prodrug thereof, wherein the cancer is selected from leukemia, T-cell lymphoma, Hodgkin's Disease, non-Hodgkin's lymphomas, multiple myeloma, brain tumor, neuroblastoma, bone tumor, soft-tissue sarcoma, head and neck cancer, genitourinary cancer, lung cancer, breast cancer, pancreatic cancer, melanoma, stomach cancer, brain cancer, liver cancer, thyroid cancer, clear cell carcinoma, uterine cancer and ovarian cancer.

In one aspect, the invention provides a method of treating or preventing a metabolic disease in a subject comprising administering to the subject in need thereof an effective amount of a compound of the invention or a pharmaceutically acceptable salt, solvate, tautoamer, or prodrug thereof. In one aspect, the invention provides treating a metabolic disease. In one aspect, the invention provides preventing a metabolic disease.

In one aspect, the invention provides a method of treating or preventing a metabolic disease in a subject comprising administering to the subject in need thereof an effective amount of a compound of the invention or a pharmaceutically acceptable salt, solvate, tautoamer, or prodrug thereof, wherein the metabolic disease is selected from acid lipase disease, Barth Syndrome, central pontine myelinolysis, Farber's Disease, gangliosidoses, Hunter Syndrome, trimethylaminuria, Lesch-Nyhan Syndrome, lipid Storage disease, metabolic diseases of muscle, mitochondrial myopathies, mucolipidoses, mucopolysacchardoses, Pompe Disease, Type I glycogen storage disease, urea cycle disease, hyperoxaluria, diabetes (e.g., Type I diabetes or Type II diabetes), obesity, and diabesity.

In one aspect, the invention provides a method of treating or preventing an autoimmune disease in a subject comprising administering to the subject in need thereof an effective amount of a compound of the invention or a pharmaceutically acceptable salt, solvate, tautomer, or prodrug thereof. In one aspect, the invention provides treating an autoimmune disease. In one aspect, the invention provides preventing an autoimmune disease.

In one aspect, the invention provides a method of treating or preventing an autoimmune disease in a subject comprising administering to the subject in need thereof an effective amount of a compound of the invention or a pharmaceutically acceptable salt, solvate, tautomer, or prodrug thereof, wherein the autoimmune disease is selected from diabetes, thyroiditis, Graves' disease, Guillain-Barre syndrome, Addison's disease, scleroderma, primary biliary cirrhosis, Reiter's syndrome, psoriasis, chronic fatigue, and endometriosis.

In one aspect, the invention provides a method of treating or preventing a heteroimmune disease in a subject comprising administering to the subject in need thereof an effective amount of a compound of the invention or a pharmaceutically acceptable salt, solvate, tautomer, or prodrug thereof. In one aspect, the invention provides treating a heteroimmune disease. In one aspect, the invention provides preventing a heteroimmune disease.

In one aspect, the invention provides a method of treating or preventing a heteroimmune disease in a subject comprising administering to the subject in need thereof an effective amount of a compound of the invention or a pharmaceutically acceptable salt, solvate, tautomer, or prodrug thereof, wherein the heteroimmune disease is selected from graft versus host disease, transplantation, transfusion, anaphylaxis, allergic conjunctivitis, and allergic rhinitis.

In one aspect, the invention provides a method of treating or preventing a disease or condition mediated by or linked to T-cell dysregulation in a subject comprising administering to the subject in need thereof an effective amount of a compound of the invention or a pharmaceutically acceptable salt, solvate, tautoamer, or prodrug thereof. In one aspect, the invention provides treating a disease or condition mediated by or linked to T-cell dysregulation. In one aspect, the invention provides preventing a disease or condition mediated by or linked to T-cell dysregulation.

In one aspect, the invention provides a method of treating or preventing a disease or condition mediated by or linked to T-cell dysregulation in a subject comprising administering to the subject in need thereof an effective amount of a compound of the invention or a pharmaceutically acceptable salt, solvate, tautoamer, or prodrug thereof, wherein the disease or condition is selected from arthritis (e.g., rheumatoid arthritis and juvenile idiopathic arthritis), colitis, allograft rejection, lupus, asthma, psoriasis, inflammation, allergy, allergic encephalomyelitis, autoimmune lymphoproliferative disorder, autoimmune polyglandular syndrome type II, type I diabetes, lymphomas (e.g., T-cell lymphoma and lymphoid interstitial lymphoma), Wiskott-Aldrich syndrome, myasthenia gravis, and infectious diseases (e.g., HIV, *H. pylori* infection, hepatitis B infection, and hepatitis C infection). In one aspect, the disease or condition is caused by T-cell dysregulation.

In one aspect, the invention provides a method of treating or preventing a disease, disorder, or condition in a subject comprising administering to a subject in need thereof an effective amount of a compound of the invention or a pharmaceutically acceptable salt, solvate or prodrug thereof in combination with a second agent (dual therapy). In one aspect, the invention provides treating a disease, disorder, or condition. In one aspect, the invention provides preventing a disease, disorder, or condition.

In one aspect, the invention provides a method of treating or preventing a disease, disorder, or condition in a subject comprising administering to a subject in need thereof an effective amount of a compound of the invention or a pharmaceutically acceptable salt, solvate or prodrug thereof, wherein said compound is administered by a route selected from oral, parenteral, intramuscular, intranasal, sublingual, intratracheal, inhalation, ocular, vaginal, rectal, and intracerebroventricular. In one aspect, the invention provides treating a disease, disorder, or condition. In one aspect, the invention provides preventing a disease, disorder, or condition.

In one aspect, the invention provides a method wherein the compound of the invention or a pharmaceutically acceptable salt, solvate, or prodrug thereof is administered by a route selected from oral, parenteral, intramuscular, intranasal, sublingual, intratracheal, inhalation, ocular, vaginal, rectal, and intracerebroventricular.

In one aspect, the invention provides a method, wherein the subject is a human.

In one aspect, the invention provides a compound or a pharmaceutically acceptable salt, solvate, tautomer, or prodrug thereof, for use in the manufacture of a medicament for the treatment or prevention of a disease, disorder, or condition in a subject, wherein the medicament is administered to the subject in need thereof.

In one aspect, the invention provides a compound or a pharmaceutically acceptable salt, solvate, tautomer, or prodrug thereof, for use in the manufacture of a medicament for the treatment or prevention of a disease, disorder, or condition in a subject, wherein the medicament is administered to the subject in need thereof, wherein the disease, disorder, or condition is selected from neurological disorder, infectious disease, inflammatory disease, neoplastic disease, metabolic disease, autoimmune disease, heteroimmune disease, and a disease, disorder, or condition mediated by or linked to T-cell dysregulation.

In one aspect, the invention provides a compound or a pharmaceutically acceptable salt, solvate, tautomer, or prodrug thereof, for use in treating or preventing a disease, disorder, or condition in a subject.

In one aspect, the invention provides a compound or a pharmaceutically acceptable salt, solvate, tautomer, or prodrug thereof, for use in treating or preventing a disease, disorder, or condition in a subject, wherein the medicament is administered to the subject in need thereof, wherein the disease, disorder, or condition is selected from neurological disorder, infectious disease, inflammatory disease, neoplastic disease, metabolic disease, autoimmune disease, heteroimmune disease, and a disease, disorder, or condition mediated by or linked to T-cell dysregulation.

In one aspect, the invention provides a method of synthesizing a compound of the invention or a pharmaceutically acceptable salt, solvate, or prodrug thereof.

In one aspect, the invention provides a kit containing one or more compounds of the invention or a pharmaceutically acceptable salt, solvate, or prodrug thereof. In one aspect, the kit further contains a pharmaceutically active ingredient.

BRIEF DESCRIPTION OF THE DRAWINGS

FIG. 1 is a Western blot showing detection of acetylated α-tubulin (Ac-tubulin) and acetyl histone H3 (Ac-H3) following treatment of HeLa cells with compounds of the invention and SAHA (positive control).

DETAILED DESCRIPTION OF THE INVENTION

The invention provides compounds, pharmaceutical compositions and methods for inhibiting enzymatic activity of one or more histone deacetylases. In one aspect, the invention provides compounds, pharmaceutical compositions and methods for inhibiting the enzymatic activity of histone deacetylase 6 and/or 8. The invention also provides compounds, pharmaceutical compositions and methods for treating and/or preventing various diseases, disorder, and/or conditions, including for example, cancer, neurological disorders, psychiatric disorders, infectious diseases, inflammatory diseases, neoplastic diseases, metabolic diseases, autoimmune diseases, and heteroimmune diseases. The patent and scientific literature referred to herein establishes knowledge that is available to those with skill in the art. The issued patents, applications, and references that are cited herein are hereby incorporated by reference to the same extent as if each is specifically and individually indicated to be incorporated by reference. In the case of inconsistencies, the present disclosure will prevail.

For purposes of the present invention, the following definitions will be used (unless expressly stated otherwise):

The general chemical terms used throughout have their usual meanings. For example, the term alkyl refers to a branched or unbranched saturated hydrocarbon group. The term "n-alkyl" refers to an unbranched alkyl group. The term "$C_x$-$C_y$ alkyl" refers to an alkyl group having between x and y carbon atoms, inclusively, in the branched or unbranched hydrocarbon group. By way of illustration, but without limitation, the term "$C_1$-$C_8$ alkyl" refers to a straight chain or branched hydrocarbon moiety having 1, 2, 3, 4, 5, 6, 7, or 8 carbon atoms. "$C_1$-$C_6$" refers to a straight chain or branched hydrocarbon moiety having 1, 2, 3, 4, 5, or 6 carbon atoms. "$C_1$-$C_4$ alkyl" refers to a straight chain or branched hydrocarbon moiety having 1, 2, 3, or 4 carbon atoms, including methyl, ethyl, n-propyl, isopropyl, n-butyl, isobutyl, sec-butyl, and tert-butyl. The term "$C_1$-$C_4$ n-alkyl" refers to straight chain hydrocarbon moieties having from 1 to 4 carbon atoms, including methyl, ethyl, n-propyl, and n-butyl. The term "$C_3$-$C_6$ cycloalkyl" refers to cyclopropyl, cyclobutyl, cyclopentyl, and cyclohexyl. The term "$C_3$-$C_7$ cycloalkyl" also includes cycloheptyl. The term "$C_3$-$C_8$ cycloalkyl" also includes cyclooctyl. Cycloalkylalkyl refers to cycloalkyl moieties linked through an alkyl linker chain, as for example, but without limitation, cyclopropylmethyl, cyclopropylethyl, cyclopropylpropyl, cyclopropylbutyl, cyclobutylmethyl, cyclobutylethyl, cyclobutylpropyl, cyclopentylmethyl, cyclopentylethyl, cyclopentylpropyl, cyclohexylmethyl, cyclohexylethyl, and cyclohexylpropyl. Each alkyl, cycloalkyl, and cycloalkylalkyl group may be optionally substituted as specified herein.

The term "$C_4$-$C_8$ cycloalkenyl" refers to cyclobutenyl, cyclopentyl, cyclohexenyl, cycloheptenyl, and cyclooctenyl rings having one or more sites of unsaturation e.g., one or more double bonds.

The term "3 to 10 membered ring" includes a 3, 4, 5, 6, 7, 8, 9, and 10-membered ring.

The terms "alkoxy", "phenyloxy", "benzoxy" and "pyrimidinyloxy" refer to an alkyl group, phenyl group, benzyl group, or pyrimidinyl group, respectively, each optionally substituted, that is bonded through an oxygen atom.

The term "halogen" refers to fluoro, chloro, bromo, or iodo.

The term "hydroxyl" means OH.

The term "aryl" or "aromatic ring", alone or in combination, means a carbocyclic aromatic system containing one, two or three rings wherein such rings may be attached together in a pendent manner or may be fused. The term "aryl" or "aromatic ring" embraces aromatic radicals such as phenyl (e.g., $C_6H_5$—), naphthyl, tetrahydronapthyl, indanyl and biphenyl, and includes carbocyclic aryl, heterocyclic aryl and biaryl groups, all of which may be optionally substituted.

The term "heteroaryl" or "heteroaromatic ring" as used herein includes 5-, 6- and 7-membered single-ring aromatic groups that may include 1, 2, 3, or 4 heteroatoms selected from nitrogen, oxygen and sulfur, for example, pyrrole, furan, thiophene, imidazole, oxazole, thiazole, triazole, pyrazole, pyridine, pyrazine, pyridazine, azepine, oxepine, oxazine, triazine and pyrimidine, and the like. Those aryl groups having heteroatoms in the ring structure may also be referred to as "aryl heterocycles" or "heteroaromatics." A heteroaryl or heteroaromatic ring can be monocyclic, bicyclic, or tricyclic, wherein such rings may be attached together in a pendent manner or may be fused. In one aspect, the heteroaryl or heteroaromatic ring is a 5-, 6-, or 7-membered single ring that includes 1, 2, 3, or 4 heteroatoms. A heteroaryl or heteroaromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like.

The term "heterocyclic ring" or "heterocycle" is taken to mean a saturated, unsaturated, or partially unsaturated containing 1, 2, 3, or 4 heteroatoms selected from nitrogen, oxygen and sulfur, said ring optionally being benzofused. A heterocylic ring can be multicyclic, e.g., bicyclic or tricyclic. The term "3- to 10-membered heterocyclic ring" refers to a ring having 3, 4, 5, 6, 7, 8, 9, or 10 ring atoms. The term "3- to 8-membered heterocyclic ring" refers to a ring having 3, 4, 5, 6, 7, or 8 atoms. The term "3- to 6-membered heterocyclic ring" refers to a ring having 3, 4, 5, or 6 atoms. The term "5- to 6-membered heterocyclic ring" refers to a ring having 5 or 6 atoms. Exemplary heterocyclic rings, for the purposes of the present invention, include furanyl, thiophenyl (thienyl or thiopheneyl), pyrrolyl, pyrrolidinyl, pyridinyl, N-methylpyrrolyl, oxazolyl, isoxazolyl, pyrazolyl, imidazolyl, triazolyl, oxadiazolyl, thiadiazolyl, thiazolyl, thiazolidinyl, N-acetylthiazolidinyl, pyrimidinyl, pyrazinyl, pyridazinyl, and the like. Heterocyclic rings include bicyclic rings for example, 3-azabicyclo[3.1.0] hexane, 8-oxa-3-azabicyclo[3.2.1]octane. Benzofused heterocyclic rings include isoquinolinyl, benzoxazolyl, benzodioxolyl, benzothiazolyl, quinolinyl, benzofuranyl, benzothiophenyl, indolyl, and the like, all of which may be optionally substituted, which also of course includes optional substitution on the benzene ring when the heterocycle is benzofused.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds unless otherwise specified. In a broad aspect, the permissible substituents include acyclic and cyclic, branched and unbranched, carbocyclic and heterocyclic, aromatic and nonaromatic substituents of organic compounds. The permissible substituents can be one or more and the same or different for appropriate organic compounds. For purposes of this invention, the heteroatoms such as nitrogen may have any permissible substituents of organic compounds described herein which satisfy the valences of the heteroatoms. This invention is not intended to be limited in any manner by the permissible substituents of organic compounds.

The term "pharmaceutical" or "pharmaceutically acceptable" when used herein as an adjective, means substantially non-toxic and substantially non-deleterious to the recipient.

By "pharmaceutical formulation" it is further meant that the carrier, solvent, excipient(s) and salt must be compatible with the active ingredient of the formulation (e.g., a compound of the invention). It is understood by those of ordinary skill in this art that the terms "pharmaceutical formulation" and "pharmaceutical composition" are generally interchangeable, and they are so used for the purposes of this application.

The term "acid addition salt" refers to a salt of a compound of the invention prepared by reaction of a compound of the invention with a mineral or organic acid. For exemplification of pharmaceutically acceptable acid addition salts see, e.g., Berge, S. M, Bighley, L. D., and Monkhouse, D. C., J. Pharm. Sci., 66:1, 1977. Compounds of this invention which are amines, are basic in nature and accordingly react with any of a number of inorganic and organic acids to form pharmaceutically acceptable acid addition salts.

Pharmaceutically acceptable acid addition salts of the invention can be formed by reacting a compound of the invention with an equimolar or excess amount of acid. Alternatively, hemi-salts can be formed by reacting a compound of the invention with the desired acid in a 2:1 ratio, compound to acid. The reactants are generally combined in a mutual solvent such as diethylether, tetrahydrofuran, methanol, ethanol, isopropanol, benzene, or the like. The salts normally precipitate out of solution within about one hour to about ten days and can be isolated by filtration or other conventional methods.

Inorganic acids commonly employed to form such salts include hydrochloric acid, hydrobromic acid, hydroiodic acid, sulfuric acid, phosphoric acid, and the like. Organic acids commonly employed to form such salts include p-toluenesulfonic acid, methanesulfonic acid, oxalic acid, p-bromophenylsulfonic acid, carbonic acid, succinic acid, citric acid, benzoic acid, acetic acid and the like.

Examples of such pharmaceutically acceptable salts thus are sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, hemisuccinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like.

Some of the compounds of the present invention may exist in unsolvated as well as solvated forms such as, for example, hydrates.

The invention includes polymorphs of a compound of the invention. The term "polymorph" means a crystal structure in which a compound of the invention can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of a compound of the invention can be prepared by crystallization under different conditions.

Since prodrugs are known to enhance numerous desirable qualities of pharmaceuticals (solubility, bioavailability, manufacturing, etc.), the compounds of the present invention can be delivered in prodrug form. Thus, the present invention is intended to cover prodrugs of the compounds of the invention, methods of delivering the same and compositions containing the same. "Prodrugs" are intended to include any covalently bonded carriers that release an active parent drug of the present invention in vivo when such prodrug is administered to a mammalian subject. Prodrugs are prepared by modifying functional groups present in the compound in such a way that the modifications are cleaved, either in routine manipulation or in vivo, to the parent compound. Prodrugs include compounds of the invention wherein a hydroxyl or amino, group is bonded to any group that, when the prodrug of the present invention is administered to a mammalian subject, it cleaves to form a free hydroxyl or free amino group, respectively. Examples of prodrugs include, but are not limited to, acetate, formate, and benzoate derivatives of alcohol and amine functional groups in the compounds of the present invention.

"Solvate" means a solvent addition form that contains either a stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; when the solvent is alcohol, the solvate formed is an alcoholate. Hydrates are formed by the combination of one or more molecules of water with one of the substances in which the water retains its molecular state as $H_2O$, such combination being able to form one or more hydrate.

The term "suitable solvent" refers to any solvent, or mixture of solvents, inert to the ongoing reaction that sufficiently solubilizes the reactants to afford a medium within which to effect the desired reaction.

The compounds described herein can have asymmetric centers. Compounds of the present invention containing an asymmetrically substituted atom can be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and can be isolated as a mixture of isomers or as separate isomeric forms. All chiral, diastereomeric, racemic, and geometric isomeric forms of a structure are intended, unless specific stereochemistry or isomeric form is specifically indicated. All processes used to prepare compounds of the present invention and intermediates made therein are considered to be part of the present invention. All tautomers of shown or described compounds are also considered to be part of the present invention.

The invention also includes metabolites of the compounds described herein.

The invention also includes isotopically-labeled compounds, which are identical to those recited in the formulae of the invention, but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, fluorine, such as $^3$H, $^{11}$C, $^{14}$C, $^2$H and $^{18}$F.

Compounds of the present invention and salts, solvates or prodrugs of said compounds that contain the aforementioned isotopes and/or other isotopes of other atoms are within the scope of the present invention. Isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography). PET is useful in brain imaging. Further, substitution with heavier isotopes such as deuterium, i.e., $^2$H, can afford certain therapeutic advantages resulting from greater metabolic stability, for example, increased in vivo half-life or reduced dosage requirements and, hence, may be preferred in some circumstances. Isotopically labeled compounds of this invention can generally be prepared by carrying out the procedures disclosed in the Schemes and/or in the Examples below, by substituting a readily available isotopically labeled reagent for a non-isotopically labeled reagent. In one embodiment, the compounds of the invention, salts, solvates, or prodrugs thereof are not isotopically labelled.

When any variable (e.g., $R^x$) occurs more than one time in any constituent or formula for a compound, its definition at each occurrence is independent of its definition at every other occurrence. Thus, for example, if a group is shown to be substituted with one or more $R^x$ moieties, then $R^x$ at each occurrence is selected independently from the definition of $R^x$. Also, combinations of substituents and/or variables are permissible, but only if such combinations result in stable compounds within a designated atom's normal valency.

As used herein, the term "treat," "treating," or "treatment" herein, is meant decreasing the symptoms, markers, and/or any negative effects of a condition in any appreciable degree in a patient who currently has the condition. In some embodiments, treatment may be administered to a subject who exhibits only early signs of the condition for the purpose of decreasing the risk of developing the disease, disorder, and/or condition.

As used herein, the term "prevent," "prevention," or "preventing" refers to any method to partially or completely prevent or delay the onset of one or more symptoms or features of a disease, disorder, and/or condition. Prevention may be administered to a subject who does not exhibit signs of a disease, disorder, and/or condition.

As used herein, the phrase "inhibit histone deacetylase(s)", "inhibiting histone deacetylase(s)", "inhibition of histone deacetylase(s)", or "histone deacetylase inhibitor(s)" means that compounds of the invention decrease or inhibit the enzymatic activities of histone deacetylase(s) or interfere or block the interaction (binding, reacting, forming a complex, etc.) between histone deacetylase(s) and other cellular components (e.g., proteins, substrates, etc.). In one aspect, compounds of the invention decrease or inhibit the enzymatic activities of histone deacetylase(s). For example, compounds of the invention decrease or inhibit the enzymatic activities of one, two, or more sub-groups of histone deacetylases. For example, compounds of the invention decrease or inhibit the enzymatic activities of HDAC class I and/or HDAC class II. In a further example, compounds of the invention decrease or inhibit the enzymatic activities of HDAC8 and/or HDAC 6. In another aspect, compounds of the invention interfere or block the interaction (binding, reacting, forming a complex, etc.) between histone deacetylase(s) and other cellular components. In one embodiment, the other cellular component is a protein, e.g., a protein substrate of a histone deacetylase. For example, compounds of the invention interfere or block the interaction between histone deacetylase(s) and their substrates. For example, compounds of the invention interfere or block the interaction between HDAC class I and/or HDAC class II with their substrates. In a further example, compounds of the invention interfere or block the interaction between HDAC8 and/or HDAC 6 and their substrates.

As used herein, "subject" means a human or animal (in the case of an animal, more typically a mammal). In one aspect, the subject is a human. Such subject can be considered to be in need of treatment with an HDAC inhibitor.

As used herein, "unsaturated" refers to compounds or structures having at least one degree of unsaturation (e.g., at least one double or triple bond).

Combinations of substituents and variables envisioned by this invention are only those that result in the formation of stable compounds. The term "stable" as used herein refers to compounds which possess stability sufficient to allow manufacture and which maintains the integrity of the compound for a sufficient period of time to be useful for the purposes detailed herein (e.g., therapeutic or prophylactic administration to a subject).

Compounds of the Invention

The present invention provides inhibitors of one or more histone deacetylases and their uses. In one aspect, the present invention provides inhibitors of one, two or more sub-groups of histone deacetylases. In one example, the present invention provides inhibitors of HDAC class I or HDAC class II. In another example, the present invention provides inhibitors of both HDAC class I and HDAC class II. In a further example, the present invention provides selective inhibitors of HDAC class I or HDAC class II. In a further example, the present invention provides selective inhibitors of both HDAC class I and HDAC class II. In a further example, the present invention provides inhibitors which are selective inhibitors of HDAC class I and non-selective inhibitors of HDAC class II. In another example, the present invention provides inhibitors which are selective inhibitors of HDAC class II and non-selective inhibitors of HDAC class I. For example, the present invention provides inhibitors of HDAC8 or HDAC 6. For example, the present invention provides inhibitors of both HDAC8 and HDAC 6. For example, the present invention provides selective inhibitors of HDAC 8 or HDAC 6. For example, the present invention provides selective inhibitors of both HDAC8 and HDAC 6. For example, the present invention provides selective inhibitors of HDAC8 and non-selective inhibitors of HDAC6. For example, the present invention provides selective inhibitors of HDAC6 and non-selective inhibitors of HDAC8.

In one aspect, the invention provides a compound of formula I:

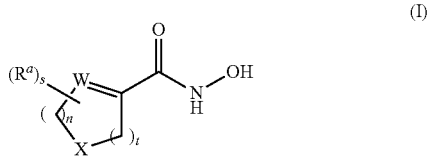

(I)

or a pharmaceutically acceptable salt, solvate, tautomer, or prodrug thereof, wherein
n is 0, 1, 2, 3, 4, or 5;
t is 0, 1, 2, 3, 4, or 5, provided that at least one of n and t is not 0;
s is 0, 1, 2, 3, 4, 5, 6, 7 or 8;
X is $CR^bR^c$, O, $NR^d$, or $S(O)_z$;
W is $CR^e$ or N;
$R^e$ is hydrogen, OH, $C_1$-$C_4$ alkyl, or halogen;
z is 0, 1, or 2;
each $R^a$ is independently selected from halogen, CN, $CF_3$, $OR^f$, $OCF_3$, $C(O)R^g$, $C_1$-$C_8$ alkoxyl, $NR^hR^i$, $SR^j$, $C_1$-$C_8$ alkyl, $C_2$-$C_8$ alkenyl, $C_2$-$C_8$ alkynyl, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring, $(CH_2)_k$-6 to 10-membered aromatic ring, and $(CH_2)_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more $R^1$, provided that when X is $CH_2$, W is CH, and n+t is 3, s is not 0;
each $R^b$, $R^c$, and $R^d$ is independently selected from hydrogen, halogen, CN, $CF_3$, $OR^f$, $OCF_3$, $C(O)R^g$, $C_1$-$C_8$ alkoxyl, $NR^hR^i$, $S(O)_zR^j$, $C_1$-$C_8$ alkyl, $C_2$-$C_8$ alkenyl, $C_2$-$C_8$ alkynyl, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring, $(CH_2)_k$-6 to 10-membered aromatic ring, and $(CH_2)_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more $R^1$;
or $R^e$ is attached to $R^a$ to form a fused ring, wherein said ring is selected from $C_3$-$C_8$ cycloalkyl, $C_4$-$C_8$ cycloalkenyl, 3 to 10-membered saturated or unsaturated heterocyclic ring, 6 to 10-membered aromatic ring, and 3 to 10-membered heteroaromatic ring, wherein said fused ring is unsubstituted or substituted with one or more $R^2$;
or taken together two $R^a$ are attached to form a fused ring, wherein said ring is selected from $C_3$-$C_8$ cycloalkyl, $C_4$-$C_8$ cycloalkenyl, 3 to 10-membered saturated or unsaturated heterocyclic ring, 6 to 10-membered aromatic ring, and 3 to 10-membered heteroaromatic ring, wherein said fused ring is unsubstituted or substituted with one or more $R^2$, provided that when n is 2, t is 0, W is CH, and X is O or S, said fused ring is not unsubstituted phenyl;
or one $R^b$, $R^c$, or $R^d$ is attached to $R^e$ or $R^a$ to form a fused ring, wherein said ring is selected from $C_3$-$C_8$ cycloalkyl, $C_4$-$C_8$ cycloalkenyl, 3 to 10-membered saturated or unsaturated heterocyclic ring, 6 to 10-membered aromatic ring, and 3 to 10-membered heteroaromatic ring, wherein said fused ring is unsubstituted or substituted with one or more $R^2$ (when $R^b$ or $R^c$ is attached to $R^e$ or $R^a$ to form said aromatic or heteroaromatic fused ring, it is understood the remaining $R^b$ or $R^c$ is absent);
or taken together two $R^a$ are attached to form a bridged ring;
or $R^a$ is attached to one $R^b$, $R^c$, or $R^d$ to form a bridged ring;
or $R^b$ and $R^c$ taken together with the carbon atom to which they are attached form C=O;
or two $R^a$ taken together with the carbon atom to which they are attached form a spirocyclic ring selected from a $C_3$-$C_8$ cycloalkyl, $C_4$-$C_8$ cycloalkenyl, or 3 to 10-membered saturated or unsaturated heterocyclic ring, wherein said spirocyclic ring is unsubstituted or substituted with one or more $R^2$;
or $R^b$ and $R^c$ taken together with the carbon atom to which they are attached form a spirocyclic ring selected from a $C_3$-$C_8$ cycloalkyl, $C_4$-$C_8$ cycloalkenyl, or 3 to 10-membered saturated or unsaturated heterocyclic ring, wherein said spirocyclic ring is unsubstituted or substituted with one or more $R^2$;
each $R^g$ is selected from hydrogen, $OR^L$, $NR^mR^o$, $CF_3$, $C_1$-$C_8$ alkyl, $C_2$-$C_8$ alkenyl, $C_2$-$C_8$ alkynyl, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring, $(CH_2)_k$-6 to 10-membered aromatic ring, and $(CH_2)_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more $R^3$;
each $R^f$, $R^h$, $R^i$, $R^j$, $R^L$, $R^m$, and $R^o$ is independently selected from hydrogen, $C_1$-$C_8$ alkyl, $C_2$-$C_8$ alkenyl, $C_2$-$C_8$ alkynyl, $C(O)R^p$, $S(O)_zR^{ij}$, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring, $(CH_2)_k$-6 to 10-membered aromatic ring, and $(CH_2)_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more $R^4$;
each $R^p$ and $R^{ij}$ is independently selected from $OR^q$, $NR^rR^u$, $CF_3$, $C_1$-$C_8$ alkyl, $C_2$-$C_8$ alkenyl, $C_2$-$C_8$ alkynyl, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring, $(CH_2)_k$-6 to 10-membered aromatic ring, and $(CH_2)_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more $R^5$;
each $R^q$, $R^r$, and $R^u$ is independently selected from hydrogen, $C_1$-$C_8$ alkyl, $C_2$-$C_8$ alkenyl, $C_2$-$C_8$ alkynyl, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring, $(CH_2)_k$-6 to 10-membered aromatic ring, and $(CH_2)_k$-3 to 10-membered heteroaromatic ring, wherein said alkyl, alkenyl, alkynyl, cycloalkyl, cycloalkenyl, heterocyclic ring, aromatic ring, and heteroaromatic ring are unsubstituted or substituted with one or more $R^6$;
each $R^1$, $R^2$, $R^3$, $R^4$, $R^5$, and $R^6$ is independently selected from halogen, $CF_3$, $OCF_3$, $C_1$-$C_8$ alkyl, $C_2$-$C_8$ alkenyl, $C_2$-$C_8$ alkynyl, $OC_1$-$C_8$ alkyl, $NH_2$, $NHC_1$-$C_8$ alkyl, N(C$_1$-C$_8$ alkyl)$_2$, C(O)NR$^v$R$^y$, C(O)R$^{aa}$, and C(O)OR$^{bb}$, and (CH$_2$)$_k$-6 to 10-membered aromatic ring, wherein said aromatic ring is unsubstituted or substituted with one or more R$^7$;

each R$^v$, R$^y$, R$^{aa}$, and R$^{bb}$ is independently selected from hydrogen, C$_1$-C$_8$ alkyl, C$_2$-C$_8$ alkenyl, C$_2$-C$_8$ alkynyl, (CH$_2$)$_k$—C$_3$-C$_8$ cycloalkyl, (CH$_2$)$_k$—C$_4$-C$_8$ cycloalkenyl, (CH$_2$)$_k$-3 to 10-membered saturated or unsaturated heterocyclic ring, (CH$_2$)$_k$-6 to 10-membered aromatic ring, and (CH$_2$)$_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more R$^7$;

each R$^7$ is selected from halogen, CF$_3$, OCF$_3$, C$_1$-C$_8$ alkyl, C$_2$-C$_8$ alkenyl, C$_2$-C$_8$ alkynyl, OC$_1$-C$_8$ alkyl, NH$_2$, NHC$_1$-C$_8$ alkyl, and N(C$_1$-C$_8$ alkyl)$_2$; and k is 0, 1, 2, or 3.

In one aspect, the invention provides a compound of formula I, wherein n is 0, 1, or 2 and t is 0, 1, 2, or 3. In one aspect, the invention provides a compound of formula I, wherein n is 0, 1, or 2, and t is 0.

In one aspect, the invention provides a compound of formula I, wherein n is 1 or 2 and t is 0. In one aspect, the invention provides a compound of formula I, wherein n is 2 and t is 0. In one aspect, the invention provides a compound of formula I, wherein n is 0, 1, or 2, and t is 1, 2, or 3. In one aspect, the invention provides a compound of formula I, wherein n is 0 or 1 and t is 2 or 3. In one aspect, the invention provides a compound of formula I, wherein n is 0 or 2 and t is 1 or 3. In one aspect, the invention provides a compound of formula I, wherein n is 1 or 2 and t is 1 or 2. In one aspect, the invention provides a compound of formula I, wherein n is 0 and t is 3. In one aspect, the invention provides a compound of formula I, wherein n is 1 and t is 2. In one aspect, the invention provides a compound of formula I, wherein n is 2 and t is 1. In one aspect, the invention provides a compound of formula I, wherein n is 1 and t is 1. In one aspect, the invention provides a compound of formula I, wherein n is 0 and t is 2. In one aspect, the invention provides a compound of formula I, wherein n is 2 and t is 2.

In one aspect, the invention provides a compound of formula I, wherein when X is CH$_2$, W is CH, and n+t is 3, s is not 0. In one aspect, the invention provides a compound of formula I, wherein when X is CH$_2$, W is CH, n is 0 and t is 3, s is not 0. In one aspect, the invention provides a compound of formula I, wherein when X is CH$_2$, W is CH, n is 1 and t is 2, s is not 0. In one aspect, the invention provides a compound of formula I, wherein when X is CH$_2$, W is CH, n is 2 and t is 1, s is not 0. In one aspect, the invention provides a compound of formula I, wherein when X is CH$_2$, W is CH, n is 3 and t is 0, s is not 0.

In one aspect, the invention provides a compound of formula I, wherein taken together two R$^a$ are attached to form a fused ring, and when n is 2, t is 0, W is CH$_2$, and X is O or S, said fused ring is not unsubstituted phenyl.

In one aspect, the invention provides a compound of formula II:

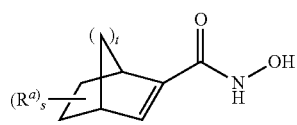

(II)

or a pharmaceutically acceptable salt, solvate, tautomer, or prodrug thereof, wherein R$^a$ is as defined for formula I, s is 0, 1, 2, 3, 4, 5, 6, 7, or 8; and t is 1 or 2.

In one aspect, the invention provides a compound of formula I or II, wherein t is 1. In one aspect, the invention provides a compound of formula I or II, wherein t is 2.

In one aspect, the invention provides a compound of formula III:

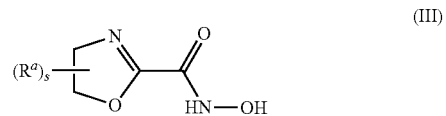

(III)

or a pharmaceutically acceptable salt, solvate, tautomer, or prodrug thereof, wherein R$^a$ is as defined for formula I and s is 0, 1, 2, 3, or 4.

In one aspect, the invention provides a compound of formula I, II, or III, wherein each R$^a$ is independently selected from halogen, CN, C(O)R$^g$, C$_1$-C$_8$ alkoxyl, NR$^h$R$^i$, SR$^j$, C$_1$-C$_8$ alkyl, C$_2$-C$_8$ alkenyl, C$_2$-C$_8$ alkynyl, (CH$_2$)$_k$—C$_3$-C$_8$ cycloalkyl, (CH$_2$)$_k$—C$_4$-C$_8$ cycloalkenyl, (CH$_2$)$_k$-3 to 10-membered saturated or unsaturated heterocyclic ring, (CH$_2$)$_k$-6 to 10-membered aromatic ring, and (CH$_2$)$_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more R$^1$, wherein R$^g$, R$^h$, R$^i$, R$^j$, R$^1$, and k are as defined for formula I.

In one aspect, the invention provides a compound of formula I, II, or III, wherein each R$^a$ is independently selected from halogen, C$_1$-C$_8$ alkyl, C$_2$-C$_8$ alkenyl, C$_2$-C$_8$ alkynyl, (CH$_2$)$_k$—C$_3$-C$_8$ cycloalkyl, (CH$_2$)$_k$—C$_4$-C$_8$ cycloalkenyl, (CH$_2$)$_k$-3 to 10-membered saturated or unsaturated heterocyclic ring, (CH$_2$)$_k$-6 to 10-membered aromatic ring, and (CH$_2$)$_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more R$^1$, wherein R$^1$ and k are as defined for formula I.

In one aspect, the invention provides a compound of formula I, II, or III, wherein each R$^a$ is independently selected from (CH$_2$)$_k$-6 to 10-membered aromatic ring and (CH$_2$)$_k$-3 to 10-membered heteroaromatic ring, wherein said aromatic ring and heteroaromatic ring are unsubstituted or substituted with one or more R$^1$, wherein R$^1$ and k are as defined for formula I.

In one aspect, the invention provides a compound, comprising a compound of formula I, II, or III, wherein each R$^a$ is independently (CH$_2$)$_k$-6 to 10-membered aromatic ring, wherein said aromatic ring is unsubstituted or substituted with one or more R$^1$, wherein R$^1$ and k are as defined for formula I. In one aspect, the invention provides a compound of formula I, II, or III, wherein R$^a$ is a phenyl ring, wherein said phenyl ring is unsubstituted or substituted with one or more R$^1$, wherein R$^1$ is as defined for formula I. In one aspect, the invention provides a compound of formula I, II, or III, wherein R$^a$ is a phenyl ring substituted with one R$^1$, wherein R$^1$ is as defined for formula I. In one aspect, the invention provides a compound of formula I, II, or III, wherein R$^1$ is OC$_1$-C$_4$ alkyl. In one aspect, the invention provides a compound of formula I, II, or III, R$^1$ is OCH$_3$. In one aspect, the invention provides a compound of formula I, II, or III, wherein R$^a$ is an unsubstituted phenyl ring.

In one aspect, the invention provides a compound of formula I, II, or III, wherein s is 0. In one aspect, the invention provides a compound of formula I, II, or III, wherein s is 1. In one aspect, the invention provides a compound of formula I, II, or III, wherein s is 2.

In one aspect, the invention provides a compound of formula IVa or IVb:

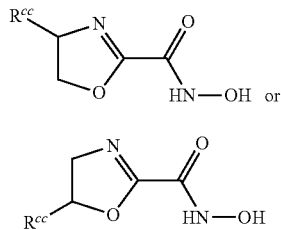

(IVa)

(IVb)

or a pharmaceutically acceptable salt, solvate, tautomer, or prodrug thereof wherein
wherein $R^{cc}$ is selected from hydrogen, halogen, CN, CF$_3$, OR$^f$, OCF$_3$, OC$_1$-C$_8$ alkyl, C(O)R$^g$, NR$^h$R$^i$, SR$^j$, C$_1$-C$_8$ alkyl, C$_2$-C$_8$ alkenyl, C$_2$-C$_8$ alkynyl, (CH$_2$)$_k$—C$_3$-C$_8$ cycloalkyl, (CH$_2$)$_k$—C$_4$-C$_8$ cycloalkenyl, (CH$_2$)$_k$-3 to 10-membered saturated or unsaturated heterocyclic ring, (CH$_2$)$_k$-6 to 10-membered aromatic ring, and (CH$_2$)$_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more R$^1$, wherein R$^1$, R$^f$, R$^g$, R$^h$, R$^i$, R$^j$, and k are as defined for formula I.

In one aspect, the invention provides a compound of formula IVa or IVb, wherein R$^{cc}$ is selected from hydrogen, halogen, C$_1$-C$_8$ alkyl, (CH$_2$)$_k$—C$_3$-C$_8$ cycloalkyl, (CH$_2$)$_k$—C$_4$-C$_8$ cycloalkenyl, (CH$_2$)$_k$-3 to 10-membered saturated or unsaturated heterocyclic ring, (CH$_2$)$_k$-6 to 10-membered aromatic ring, and (CH$_2$)$_k$-3 to 10-membered heteroaromatic ring, wherein said alkyl, cycloalkyl, cycloalkenyl, heterocyclic ring, aromatic ring and heteroaromatic ring are unsubstituted or substituted with one or more R$^1$, wherein R$^1$ and k are as defined for formula I.

In one aspect, the invention provides a compound of formula IVa or IVb, wherein R$^{cc}$ is selected from hydrogen, (CH$_2$)$_k$-6 to 10-membered aromatic ring and (CH$_2$)$_k$-3 to 10-membered heteroaromatic ring, wherein said aromatic ring and heteroaromatic ring are unsubstituted or substituted with one or more R$^1$, wherein R$^1$ and k are as defined for formula I. In one aspect, the invention provides a compound of formula IVa or IVb, wherein R$^{cc}$ is hydrogen. In one aspect, the invention provides a compound of formula IVa or IVb, wherein R$^{cc}$ is (CH$_2$)$_k$-6 to 10-membered aromatic ring, wherein said aromatic ring is unsubstituted or substituted with one or more R$^1$, wherein R$^1$ and k are as defined for formula I. In one aspect, the invention provides a compound of formula IVa or IVb, wherein R$^{cc}$ is a phenyl ring, wherein said phenyl ring is unsubstituted or substituted with one or more R$^1$, wherein R$^1$ is as defined for formula I. In one aspect, the invention provides a compound of formula IVa or IVb, wherein R$^{cc}$ is a phenyl ring, wherein said phenyl ring is substituted with one R$^1$, wherein R$^1$ is as defined for formula I. In one aspect, the invention provides a compound of formula IVa or IVb, wherein the phenyl ring is substituted with R$^1$ and R$^1$ is OC$_1$-C$_4$ alkyl. In one aspect, the invention provides a compound of formula IVa or IVb, wherein the phenyl ring is substituted with R$^1$ and R$^1$ is OCH$_3$. In one aspect, the invention provides a compound of formula IVa or IVb, wherein the R$^{cc}$ is an unsubstituted phenyl ring.

In one aspect, the invention provides a compound of formula Va, Vb, or Vc:

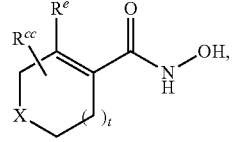

(Va)

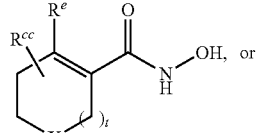

(Vb)

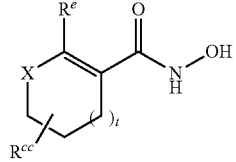

(Vc)

or a pharmaceutically acceptable salt, solvate, tautomer, or prodrug thereof, wherein
R$^{cc}$ is selected from hydrogen, halogen, CN, CF$_3$, OR$^f$, OCF$_3$, C(O)R$^g$, C$_1$-C$_8$ alkoxyl, NR$^h$R$^i$, SR$^j$, C$_1$-C$_8$ alkyl, C$_2$-C$_8$ alkenyl, C$_2$-C$_8$ alkynyl, (CH$_2$)$_k$—C$_3$-C$_8$ cycloalkyl, (CH$_2$)$_k$—C$_4$-C$_8$ cycloalkenyl, (CH$_2$)$_k$-3 to 10-membered saturated or unsaturated heterocyclic ring, (CH$_2$)$_k$-6 to 10-membered aromatic ring, and (CH$_2$)$_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more R$^1$, provided that when X is CH$_2$ and t is 1, R$^{cc}$ is not hydrogen;
t is 0, 1, or 2;
or R$^{cc}$ is attached to one of R$^b$, R$^c$, or R$^d$ to form a bridged ring;
or one of R$^b$, R$^c$, or R$^d$ is attached to R$^e$ to form a fused ring, wherein said ring is selected from C$_3$-C$_8$ cycloalkyl, C$_4$-C$_8$ cycloalkenyl, 3 to 10-membered saturated or unsaturated heterocyclic ring, 6 to 10-membered aromatic ring, and 3 to 10-membered heteroaromatic ring, further wherein said fused ring is unsubstituted or substituted with one or more R$^2$, when R$^b$ or R$^c$ is attached to R$^e$ to form said aromatic or heteroaromatic fused ring, it is understood the remaining R$^b$ or R$^e$ is absent;
or R$^{cc}$ is attached to R$^e$ to form a fused ring, wherein said ring is selected from C$_3$-C$_8$ cycloalkyl, C$_4$-C$_8$ cycloalkenyl, 3 to 10-membered saturated or unsaturated heterocyclic ring, 6 to 10-membered aromatic ring, and 3 to 10-membered heteroaromatic ring, further wherein said fused ring is unsubstituted or substituted with one or more R$^2$;
or one of R$^b$, R$^c$, or R$^d$ is attached to R$^{cc}$ form a fused ring, wherein said ring is selected from C$_3$-C$_8$ cycloalkyl, C$_4$-C$_8$ cycloalkenyl, 3 to 10-membered saturated or unsaturated heterocyclic ring, 6 to 10-membered aromatic ring, and 3 to 10-membered heteroaromatic ring, further wherein said fused ring is unsubstituted or substituted with one or more R$^2$ (when R$^b$ or R$^c$ is attached to R$^{cc}$ to form said aromatic or heteroaromatic fused ring, it is understood the remaining $R^b$ or $R^c$ is absent);

or $R^b$ and $R^c$ taken together with the carbon atom to which they are attached form a spirocyclic ring selected from $C_3$-$C_8$ cycloalkyl, $C_4$-$C_8$ cycloalkenyl, or 3 to 10-membered saturated or unsaturated heterocyclic ring, wherein said spirocyclic ring is unsubstituted or substituted with one or more $R^2$;

or $R^b$ and $R^c$ taken together with the carbon atom to which they are attached form C=O; and $R^e$, X, $R^f$, $R^g$, $R^h$, $R^i$, $R^j$, $R^v$, $R^y$, $R^{aa}$, $R^{bb}$, $R^1$, $R^2$, $R^7$, and k are as defined for formula I.

In one aspect, the invention provides a compound of formula I, Va, Vb, or Vc, wherein X is selected from $CR^bR^c$, $NR^d$, O, and $S(O)_z$, wherein $R^b$, $R^c$, $R^d$, and z are as defined for formula I. In one aspect, the invention provides a compound of formula I, Va, Vb, or Vc, wherein X is selected from $CR^bR^c$, $NR^d$, and O, wherein $R^b$, $R^c$, and $R^d$ are as defined for formula I. In one aspect, the invention provides a compound of formula I, Va, Vb, or Vc, wherein X is selected from $CR^bR^c$ and $NR^d$, wherein $R^b$, $R^c$, and $R^d$ are as defined for formula I. In one aspect, the invention provides a compound of formula I, Va, Vb, or Vc, wherein X is $CR^bR^c$, wherein $R^b$ and $R^c$ are as defined for formula I. In one aspect, the invention provides a compound of formula I, Va, Vb, or Vc, wherein X is $NR^d$, wherein $R^d$ is as defined for formula I.

In one aspect, the invention provides a compound of formula I, Va, Vb, or Vc, wherein when X is $CH_2$ and t is 1, $R^{cc}$ is not hydrogen.

In one aspect, the invention provides a compound of formula VI:

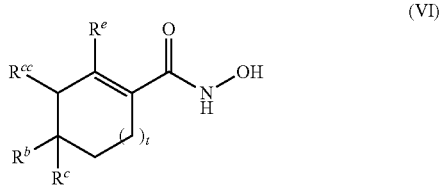

(VI)

or a pharmaceutically acceptable salt, solvate, tautomer, or prodrug thereof, wherein $R^{cc}$ is selected from hydrogen, halogen, CN, $CF_3$, $OR^f$, $OCF_3$, $C(O)R^g$, $C_1$-$C_8$ alkoxyl, $NR^hR^i$, $SR^j$, $C_1$-$C_8$ alkyl, $C_2$-$C_8$ alkenyl, $C_2$-$C_8$ alkynyl, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring, $(CH_2)_k$-6 to 10-membered aromatic ring, and $(CH_2)_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more $R^1$;

$R^b$, $R^c$, $R^e$, $R^f$, $R^g$, $R^h$, $R^i$, $R^j$, $R^1$, $R^2$, and k are as defined for formula I;

t is 0, 1, or 2, provided that when t is 1, at least one of $R^b$, $R^c$, and $R^{cc}$ is not hydrogen;

or one of $R^b$ or $R^c$ is attached to $R^{cc}$ to form a fused ring, wherein said ring is selected from $C_3$-$C_8$ cycloalkyl, $C_4$-$C_8$ cycloalkenyl, 3 to 10-membered saturated or unsaturated heterocyclic ring, 6 to 10-membered aromatic ring, and 3 to 10-membered heteroaromatic ring, further wherein said fused ring is unsubstituted or substituted with one or more $R^2$, (when $R^b$ or $R^c$ is attached to $R^{cc}$ to form said aromatic or heteroaromatic fused ring, it is understood the remaining $R^b$ or $R^c$ is absent);

or $R^{cc}$ is attached to $R^e$ to form a fused ring, wherein said ring is selected from $C_3$-$C_8$ cycloalkyl, $C_4$-$C_8$ cycloalkenyl, 3 to 10-membered saturated or unsaturated heterocyclic ring, 6 to 10-membered aromatic ring, and 3 to 10-membered heteroaromatic ring, further wherein said fused ring is unsubstituted or substituted with one or more $R^2$;

or $R^b$ and $R^c$ taken together with the carbon atom to which they are attached to form a spirocyclic ring selected from $C_3$-$C_8$ cycloalkyl, $C_4$-$C_8$ cycloalkenyl, or 3 to 10-membered saturated or unsaturated heterocyclic ring, wherein said spirocyclic ring is unsubstituted or substituted with one or more $R^2$; and or $R^b$ and $R^c$ taken together with the carbon atom to which they are attached form C=O.

In one aspect, the invention provides a compound of formula Va, Vb, Vc, or VI, wherein one of $R^b$ or $R^c$ is attached to $R^{cc}$ to form a fused ring. In one aspect, the invention provides a compound, comprising a compound of formula Va, Vb, Vc, or VI, wherein $R^{cc}$ is attached to $R^e$ to form a fused ring. In one aspect, the invention provides a compound of formula Va, Vb, Vc, or VI, wherein the fused ring is selected from $C_3$-$C_8$ cycloalkyl, 3 to 10-membered saturated or unsaturated heterocyclic ring, and 6 to 10-membered aromatic ring. In one aspect, the invention provides a compound of formula Va, Vb, Vc, or VI, wherein the fused ring is selected from $C_5$-$C_6$ cycloalkyl and 5 to 6-membered saturated or unsaturated heterocyclic ring. In one aspect, the invention provides a compound of formula Va, Vb, Vc, or VI, wherein the fused ring is $C_5$-$C_6$ cycloalkyl. In one aspect, the invention provides a compound of formula Va, Vb, Vc, or VI, wherein the fused ring is $C_5$ cycloalkyl. In one aspect, the invention provides a compound of formula Va, Vb, Vc, or VI, wherein the fused ring is $C_6$ cycloalkyl. In one aspect, the invention provides a compound of formula Va, Vb, Vc, or VI, wherein the fused ring is a 5 to 6-membered saturated heterocyclic ring. In one aspect, the invention provides a compound of formula Va, Vb, Vc, or VI, wherein the fused ring is a pyrrolidine or piperidine ring. In one aspect, the invention provides a compound of formula Va, Vb, Vc, or VI, wherein the fused ring is a pyrrolidine ring. In one aspect, the invention provides a compound of formula Va, Vb, Vc, or VI, wherein the fused ring is a piperidine ring.

In one aspect, the invention provides a compound of formula Va, Vb, Vc, or VI, wherein one of $R^b$ or $R^c$ is attached to $R^{cc}$ to form a fused ring. In one aspect, the invention provides a compound of formula Va, Vb, Vc, or VI, wherein the fused ring is a 6 to 10-membered aromatic ring. In one aspect, the invention provides a compound of formula Va, Vb, Vc, or VI, wherein the fused ring is a 6-membered aromatic ring. In one aspect, the invention provides a compound of formula Va, Vb, Vc, or VI, wherein the fused ring is a phenyl ring. In one aspect, the invention provides a compound of formula Va, Vb, Vc, or VI, wherein t is 0 or 1. In one aspect, the invention provides a compound of formula Va, Vb, Vc, or VI, wherein t is 0. In one aspect, the invention provides a compound of formula Va, Vb, Vc, or VI, wherein t is 1. In one aspect, the invention provides a compound of formula Va, Vb, Vc, or VI, wherein $R^e$ is $C_1$-$C_4$ alkyl. In one aspect, the invention provides a compound of formula Va, Vb, Vc, or VI, wherein $R^e$ is methyl.

In one aspect, the invention provides a compound of formula Va, Vb, Vc, or VI, wherein the fused ring is substituted with one or more $R^2$, and $R^2$ is selected from halogen, $C_1$-$C_4$ alkyl, and $(CH_2)_k$-6 to 10-membered aromatic ring, wherein said aromatic ring is unsubstituted or substituted with one or more $R^7$, wherein $R^7$ is as defined for formula I. In one aspect, the invention provides a compound of formula Va, Vb, Vc, or VI, wherein the fused ring is substituted with one $R^2$. In one aspect, the invention provides a compound of formula Va, Vb, Vc, or VI, wherein $R^2$ is halogen. In one aspect, the invention provides a compound of formula Va, Vb, Vc, or VI, wherein $R^2$ is $C_1$-$C_4$ alkyl. In one aspect, the invention provides a compound of formula Va, Vb, Vc, or VI, wherein $R^2$ is $CH_2$-phenyl ring, wherein said phenyl ring is substituted with one or more of $R^7$, wherein $R^7$ is as defined for formula I. In one aspect, the invention provides a compound of formula Va, Vb, Vc, or VI, wherein the phenyl ring is substituted with one $R^7$, wherein $R^7$ is as defined for formula I. In one aspect, the invention provides a compound of formula Va, Vb, Vc, or VI, wherein $R^7$ is $OC_1$-$C_4$ alkyl. In one aspect, the invention provides a compound of formula Va, Vb, Vc, or VI, wherein $R^7$ is $OCH_3$.

In one aspect, the invention provides a compound of formula I, Va, Vb, Vc, or VI, wherein $R^b$ and $R^c$ taken together with the carbon atom to which they are attached form a spirocyclic ring. In one aspect, the invention provides a compound of formula I, Va, Vb, Vc, or VI, wherein the spirocyclic ring is $C_3$-$C_8$ cycloalkyl. In one aspect, the invention provides a compound of formula I, Va, Vb, Vc, or VI, wherein the spirocyclic ring is $C_5$ cycloalkyl. In one aspect, the invention provides a compound of formula I, Va, Vb, Vc, or VI, wherein the spirocyclic ring is $C_6$ cycloalkyl. In one aspect, the invention provides a compound of formula I, Va, Vb, Vc, or VI, wherein the spirocyclic ring is unsubstituted.

In one aspect, the invention provides a compound of formula Va, Vb, Vc, or VI, wherein $R^{cc}$ is selected from hydrogen, halogen, CN, $C(O)R^g$, $C_1$-$C_8$ alkoxyl, $NR^hR^i$, $SR^j$, $C_1$-$C_8$ alkyl, $C_2$-$C_8$ alkenyl, $C_2$-$C_8$ alkynyl, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring, $(CH_2)_k$-6 to 10-membered aromatic ring, and $(CH_2)_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more $R^1$, wherein $R^1$ is as defined for formula I.

In one aspect, the invention provides a compound of formula Va, Vb, Vc, or VI, wherein $R^{cc}$ is selected from hydrogen, halogen, CN, $C(O)R^g$, $C_2$-$C_8$ alkenyl, $C_1$-$C_8$ alkoxyl, $NR^hR^i$, $SR^j$, $C_1$-$C_8$ alkyl, $(CH_2)_k$—$C_4$-$C_8$ cycloalkenyl, $(CH_2)_k$-3 to 10-membered saturated or unsaturated heterocyclic ring, $(CH_2)_k$-6 to 10-membered aromatic ring, and $(CH_2)_k$-3 to 10-membered heteroaromatic ring, wherein said alkyl, alkenyl, cycloalkenyl, heterocyclic ring, aromatic ring and heteroaromatic ring are unsubstituted or substituted with one or more $R^1$, wherein $R^1$ is as defined for formula I.

In one aspect, the invention provides a compound of formula Va, Vb, Vc, or VI, wherein $R^{cc}$ is selected from hydrogen, halogen, CN, $C_2$-$C_8$ alkenyl, $NR^hR^i$, $SR^j$, and $(CH_2)_k$-6 to 10-membered aromatic ring, wherein said alkenyl and aromatic ring are unsubstituted or substituted with one or more $R^1$, wherein $R^1$ is as defined for formula I. In one aspect, the invention provides a compound of formula Va, Vb, Vc, or VI, wherein $R^{cc}$ is hydrogen. In one aspect, the invention provides a compound of formula Va, Vb, Vc, or VI, wherein $R^{cc}$ is CN. In one aspect, the invention provides a compound of formula Va, Vb, Vc, or VI, wherein $R^{cc}$ is halogen. In one aspect, the invention provides a compound of formula Va, Vb, Vc, or VI, wherein $R^{cc}$ is bromine. In one aspect, the invention provides a compound of formula Va, Vb, Vc, or VI, wherein $R^{cc}$ is fluorine.

In one aspect, the invention provides a compound of formula Va, Vb, Vc, or VI, wherein $R^{cc}$ is selected from hydrogen, halogen, CN, $C_2$-$C_8$ alkenyl, $NR^hR^i$, $SR^j$, and $(CH_2)_k$-6 to 10-membered aromatic ring, wherein said alkenyl and aromatic ring are unsubstituted or substituted with one or more $R^1$, wherein $R^1$ is as defined for formula I. In one aspect, the invention provides a compound of formula Va, Vb, Vc, or VI, wherein $R^{cc}$ is $(CH_2)_k$-6-membered aromatic ring, wherein said aromatic ring is unsubstituted or substituted with one or more $R^1$, wherein $R^1$ is as defined for formula I. In one aspect, the invention provides a compound of formula Va, Vb, Vc, or VI, wherein $R^{cc}$ is a phenyl ring unsubstituted or substituted with one or more $R^1$, wherein $R^1$ is as defined for formula I. In one aspect, the invention provides a compound of formula Va, Vb, Vc, or VI, wherein $R^{cc}$ is a phenyl ring substituted with one $R^1$, wherein $R^1$ is as defined for formula I. In one aspect, the invention provides a compound of formula Va, Vb, Vc, or VI, wherein $R^1$ is $OC_1$-$C_4$ alkyl. In one aspect, the invention provides a compound of formula Va, Vb, Vc, or VI, wherein $R^1$ is $OCH_3$. In one aspect, the invention provides a compound of formula Va, Vb, Vc, or VI, wherein $R^{cc}$ is an unsubstituted phenyl ring.

In one aspect, the invention provides a compound of formula Va, Vb, Vc, or VI, wherein $R^{cc}$ is selected from hydrogen, halogen, CN, $C_2$-$C_8$ alkenyl, $NR^hR^i$, $SR^j$, and $(CH_2)_k$-6 to 10-membered aromatic ring, wherein said alkenyl and aromatic ring are unsubstituted or substituted with one or more $R^1$, wherein $R^1$ is as defined for formula I. In one aspect, the invention provides a compound of formula Va, Vb, Vc, or VI, wherein $R^{cc}$ is $C_2$-$C_8$ alkenyl, wherein said alkenyl is substituted with one or more $R^1$, wherein $R^1$ is as defined in formula I. In one aspect, the invention provides a compound of formula Va, Vb, Vc, or VI, wherein $R^{cc}$ is $C_2$-$C_8$ alkenyl, wherein said alkenyl is substituted with one $R^1$, wherein $R^1$ is as defined in formula I. In one aspect, the invention provides a compound of formula Va, Vb, Vc, or VI, wherein $R^1$ is selected from $C(O)NR^vR^y$ and $C(O)OR^{bb}$, wherein $R^v$, $R^y$, $R^{bb}$, and $R^1$ are as defined for formula I. In one aspect, the invention provides a compound of formula Va, Vb, Vc, or VI, wherein $R^1$ is $C(O)NR^vR^y$, wherein $R^v$, $R^y$, and $R^1$ are as defined for formula I. In one aspect, the invention provides a compound of formula Va, Vb, Vc, or VI, wherein one of $R^v$ or $R^y$ is hydrogen and the remaining $R^v$ or $R^y$ is as defined for formula I. In one aspect, the invention provides a compound of formula Va, Vb, Vc, or VI, wherein one of $R^v$ or $R^y$ is hydrogen and the remaining $R^v$ or $R^y$ is a phenyl ring, wherein said phenyl ring is unsubstituted or substituted with one or more $R^7$, wherein $R^7$ is as defined for formula I. In one aspect, the invention provides a compound of formula Va, Vb, Vc, or VI, wherein one of $R^v$ or $R^y$ is hydrogen and the remaining $R^v$ or $R^y$ is a phenyl ring, wherein said phenyl ring substituted with one $R^7$, wherein $R^7$ is as defined for formula I. In one aspect, the invention provides a compound of formula Va, Vb, Vc, or VI, wherein $R^7$ is $OC_1$-$C_4$ alkyl. In one aspect, the invention provides a compound of formula Va, Vb, Vc, or VI, wherein one of $R^v$ or $R^y$ is hydrogen and the remaining $R^v$ or $R^y$ is an unsubstituted phenyl ring. In one aspect, the invention provides a compound of formula Va, Vb, Vc, or VI, wherein $R^1$ is $C(O)OR^{bb}$, wherein $R^{bb}$ is as defined for formula I. In one aspect, the invention provides a compound of formula Va, Vb, Vc, or VI, wherein $R^{bb}$ is $C_1$-$C_8$ alkyl. In one aspect, the invention provides a compound of formula Va, Vb, Vc, or VI, wherein $R^{bb}$ is $C_1$-$C_4$ alkyl. In one aspect, the invention provides a compound of formula Va, Vb, Vc, or VI, wherein $R^{bb}$ is methyl. In one aspect, the invention provides a compound of formula Va, Vb, Vc, or VI, wherein $R^{cc}$ is $C_2$ alkenyl.

In one aspect, the invention provides a compound of formula Va, Vb, Vc, or VI, wherein $R^{cc}$ is $NR^hR^i$, wherein $R^h$ and $R^i$ are as defined for formula I. In one aspect, the invention provides a compound of formula Va, Vb, Vc, or VI, wherein $R^h$ and $R^i$ are each independently selected from hydrogen, $C(O)R^p$, $C_1$-$C_8$ alkyl, $(CH_2)_k$-6 to 10-membered aromatic ring, and $(CH_2)_k$-3 to 10-membered heteroaromatic ring, wherein said alkyl, aromatic ring, and heteroaromatic ring are unsubstituted or substituted with one or more $R^4$, wherein $R^p$, $R^4$, and k are as defined for formula I. In one aspect, the invention provides a compound of formula Va, Vb, Vc, or VI, wherein $R^h$ and $R^i$ are each independently selected from hydrogen, $C(O)R^p$, unsubstituted $C_1$-$C_8$ alkyl, and $(CH_2)_k$-6 membered aromatic ring, wherein said aromatic ring of $(CH_2)_k$-6 membered aromatic ring is unsubstituted or substituted with one or more $R^4$, wherein $R^4$ and k are as defined for formula I, wherein $R^p$ is selected from $C_1$-$C_8$ alkyl and 6 membered aromatic ring, wherein said 6 membered aromatic ring is unsubstituted or substituted with one or more $R^5$, wherein $R^5$ is as defined for formula I. In one aspect, the invention provides a compound of formula Va, Vb, Vc, or VI, wherein $R^h$ and $R^i$ are each independently selected from hydrogen, $C(O)R^p$, unsubstituted $C_1$-$C_4$ alkyl, and $(CH_2)_k$-6 membered aromatic ring, wherein said aromatic ring of $(CH_2)_k$-6 membered aromatic ring is unsubstituted or substituted with one or more $R^4$, wherein $R^4$ and k are as defined for formula I, wherein $R^p$ is selected from $C_1$-$C_4$ alkyl and 6 membered aromatic ring, wherein said 6 membered aromatic ring is unsubstituted or substituted with one or more $R^5$, wherein $R^5$ is as defined for formula I. In one aspect, the invention provides a compound of formula Va, Vb, Vc, or VI, wherein one of $R^h$ or $R^i$ is hydrogen. In one aspect, the invention provides a compound of formula Va, Vb, Vc, or VI, wherein one of $R^h$ or $R^i$ is $C(O)C_1$-$C_4$ alkyl. In one aspect, the invention provides a compound of formula Va, Vb, Vc, or VI, wherein one of $R^h$ or $R^i$ is $C(O)CH_3$. In one aspect, the invention provides a compound of formula Va, Vb, Vc, or VI, wherein one of $R^h$ or $R^i$ is $C_1$-$C_4$ alkyl. In one aspect, the invention provides a compound of formula Va, Vb, Vc, or VI, wherein one of $R^h$ or $R^i$ is methyl. In one aspect, the invention provides a compound of formula Va, Vb, Vc, or VI, wherein one of $R^h$ or $R^i$ is $C(O)$-6 membered aromatic ring, wherein said aromatic ring is substituted with one or more $R^5$, wherein $R^5$ is as defined for formula I. In one aspect, the invention provides a compound of formula Va, Vb, Vc, or VI, wherein one of $R^h$ or $R^i$ is $C(O)$-phenyl ring, wherein said phenyl ring is substituted with one or more $R^5$, wherein $R^5$ is as defined for formula I. In one aspect, the invention provides a compound of formula Va, Vb, Vc, or VI, wherein one of $R^h$ or $R^i$ is $C(O)$-phenyl ring, wherein said phenyl ring is substituted with one $R^5$, wherein $R^5$ is as defined for formula I. In one aspect, the invention provides a compound of formula Va, Vb, Vc, or VI, wherein $R^5$ is $OC_1$-$C_4$ alkyl. In one aspect, the invention provides a compound of formula Va, Vb, Vc, or VI, wherein $R^5$ is $OCH_3$. In one aspect, the invention provides a compound of formula Va, Vb, Vc, or VI, wherein one of $R^h$ or $R^i$ is $(CH_2)_k$-6 membered aromatic ring, wherein said aromatic ring is substituted with one or more $R^4$, wherein $R^4$ is as defined for formula I. In one aspect, the invention provides a compound of formula Va, Vb, Vc, or VI, wherein one of $R^h$ or $R^i$ is $(CH_2)_k$-6 membered aromatic ring, wherein said aromatic ring is substituted with one $R^4$, wherein $R^4$ is as defined for formula I. In one aspect, the invention provides a compound of formula Va, Vb, Vc, or VI, wherein $R^4$ is $OC_1$-$C_4$ alkyl. In one aspect, the invention provides a compound of formula Va, Vb, Vc, or VI, wherein $R^4$ is $OCH_3$. In one aspect, the invention provides a compound of formula Va, Vb, Vc, or VI, wherein one of $R^h$ or $R^i$ is $CH_2$-phenyl ring.

In one aspect, the invention provides a compound of formula Va, Vb, Vc, or VI, wherein one of $R^h$ or $R^i$ is selected from hydrogen, $C(O)C_1$-$C_4$ alkyl, and $C_1$-$C_4$ alkyl and the remaining $R^h$ or $R^i$ is selected from $C(O)$-6 membered aromatic ring and $(CH_2)_k$-6 membered aromatic ring, wherein said aromatic ring of $(CH_2)_k$-6 membered aromatic ring is unsubstituted or substituted with one or more $R^4$, wherein $R^4$ and k are as defined for formula I, wherein said aromatic ring of $C(O)$-6 membered aromatic ring is unsubstituted or substituted with one or more $R^5$, wherein $R^5$ is as defined for formula I. In one aspect, the invention provides a compound of formula Va, Vb, Vc, or VI, wherein one of $R^h$ or $R^i$ is hydrogen and the remaining $R^h$ or $R^i$ is $(CH_2)_k$-6 membered aromatic ring, wherein said aromatic ring is unsubstituted or substituted with one or more $R^4$, wherein $R^4$ and k are as defined for formula I. In one aspect, the invention provides a compound of formula Va, Vb, Vc, or VI, wherein one of $R^h$ or $R^i$ is $C(O)C_1$-$C_4$ alkyl and the remaining $R^h$ or $R^i$ is $(CH_2)_k$-6 membered aromatic ring, wherein said aromatic ring is unsubstituted or substituted with one or more $R^4$, wherein $R^4$ and k are as defined for formula I. In one aspect, the invention provides a compound of formula Va, Vb, Vc, or VI, wherein one of $R^h$ or $R^i$ is $C(O)CH_3$ and the remaining $R^h$ or $R^i$ is $(CH_2)_k$-6 membered aromatic ring, wherein said aromatic ring is unsubstituted or substituted with one or more $R^4$, wherein $R^4$ and k are as defined for formula I. In one aspect, the invention provides a compound of formula Va, Vb, Vc, or VI, wherein one of $R^h$ or $R^i$ is $C_1$-$C_4$ alkyl and the remaining $R^h$ or $R^i$ is $(CH_2)_k$-6 membered aromatic ring, wherein said aromatic ring is unsubstituted or substituted with one or more $R^4$, wherein $R^4$ and k are as defined for formula I. In one aspect, the invention provides a compound of formula Va, Vb, Vc, or VI, wherein one of $R^h$ or $R^i$ is methyl and the remaining $R^h$ or $R^i$ is $(CH_2)_k$-6 membered aromatic ring, wherein said aromatic ring is unsubstituted or substituted with one or more $R^4$, wherein $R^4$ and k are as defined for formula I. In one aspect, the invention provides a compound of formula Va, Vb, Vc, or VI, wherein the remaining $R^h$ or $R^i$ is $CH_2$-phenyl ring, wherein said phenyl ring is unsubstituted or substituted with one or more $R^4$, wherein $R^4$ is as defined for formula I. In one aspect, the invention provides a compound of formula Va, Vb, Vc, or VI, wherein the remaining $R^h$ or $R^i$ is $CH_2$-phenyl ring, wherein said phenyl ring is substituted with one $R^4$, wherein $R^4$ is as defined for formula I. In one aspect, the invention provides a compound of formula Va, Vb, Vc, or VI, wherein $R^4$ is $OC_1$-$C_4$ alkyl. In one aspect, the invention provides a compound of formula Va, Vb, Vc, or VI, wherein $R^4$ is $OCH_3$. In one aspect, the invention provides a compound of formula Va, Vb, Vc, or VI, wherein one of $R^h$ or $R^i$ is hydrogen and the remaining $R^h$ or $R^i$ is $C(O)$-6 membered aromatic ring, wherein said aromatic ring is unsubstituted or substituted with one or more $R^5$, wherein $R^5$ is as defined for formula I. In one aspect, the invention provides a compound of formula Va, Vb, Vc, or VI, wherein the remaining $R^h$ or $R^i$ is $C(O)$-phenyl ring, wherein said phenyl ring is unsubstituted or substituted with one or more $R^5$, wherein $R^5$ is as defined for formula I. In one aspect, the invention provides a compound of formula Va, Vb, Vc, or VI, wherein the remaining $R^h$ or $R^i$ is C(O)-phenyl ring, wherein said phenyl ring is substituted with one $R^5$, wherein $R^5$ is as defined for formula I. In one aspect, the invention provides a compound of formula Va, Vb, Vc, or VI, wherein $R^5$ is $OC_1$-$C_4$ alkyl. In one aspect, the invention provides a compound of formula Va, Vb, Vc, or VI, wherein $R^5$ is $OCH_3$.

In one aspect, the invention provides a compound of formula Va, Vb, Vc, or VI, wherein $R^{cc}$ is $SR^j$, wherein $R^j$ is as defined in formula I. In one aspect, the invention provides a compound of formula Va, Vb, Vc, or VI, wherein $R^j$ is selected from hydrogen, unsubstituted $C_1$-$C_8$ alkyl, $(CH_2)_k$-6 to 10-membered aromatic ring, and $(CH_2)_k$-3 to 10-membered heteroaromatic ring, wherein said aromatic ring and heteroaromatic ring are unsubstituted or substituted with one or more $R^4$, wherein $R^4$ and k are as defined for formula I. In one aspect, the invention provides a compound of formula Va, Vb, Vc, or VI, wherein $R^j$ is $(CH_2)_k$-6 membered aromatic ring, wherein said aromatic ring is unsubstituted or substituted with one or more $R^4$, wherein $R^4$ and k are as defined for formula I. In one aspect, the invention provides a compound of formula Va, Vb, Vc, or VI, wherein $R^j$ is a phenyl ring, wherein said phenyl ring is unsubstituted or substituted with one or more $R^4$, wherein $R^4$ is as defined in formula I. In one aspect, the invention provides a compound of formula Va, Vb, Vc, or VI, wherein $R^j$ is a phenyl ring, wherein said phenyl ring is substituted with one $R^4$, wherein $R^4$ is as defined in formula I. In one aspect, the invention provides a compound of formula Va, Vb, Vc, or VI, wherein $R^4$ is $OC_1$-$C_4$ alkyl. In one aspect, the invention provides a compound of formula Va, Vb, Vc, or VI, wherein $R^4$ is $OCH_3$. In one aspect, the invention provides a compound of formula Va, Vb, Vc, or VI, wherein $R^j$ is an unsubstituted phenyl ring.

In one aspect, the invention provides a compound of formula Va, Vb, Vc, or VI, wherein $R^b$ and $R^c$ are each hydrogen.

In one aspect, the invention provides a compound of formula Va, Vb, Vc, or VI, wherein when t is 1, at least one of $R^b$, $R^c$, and $R^{cc}$ is not hydrogen.

In one aspect, the invention provides a compound of formula VIIa or VIIb:

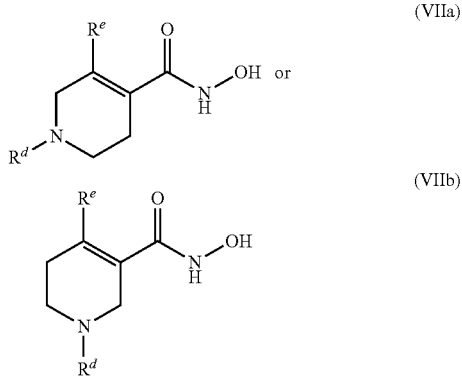

or a pharmaceutically acceptable salt, solvate, tautomer, or prodrug thereof, wherein $R^d$ and $R^e$ are as defined for formula I.

In one aspect, the invention provides a compound of formula I, Va, Vb, Vc, VIIa, or VIIb, wherein $R^d$ is selected from hydrogen, C(O)$R^g$, $C_1$-$C_8$ alkyl, S(O)$_z R^j$, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring, $(CH_2)_k$-6 to 10-membered aromatic ring, and $(CH_2)_k$-3 to 10-membered heteroaromatic ring, wherein said alkyl, cycloalkyl, cycloalkenyl, heterocyclic ring, aromatic ring and heteroaromatic ring are unsubstituted or substituted with one or more $R^1$, wherein $R^1$, $R^g$, and k are as defined for formula I.

In one aspect, the invention provides a compound of formula I, Va, Vb, Vc, VIIa, or VIIb, wherein $R^d$ is selected from C(O)$R^g$, $C_1$-$C_8$ alkyl, S(O)$_z R^j$, $(CH_2)_k$-3 to 10-membered saturated or unsaturated heterocyclic ring, $(CH_2)_k$-6 to 10-membered aromatic ring, and $(CH_2)_k$-3 to 10-membered heteroaromatic ring, wherein said alkyl, heterocyclic ring, aromatic ring and heteroaromatic ring are unsubstituted or substituted with one or more $R^1$, wherein $R^1$, $R^g$, and k are as defined for formula I.

In one aspect, the invention provides a compound of formula I, Va, Vb, Vc, VIIa, or VIIb, wherein $R^d$ is selected from C(O)$R^g$, S(O)$_z R^j$, $C_1$-$C_8$ alkyl, and $(CH_2)_k$-6 to 10-membered aromatic ring, wherein said aromatic ring is unsubstituted or substituted with one or more $R^1$, wherein $R^1$, $R^g$, and k are as defined for formula I. In one aspect, the invention provides a compound of formula I, Va, Vb, Vc, VIIa, or VIIb, wherein $R^d$ is C(O)$R^g$, wherein $R^g$ is as defined for formula I. In one aspect, the invention provides a compound of formula I, Va, Vb, Vc, VIIa, or VIIb, wherein $R^g$ is $(CH_2)_k$-6 to 10 membered aromatic ring, wherein said aromatic ring is unsubstituted or substituted with one or more $R^3$, wherein $R^3$ is as defined for formula I. In one aspect, the invention provides a compound of formula I, Va, Vb, Vc, VIIa, or VIIb, wherein $R^g$ is a phenyl ring, wherein said phenyl ring is unsubstituted or substituted with one or more $R^3$, wherein $R^3$ is as defined for formula I. In one aspect, the invention provides a compound of formula I, Va, Vb, Vc, VIIa, or VIIb, wherein $R^g$ is a phenyl ring, wherein said phenyl ring is substituted with one $R^3$, wherein $R^3$ is as defined for formula I. In one aspect, the invention provides a compound of formula I, Va, Vb, Vc, VIIa, or VIIb, wherein $R^3$ is $OC_1$-$C_4$ alkyl. In one aspect, the invention provides a compound of formula I, Va, Vb, Vc, VIIa, or VIIb, wherein $R^3$ is $OCH_3$. In one aspect, the invention provides a compound of formula I, Va, Vb, Vc, VIIa, or VIIb, wherein $R^d$ is $CH_2$-phenyl ring, wherein said phenyl ring is unsubstituted or substituted with one or more $R^1$, wherein $R^1$ is as defined for formula I. In one aspect, the invention provides a compound of formula I, Va, Vb, Vc, VIIa, or VIIb, wherein $R^d$ is $CH_2$-phenyl ring, wherein said phenyl ring is substituted with one $R^1$, wherein $R^1$ is as defined for formula I. In one aspect, the invention provides a compound of formula I, Va, Vb, Vc, VIIa, or VIIb, wherein $R^1$ is $OC_1$-$C_4$ alkyl. In one aspect, the invention provides a compound of formula I, Va, Vb, Vc, VIIa, or VIIb, wherein $R^1$ is $OCH_3$. In one aspect, the invention provides a compound of formula I, Va, Vb, Vc, VIIa, or VIIb, wherein $R^d$ is S(O)$_z R^j$, wherein $R^j$ and z are as defined for formula I. In one aspect, the invention provides a compound of formula I, Va, Vb, Vc, VIIa, or VIIb, wherein $R^j$ is $(CH_2)_k$-6 to 10 membered aromatic ring, wherein said aromatic ring is unsubstituted or substituted with one or more $R^4$, wherein $R^4$ is as defined for formula I. In one aspect, the invention provides a compound of formula I, Va, Vb, Vc, VIIa, or VIIb, wherein $R^j$ is a phenyl ring, wherein said phenyl ring is unsubstituted or substituted with one or more $R^4$, wherein $R^4$ is as defined for formula I. In one aspect, the invention provides a compound of formula I, Va, Vb, Vc, VIIa, or VIIb, wherein $R^j$ is a phenyl ring, wherein said phenyl ring is substituted with one $R^4$, wherein $R^4$ is as defined for formula I. In one aspect, the invention provides a compound of formula I, Va, Vb, Vc, VIIa, or VIIb, wherein $R^4$ is $C_1$-$C_4$ alkyl. In one aspect, the invention provides a compound of formula I, Va, Vb, Vc, VIIa, or VIIb, wherein $R^4$ is methyl. In one aspect, the invention provides a compound of formula I, Va, Vb, Vc, VIIa, or VIIb, wherein z is 2. In one aspect, the invention provides a compound of formula I, Va, Vb, Vc, VIIa, or VIIb, wherein $R^d$ is $C_1$-$C_8$ alkyl. In one aspect, the invention provides a compound of formula I, Va, Vb, Vc, VIIa, or VIIb, wherein $R^d$ is $C_1$-$C_4$ alkyl. In one aspect, the invention provides a compound of formula I, Va, Vb, Vc, VIIa, or VIIb, wherein $R^d$ is methyl.

In one aspect, the invention provides a compound of formula VIII:

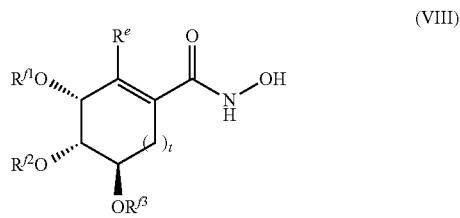

(VIII)

or a pharmaceutically acceptable salt, solvate, tautomer, or prodrug thereof, wherein each $R^{f1}$, $R^{f2}$, and $R^{f3}$ is independently selected from hydrogen, $C_1$-$C_8$ alkyl, $C_2$-$C_8$ alkenyl, $C_2$-$C_8$ alkenyl, $C_2$-$C_8$ alkynyl, $C(O)R^p$, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring, $(CH_2)_k$-6 to 10-membered aromatic ring, and $(CH_2)_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more $R^4$, wherein $R^e$, $R^p$, $R^4$, and k are as defined for formula I; and t is 0, 1, or 2.

In one aspect, the invention provides a compound of formula I and VIII, wherein each $R^{f1}$, $R^{f2}$, and $R^{f3}$ is independently selected from hydrogen, $C_1$-$C_8$ alkyl, and $C(O)R^p$, wherein $R^p$ is as defined for formula I. In one aspect, the invention provides a compound of formula I and VIII, wherein each $R^{f1}$, $R^{f2}$, and $R^{f3}$ is independently selected from hydrogen, $C_1$-$C_3$ alkyl, and $C(O)C_1$-$C_3$ alkyl. In one aspect, the invention provides a compound of formula I and VIII, wherein each $R^{f1}$, $R^{f2}$, and $R^{f3}$ is independently selected from hydrogen and methyl. In one aspect, the invention provides a compound of formula I and IX, wherein each $R^{f1}$, $R^{f2}$, and $R^{f3}$ is hydrogen.

In one aspect, the invention provides a compound of formula I, Va, Vb, Vc, VI, VIIa, VIIb, or VIII, wherein $R^e$ is selected from hydrogen, OH, and $C_1$-$C_4$ alkyl. In one aspect, the invention provides a compound of formula I, Va, Vb, Vc, VI, VIIa, VIIb, or VIII, wherein $R^e$ is hydrogen. In one aspect, the invention provides a compound of formula I, Va, Vb, Vc, VI, VIIa, VIIb, or VIII, wherein $R^e$ is OH. In one aspect, the invention provides a compound of formula I, Va, Vb, Vc, VI, VIIa, VIIb, or VIII, wherein $R^e$ is methyl.

In one aspect, the invention provides a compound of formula I, Va, Vb, Vc, VI, or VIII, wherein t is 0. In one aspect, the invention provides a compound of formula I, Va, Vb, Vc, VI, or VIII, wherein t is 1. In one aspect, the invention provides a compound of formula I, Va, Vb, Vc, VI, or VIII, wherein t is 2.

In addition to those compounds presented in the examples, the following compounds further illustrate the scope of the present invention:

TABLE 1

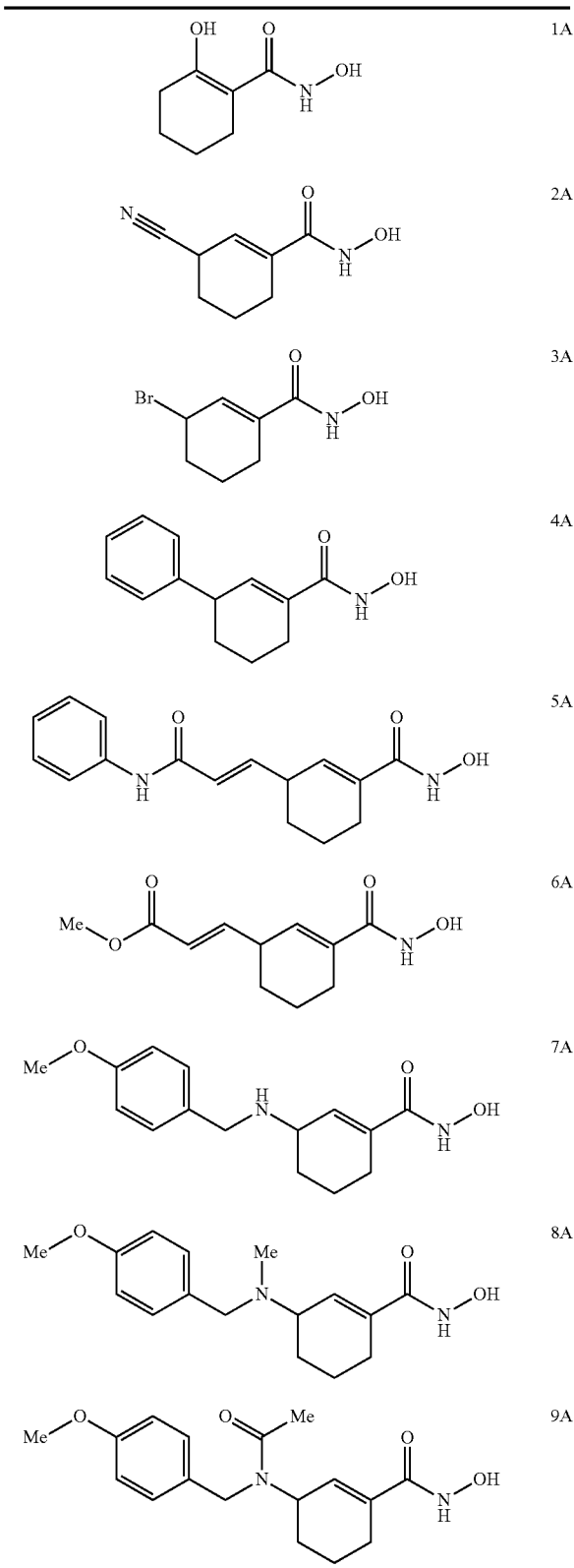

TABLE 1-continued

| Compound | No. |
|---|---|
| (phenylthio-cyclohexenyl hydroxamic acid) | 10A |
| (1-(4-methoxybenzyl)-1,2,5,6-tetrahydropyridine-3-carboxylic acid hydroxyamide) | 11A |
| (1-(4-methoxybenzoyl)-1,2,5,6-tetrahydropyridine-3-carboxylic acid hydroxyamide) | 12A |
| (1-(4-methoxybenzyl)-1,2,3,6-tetrahydropyridine-4-carboxylic acid hydroxyamide) | 13A |
| (1-(4-methoxybenzoyl)-1,2,3,6-tetrahydropyridine-4-carboxylic acid hydroxyamide) | 14A |
| (4,5-dihydrooxazole-2-carboxylic acid hydroxyamide) | 15A |
| ((S)-4-phenyl-4,5-dihydrooxazole-2-carboxylic acid hydroxyamide) | 16A |
| (cycloheptenyl hydroxamic acid) | 17A |
| (norbornenyl hydroxamic acid) | 18A |
| (cyclohexenyl hydroxamic acid) | 19A |
| (3,6-dihydro-2H-pyran-4-carboxylic acid hydroxyamide) | 20A |
| (cyclopentenyl hydroxamic acid) | 21A |
| (trihydroxy-cyclohexenyl hydroxamic acid) | 22A |
| (spiro-cyclohexenyl hydroxamic acid) | 23A |
| (2-methyl-cyclohexenyl hydroxamic acid) | 24A |
| (indanyl hydroxamic acid) | 25A |
| (octahydro-indenyl hydroxamic acid) | 26A |

TABLE 1-continued

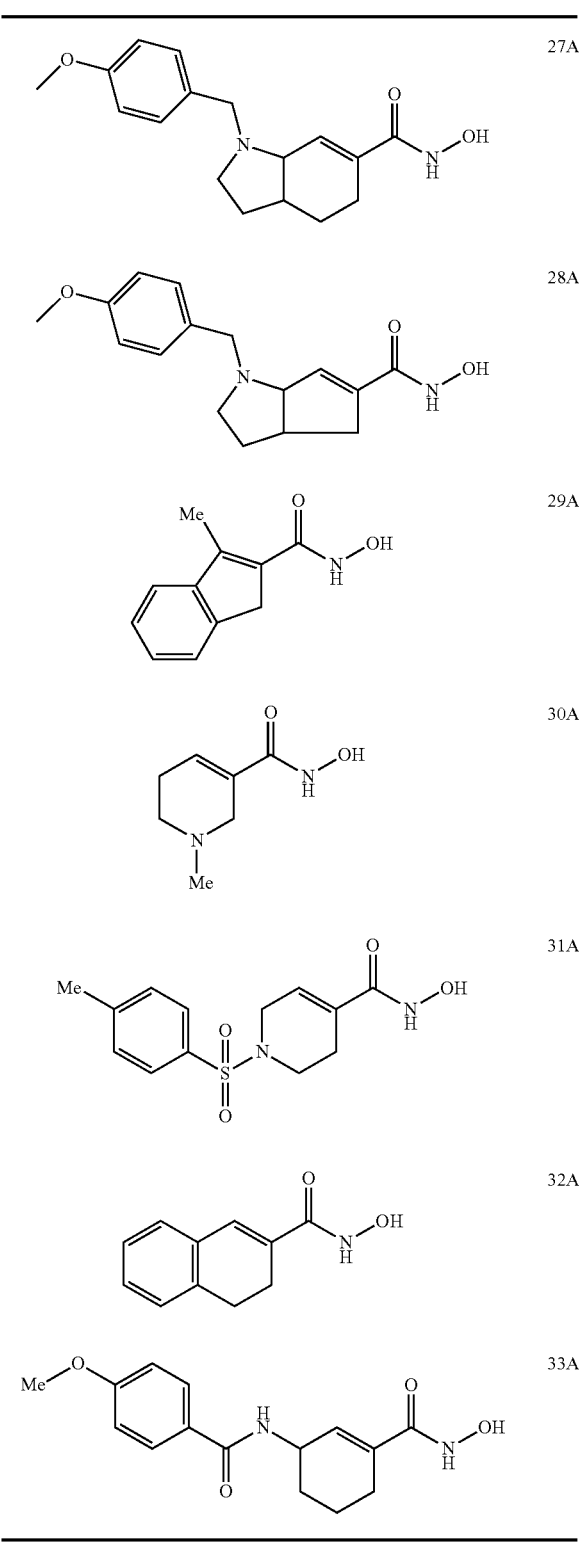

In one aspect, the subject to be administered compounds of this invention is human.

Compounds of the invention can be prepared according to methods known in the art. Schemes 1A and 2A shown below depict a general route for the preparation of compounds of the invention.

Scheme 1A

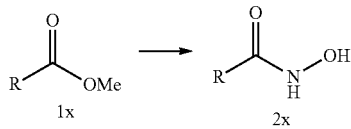

In Scheme 1A, compound 1x is treated with aqueous hydroxylamine and sodium hydroxide to give compound 2x, a compound of the invention.

Scheme 2A

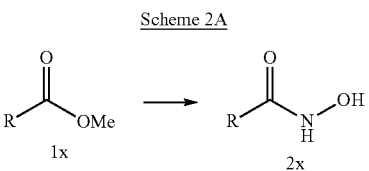

In Scheme 2A, to a solution of compound 1x, O-(tetra-hydro-2H-pyran-2-yl)hydroxylamine, 4-dimethylamin-opyridine, and $^i$Pr$_2$Net in DMF is added EDCI.HCl. After stirring overnight, the reaction mixture is subjected to standard workup conditions followed by removal of the solvent under reduced pressure. The resulting residue is redissolved in MeOH and p-toluenesulfonic acid monohydrate is added. Upon completion of the reaction, compound 2x is obtained, a compound of the invention.

Methods of the Invention

Compounds of the invention are selective inhibitors of histone deacetylases (HDAC). In one aspect, compounds of this invention inhibit HDAC 6 and/or 8. Compounds of the invention are useful in treating and/or preventing various diseases, disorders and conditions in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity), including e.g., neurological disorders (including neuropsychiatric disorders), infectious diseases, inflammatory diseases, neoplastic diseases (including cancer), metabolic diseases, autoimmune diseases and heteroimmune diseases in humans and animals.

Inhibition of Histone Deacetylase

The compounds of the present invention are useful in a variety of applications for human and animal health. The compounds of the invention are histone deacetylase (HDAC) inhibitors. A histone deacetylase inhibitor as used herein is a compound that inhibits, reduces, or otherwise modulates the activity of one or more histone deacetylase(s). HDACs catalyze the removal of acetyl groups from lysine residues on proteins, including histones. HDAC inhibitors also show diverse biological functions including effecting gene expression, cell differentiation, cell cycle progression, growth arrest, and/or apoptosis. (J. Med. Chem. 2003, 46:5097 and Curr. Med. Chem. 2003, 10:2343). HDACs have also been implicated in the control of alternative splicing such that inhibition of HDACs blocks the splicing cycle (Kuhn et al., RNA, 2009, 15:153-175). In particular, HDAC inhibition have been shown to be involved in alternative splicing (Hnilicova et al., PLoS One, 2011, 6(2): e16727., for a review of splicing see: McKay and Johnson, Mol. BioSys, 2010, 6:2093-2102.) In various embodiments, the compounds of the invention reduce HDAC activity by at least about 50%, at least about 75%, or at least about 90% or more. In further embodiments, HDAC activity is reduced by at least about 95% or at least about 99% or more.

One aspect of the invention provides a method of inhibiting histone deacetylase in a cell, comprising contacting a cell in which inhibition of histone deacetylase is desired with an inhibition effective amount of a compound of the invention or a composition thereof. Because compounds of the invention inhibit histone deacetylase(s), they are useful research tools for in vitro study of the role of histone deacetylase in biological processes. Accordingly, in one aspect of the invention, the step of contacting the cell is performed in vitro.

The term an "inhibiting effective amount" is meant to denote a dosage sufficient to cause inhibition of activity of one or more histone deacetylases in a cell, which cell can be in a unicellular or multicellular organism. The unicellular organism can be a protozoan. The multicellular organism can be a plant, a fungus, or an animal, preferably a mammal, more preferably a human. The protozoan or fungus may be infecting a plant or a mammal, preferably a human, and could therefore be located in and/or on the plant or mammal. If the histone deacetylase is in a unicellular or multicellular organism, the method according to this aspect of the invention comprises administering to the organism a compound or composition of the invention. Measurement of the effect of a compound of the invention on the enzymatic activity of a histone deacetylase is achieved using known methodologies. For example, Bradner, J. et al. Nature Chemical Biology, Vol. 6, March 2010, 238-243 and Holson, E. et al WO2012149540 (A1) Inhibitors of Histone Deacetylases.

The potential of HDAC inhibitors is tremendous, but the development of clinical compounds will likely require the design of isoform selective compounds to minimize side effect issues e.g., thrombocytopenia, fatigue, anorexia, hematological and GI-toxicity. Isoform specific HDAC inhibitors provide advantages by reducing toxicities associated with inhibition of other HDACs. Specific HDAC inhibitors provide a higher therapeutic index, resulting in better tolerance by patients during chronic or long-term treatment. While several HDAC inhibitors are now in the clinic, most of these do not show significant selectivity for individual HDAC isoforms.

HDACs are classified into four classes depending on sequence identity, domain, organization, and function. Compounds of the invention are predominately inhibitors of class I and IIb histone deacetylases. Class I enzymes (HDACs 1, 2, 3, and 8) range in size from 42-55 kDa, and are homologs of yeast Rpd3 and localize to the nucleus. Class II enzymes are further divided into class IIa (HDACs 4, 5, 7, and 9) and IIb (HDACs 6 and 10). Class II enzymes are homologs of yeast Hda1 and are found in both the nucleus and cytoplasm. The molecular weights of class II members are about twofold larger than those of the class I members. Class I enzymes are ubiquitously expressed, predominantly nuclear and mainly function as transcriptional corepressors. Class II enzyme distribution is more tissue specific, suggesting distinct functions in cellular differentiation and developmental processes.

Until now, medicinal chemists have focused on developing compounds selective for either a single isoform (e.g., selective inhibition of HDAC6, as in Wagner et al., 2013, J. Med. Chem., 56:1772-1776 or a few isoforms within the same class. For example, tubacin and tubastatin A have been used as selective HDAC 6 inhibitors (Xiong Y., et al., PNAS 110: 4604-4609 (2013)).

In some other embodiments, the compounds of the invention reduce the activity of fewer than all histone deacetylases in the cell. In certain embodiments, the compounds of the invention reduce the activity of one histone deacetylase or a sub-group of histone deacetylases to a greater extent than other histone deacetylases. In certain embodiments, the compounds of the invention reduce the activity of a sub-group of histone deacetylases (e.g., HDAC6 and HDAC8, as in Olson et al., 2013, J. Med. Chem., 56:4816-4820.) to a greater extent than other histone deacetylases. In one aspect, the compounds of the invention preferentially reduce the activity of a sub-group of histone deacetylases, the reduction in activity of each member of the sub-group may be the same or different. In another aspect, the compounds of the invention preferentially reduce the activities of more than one sub-group of histone deacetylases. In one aspect, the compounds of the invention preferentially reduce the activities of two sub-groups of histone deacetylases, the reduction in activity of each member of the two sub-groups may be the same or different. In a further aspect, the compounds of the invention preferentially reduce the activities of one histone deacetylase in one sub-group (e.g., HDAC class I) and one histone deacetylase in another sub-group (e.g., HDAC class II), the reduction in activity of each of the two histone deacetylases may be the same or different.

In certain embodiments, the present invention relates to the aforementioned compounds, wherein the compounds of the invention are selective HDAC class I inhibitors. In one aspect, a compound is a HDAC8 inhibitor. The compound may be a selective HDAC8 inhibitor. In other embodiments, the compound is a non-selective inhibitor of HDAC8.

In certain embodiments, the present invention provides the aforementioned compounds, wherein the compounds of the invention are selective HDAC class II inhibitors. In one aspect, a compound is a HDAC6 inhibitor. The compound may be a selective HDAC6 inhibitor. In other embodiments, the compound is a non-selective inhibitor of HDAC6.

In certain embodiments, the present invention provides the aforementioned compounds, wherein the compounds of the invention are both selective HDAC class I inhibitors and HDAC class II inhibitors. In one aspect, a compound is both a HDAC8 inhibitor and a HDAC6 inhibitor. The compound may be both a selective HDAC8 inhibitor and a selective HDAC6 inhibitor. In other embodiments, the compound is a non-selective inhibitor of both HDAC8 and HDAC6.

In certain embodiments, the present invention provides the aforementioned compounds, wherein the compounds of the invention are selective HDAC class I inhibitors and non-selective HDAC class II inhibitors. For example, the compounds of the invention are selective inhibitors of HDAC8 and non-selective inhibitors of HDAC6

In certain embodiments, the present invention provides the aforementioned compounds, wherein the compounds of the invention are selective HDAC class II inhibitors and non-selective HDAC class I inhibitors. For example, the compounds of the invention are selective inhibitors of HDAC6 and non-selective inhibitors of HDAC8.

In certain embodiments, the present invention provides the aforementioned compounds, wherein the compounds of the invention increase tubulin (e.g., α-tubulin) acetylation. In one aspect, the compounds of the invention are HDAC class II inhibitors (e.g., selective HDAC class II inhibitors) and increase tubulin (e.g., α-tubulin) acetylation. In a further aspect, the compounds of the invention are HDAC6 inhibitors (e.g., selective HDAC6 inhibitors) and increase tubulin (e.g., α-tubulin) acetylation. In yet another aspect, the compounds of the invention are inhibitors (e.g., selective inhibitors) of both HDAC class I and HDAC class II and increase tubulin (e.g., α-tubulin) acetylation. In a further aspect, the compounds of the invention are inhibitors (e.g., selective inhibitors) of both HDAC8 and HDAC6 and increase tubulin (e.g., α-tubulin) acetylation.

In one embodiment, a compound selective for HDAC6 will have at least about 2-fold (e.g., at least about 5-fold, 10-fold, 15-fold, or 20-fold) greater activity to inhibit HDAC6 as compared to one or more other HDACs (e.g., one or more HDACs of class I or II). In one embodiment, a compound selective for HDAC8 will have at least about 2-fold (e.g., at least about 5-fold, 10-fold, 15-fold, or 20-fold) greater activity to inhibit HDAC8 as compared to one or more other HDACs (e.g., one or more HDACs of class I or II). In one embodiment, a compound selective for HDAC6 and HDAC8 will have at least about 2-fold (e.g., at least about 5-fold, 10-fold, 15-fold, or 20-fold) greater activity to inhibit HDAC6 and HDAC8 as compared to one or more other HDACs (e.g., one or more HDACs of class I or II).

In one embodiment, a compound selectively inhibits at least one class I HDAC enzyme with an $IC_{50}$ value greater than 0.0000001 μM and less than or equal to 0.1 μM, 1 μM, 5 μM, or 30 μM. In another embodiment, a compound selectively inhibits HDAC8 with an $IC_{50}$ value greater than 0.0000001 μM and less than or equal to 0.1 μM, 1 μM, 5 μM, or 30 μM.

In one embodiment, a compound selectively inhibits at least one class II HDAC enzyme with an $IC_{50}$ value greater than 0.0000001 μM and less than or equal to 0.1 μM, 1 μM, 5 μM, or 30 μM. In another embodiment, a compound selectively inhibits HDAC6 with an $IC_{50}$ value greater than 0.0000001 μM and less than or equal to 0.1 μM, 1 μM, 5 μM, or 30 μM.

In one embodiment, a compound selectively inhibits one class I HDAC enzyme and/or one class II HDAC enzyme with an $IC_{50}$ value greater than 0.0000001 μM and less than or equal to 0.1 μM, 1 μM, 5 μM, or 30 μM. In another embodiment, a compound selectively inhibits HDAC8 and HDAC6 with an $IC_{50}$ value greater than 0.0000001 μM and less than or equal to 0.1 μM, 1 μM, 5 μM, or 30 μM.

In one embodiment, a compound of the invention is useful as a tool for probing the biological functions and relevance of the different HDAC isoforms.

Neurological Disorders

In one aspect, the invention provides methods and compositions for treating and/or preventing a neurological disorder in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity).

Recent reports have detailed the importance of histone acetylation in central nervous system ("CNS") functions such as neuronal differentiation, memory formation, drug addiction, and depression (Citrome, Psychopharmacol. Bull. 2003, 37, Suppl. 2, 74-88; Johannessen, CNS Drug Rev. 2003, 9, 199-216; Tsankova et al., 2006, Nat. Neurosci. 9, 519-525).

In one aspect, the invention provides methods and compositions for treating and/or preventing neurological disorders in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity). The term "neurological disorder" as used herein includes neurological diseases, neurodegenerative diseases and neuropsychiatric disorders. A neurological disorder is a condition having as a component a central or peripheral nervous system malfunction. Neurological disorders may cause a disturbance in the structure or function of the nervous system resulting from developmental abnormalities, disease, genetic defects, injury or toxin. These disorders may affect the central nervous system (e.g., the brain, brainstem and cerebellum), the peripheral nervous system (e.g., the cranial nerves, spinal nerves, and sympathetic and parasympathetic nervous systems) and/or the autonomic nervous system (e.g., the part of the nervous system that regulates involuntary action and that is divided into the sympathetic and parasympathetic nervous systems).

In one aspect, the invention provides methods and compositions for treating and/or preventing a disorder of the peripheral nervous system in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity). In one aspect, disorder of the peripheral nervous system is Charcot-Marie-Tooth disease. Charcot-Marie-Tooth disease refers to a group of inherited disorders collectively referred to as Charcot-Marie-Tooth disease. These neuropathies result from flaws in genes responsible for manufacturing neurons or the myelin sheath. Hallmarks of typical Charcot-Marie-Tooth disease include extreme weakening and wasting of muscles in the lower legs and feet, gait abnormalities, loss of tendon reflexes, and numbness in the lower limbs. Work with transgenic mouse models has led to the identification of histone deacetylase 6 as a potential therapeutic target for inherited peripheral neuropathies (Journal of Biochemistry & Cell Biology 44 (2012) 1299-1304).

In one aspect, the invention provides methods and compositions for treating a neurodegenerative disorder in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity). As used herein, the term "neurodegenerative disease" implies any disorder that might be reversed, deterred, managed, treated, improved, or eliminated with agents that protect or enhance the function of neurons. Examples of neurodegenerative disorders include: (i) chronic neurodegenerative diseases, such as familial and sporadic amyotrophic lateral sclerosis (FALS and ALS, respectively), familial and sporadic Parkinson's disease, Huntington's disease, familial and sporadic Alzheimer's disease, multiple sclerosis, muscular dystrophy, olivopontocerebellar atrophy, multiple system atrophy, Wilson's disease, progressive supranuclear palsy, diffuse Lewy body disease, corticodentatonigral degeneration, progressive familial myoclonic epilepsy, spinal muscular atrophy, strionigral degeneration, torsion dystonia, familial tremor, Down's Syndrome, Gilles de la Tourette syndrome, Hallervorden-Spatz disease, diabetic peripheral neuropathy, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapie, and kuru), and those caused by excess cystatin C accumulation (hereditary cystatin C angiopathy); and (ii) acute neurodegenerative disorders, such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, restless leg syndrome, vertigo as result of CNS degeneration; pathologies arising with chronic alcohol or drug abuse including, for example, the degeneration of neurons in locus coeruleus and cerebellum, drug-induced movement disorders; pathologies arising with aging including degeneration of cerebellar neurons and cortical neurons leading to cognitive and motor impairments; and pathologies arising with chronic amphetamine abuse to including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor) and Wernicke-Korsakoff's related dementia. Neurodegenerative diseases affecting sensory neurons include Friedreich's ataxia, diabetes, peripheral neuropathy, and retinal neuronal degeneration. Other neurodegenerative diseases include nerve injury or trauma associated with spinal cord injury. Neurodegenerative diseases of limbic and cortical systems include cerebral amyloidosis, Pick's atrophy, and Retts syndrome. The foregoing examples are not meant to be comprehensive but serve merely as an illustration of the term "neurodegenerative disorder."

In one aspect, compounds of the invention are useful in the treatment and/or prevention of diseases associated with aberrant protein catabolism, for example, protein degradation disorders, disorders associated with misfolded proteins, and protein deposition disorders. In certain embodiments, the compounds are useful in the treatment of the protein deposition disorders, Wilson's disease, spinocerebellar ataxia, prion disease, Parkinson's disease, Huntington's disease, amyotrophic lateral sclerosis, spinal muscular atrophy, spinal and bulbar muscular atrophy, amyloidosis, Alzheimer's disease, Alexander's diseases, alcoholic liver disease, cystic fibrosis, Pick's disease, and Lewy body dementia.

Neurodegenerative diseases that can be treated or prevented include Alzheimer's disease, Parkinson's disease, cerebral ischemia, traumatic neurodegenerative disease, Huntington's disease or chorea, senile dementia, memory disorder, vascular dementia, lesions associated with cerebral ischemia (stroke) and with cranial and medullary trauma, among others.

In one aspect, the invention provides methods of the treatment and/or prevention of a neurodegenerative disorder selected from Alzheimer's, Parkinson's, amyotrophic lateral sclerosis (ALS) and Huntington's disease. In one aspect, the neurodegenerative disorder is Alzheimer's disease. In one aspect, the neurodegenerative disorder is Parkinson's disease. In one aspect, the neurodegenerative disorder is Huntington's disease. In one aspect, the neurodegenerative disorder is amyotrophic lateral sclerosis (ALS).

In one aspect, the neurological disorder is a neuropsychiatric disorder, which refers to conditions or disorders that relate to the functioning of the brain and the cognitive processes or behavior, in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity). Neuropsychiatric disorders may be further classified based on the type of neurological disturbance affecting the mental faculties. The term "neuropsychiatric disorder," considered here as a subset of "neurological disorders," refers to a disorder which may be generally characterized by one or more breakdowns in the adaptation process. Such disorders are therefore expressed primarily in abnormalities of thought, feeling and/or behavior producing either distress or impairment of function (i.e., impairment of mental function such with dementia or senility). Currently, individuals may be evaluated for various neuropsychiatric disorders using criteria set forth in the most recent version of the American Psychiatric Association's Diagnostic and Statistical Manual of Mental Health (DSM-IV).

One group of neuropsychiatric disorders includes disorders of thinking and cognition, such as schizophrenia and delirium. A second group of neuropsychiatric disorders includes disorders of mood, such as affective disorders and anxiety. A third group of neuropsychiatric disorders includes disorders of social behavior, such as character defects and personality disorders. A fourth group of neuropsychiatric disorders includes disorders of learning, memory, and intelligence, such as mental retardation and dementia. Accordingly, neuropsychiatric disorders encompass schizophrenia, delirium, attention deficit disorder (ADD), schizoaffective disorder, Alzheimer's disease, Rubinstein-Taybi syndrome, depression, mania, attention deficit disorders, drug addiction, dementia, agitation, apathy, anxiety, psychoses, personality disorders, bipolar disorders, unipolar affective disorder, obsessive-compulsive disorders, eating disorders, post-traumatic stress disorders, irritability, adolescent conduct disorder and disinhibition. For example, HDAC inhibitors (e.g., HDAC6 and/or HDAC8 selective inhibitors) may be used in the treatment or prevention of depression (Jochems et al., Neuropsychopharmacology. 2013. doi: 10.1038/npp.2013.207.)

In one embodiment, the neurological disorder is Alzheimer's disease, Huntington's disease, seizure-induced memory loss, schizophrenia, Rubinstein Taybi syndrome, Rett Syndrome, Fragile X, Lewy body dementia, vascular dementia, ADHD, ADD, dyslexia, bipolar disorder and social, cognitive and learning disorders associated with autism, traumatic head injury, or attention deficit disorder. For example, a null mutation in HDAC6 has been shown to rescue tau mediated microtubules defects in muscles and neurons, which are known to be associated with Alzheimer's disease (Xiong et al., PNAS, 2013, 110(12):4604-9.), and HDAC6 null genotype has been shown to inhibit amyloid pathology and restore learning and memory in a mouse model for Alzheimer's disease (Govindarajan et al., EMBO Mol. Med., 2013, 5:52-63.). In one embodiment HDAC inhibitors (e.g., HDAC6 and/or HDAC8 selective inhibitors) may be used in the treatment or prevention of Alzheimer's disease.

In another embodiment, the neurological disorder is an anxiety disorder, conditioned fear response, panic disorder, obsessive compulsive disorder, post-traumatic stress disorder, phobia, social anxiety disorder, or substance dependence recovery.

In some embodiments neurological disorders are treated or prevented by decreasing the amount of DNA damage within the neuronal cell. In some embodiments neurological disorders are treated or prevented by increasing histone deacetylase activity within the neuronal cell. In some embodiments neurological disorders are treated or prevented by decreasing histone acetyl transferase activity within the neuronal cell. In some embodiments neurological disorders are treated or prevented by increasing the activity of class I histone deacetylases.

In one aspect, compounds of the invention are useful in providing neuroprotection. For example, an HDAC (e.g., HDAC6) may be involved both in the autophagy of damaged proteins, and in the modification of cellular clearance mechanisms, the latter of which results in decreased efficiency in axonal transport (d'Ydewalle et al., Traffic, 2012, 13:771-779). Compounds of the invention provide neuroprotection by inhibiting the HDAC (e.g., HDAC6), thus restoring the balance of the two functions of the HDAC. In certain aspects, compounds of the invention provide neuroprotection in a CNS injury. For example, the CNS injury is characterized or caused by oxidative stress induced neurodegeneration and/or insufficient neurite regeneration (Rivieccio et al., PNAS, 2009, 106(46):19599-604.)

Enhancing Cognitive Function

In one aspect, the invention provides methods and compositions for promoting cognitive function and enhancing learning and memory formation in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity) in both normal subjects as well as those suffering from memory loss and cognitive function disorders/impairments. A normal subject, as used herein, is a subject that has not been diagnosed with a disorder associated with impaired cognitive function. "Cognitive function" refers to mental processes of a subject relating to information gathering and/or processing; the understanding, reasoning, and/or application of information and/or ideas; the abstraction or specification of ideas and/or information; acts of creativity, problem-solving, and possibly intuition; and mental processes such as learning, perception, and/or awareness of ideas and/or information. The mental processes are distinct from those of beliefs, desires, and the like.

Memory Disorders/Impairment

Transcription is thought to be a key step for long-term memory processes (Alberini, 2009, Physiol. Rev. 89, 121-145). Transcription is promoted by specific chromatin modifications, such as histone acetylation, which modulate histone-DNA interactions (Kouzarides, 2007, Cell, 128:693-705). Modifying enzymes, such as histone acetyltransferases (HATs) and histone deacetylases (HDACs), regulate the state of acetylation on histone tails. In general, histone acetylation promotes gene expression, whereas histone deacetylation leads to gene silencing. Numerous studies have shown that a potent HAT, cAMP response element-binding protein (CREB)-binding protein (CBP), is necessary for long-lasting forms of synaptic plasticity and long term memory (for review, see Barrett, 2008, Learn Mem 15:460-467).

In contrast, HDACs have been shown to be powerful negative regulators of long-term memory processes. Nonspecific HDAC inhibitors enhance synaptic plasticity as well as long-term memory (Levenson et al., 2004, J. Biol. Chem. 279:40545-40559; Lattal et al., 2007, Behav Neurosci 121: 1125-1131; Vecsey et al., 2007, J. Neurosci 27:6128; Bredy, 2008, Learn Mem 15:460-467; Guan et al., 2009, Nature 459:55-60; Malvaez et al., 2010, Biol. Psychiatry 67:36-43; Roozendaal et al., 2010, J. Neurosci. 30:5037-5046 For example, HDAC inhibition can transform a learning event that does not lead to long-term memory into a learning event that does result in significant long-term memory (Stefanko et al., 2009, Proc. Natl. Acad. Sci. USA 106:9447-9452). Furthermore, HDAC inhibition can also generate a form of long-term memory that persists beyond the point at which normal memory fails. HDAC inhibitors have been shown to ameliorate cognitive deficits in genetic models of Alzheimer's disease (Fischer et al., 2007, Nature 447:178-182; Kilgore et al., 2010, Neuropsychopharmacology 35:870-880). These demonstrations suggest that modulating memory via HDAC inhibition have considerable therapeutic potential for many memory and cognitive disorders.

A "memory" as used herein refers to the ability to recover information about past events or knowledge. Memories include short-term memory (also referred to as working or recent memory) and long-term memory. Short-term memories involve recent events, while long-term memories relate to the recall of events of the more distant past. Methods of assessing the ability to recall a memory are known to those of skill in the art and may involve routine cognitive tests. Enhancing or retrieving memories is distinct from learning. However, in some instances in the art learning is referred to as memory. Learning, unlike memory enhancement, refers to the ability to create new memories that had not previously existed. Thus in order to test the ability of a compound to effect the ability of a subject to learn rather than recall old memories, the compound would be administered prior to or at the same time as the memory is created. In order to test the ability of a compound to affect recall of a previously created memory the compound is administered after the memory is created and preferably after the memory is lost.

As used herein "age related memory loss" refers to any of a continuum of conditions characterized by a deterioration of neurological functioning that does not rise to the level of a dementia, as further defined herein and/or as defined by the Diagnostic and Statistical Manual of Mental Disorders: 4th Edition of the American Psychiatric Association (DSM-IV, 1994). Age related memory loss is characterized by objective loss of memory in an older subject compared to his or her younger years, but cognitive test performance that is within normal limits for the subject's age. Age related memory loss subjects score within a normal range on standardized diagnostic tests for dementias, as set forth by the DSM-IV. Moreover, the DSM-IV provides separate diagnostic criteria for a condition termed Age-Related Cognitive Decline. In the context of the present invention, as well as the terms "Age-Associated Memory Impairment" and "Age-Consistent Memory Decline" are understood to be synonymous with the age related memory loss. Age-related memory loss may include decreased brain weight, gyral atrophy, ventricular dilation, and selective loss of neurons within different brain regions. For purposes of some embodiments of the present invention, more progressive forms of memory loss are also included under the definition of age-related memory disorder. Thus persons having greater than age-normal memory loss and cognitive impairment, yet scoring below the diagnostic threshold for frank dementia, may be referred to as having a mild neurocognitive disorder, mild cognitive impairment, late-life forgetfulness, benign senescent forgetfulness, incipient dementia, provisional dementia, and the like. Such subjects may be slightly more susceptible to developing frank dementia in later life (See also US patent application 2006/008517 (Vasogen Ireland limited) which is incorporated by reference). Symptoms associated with age-related memory loss include but are not limited to alterations in biochemical markers associated with the aging brain, such as IL-1 beta, IFN-gamma, p-JNK, p-ERK, reduction in synaptic activity or function, such as synaptic plasticity, evidenced by reduction in long term potentiation, diminution of memory and learning. In one embodiment, an HDAC is involved in the age related memory loss (e.g., the expression or activity of the HDAC is upregulated, or the function of the substrate is altered, for example, by changes in its post-translational modifications modulated by HDAC activity in the age related memory loss).

As used herein "injury related memory loss" refers to a loss of memory wherein there is damage to the brain, and there may have also been neurological damage. Sources of brain injury include traumatic brain injury such as concussive injuries or penetrating head wounds, brain tumors, alcoholism, Alzheimer's disease, stroke, heart attack and other conditions that deprive the brain of oxygen, meningitis, AIDS, viral encephalitis, and hydrocephalus. In one embodiment, an HDAC is involved in the injury related memory loss (e.g., the expression or activity of the HDAC is upregulated, or the function of the substrate is altered, for example, by changes in its post-translational modifications modulated by HDAC activity in the injury related memory loss).

Methods for enhancing memories can include reestablishing access to memories as well as recapturing memories. The term re-establishing access as used herein refers to increasing retrieval of a memory. Although Applicants are not bound by a mechanism of action, it is believed that the compounds of the invention are effective in increasing retrieval of memories by re-establishing a synaptic network. The process of re-establishing a synaptic network may include an increase in the number of active brain synapses and or a reversal of neuronal loss.

The invention provides methods for enhancing memory in a subject having a memory disorder in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity). Examples of types of memory disorders include Alzheimer's disease, absent-minded professor, absent-mindedness, amnesia, anterograde amnesia, blackout (alcohol-related amnesia), bromism, childhood amnesia, false memory syndrome, fugue state, hyperthymesia, Korsakoff's syndrome, lacunar amnesia, memory distrust syndrome, memory loss, post-traumatic amnesia, prosopamnesia, psychogenic amnesia, repressed memory, retrograde amnesia, Ribot's Law, selective memory loss, sywald skeid, source amnesia, source-monitoring error, the seven sins of memory, tip of the tongue, transient epileptic amnesia, transient global amnesia, and twilight sleep.

In one embodiment, Alzheimer's disease is the memory disorder. Such methods optionally involve administering the inhibitor and monitoring the subject to identify recapture of a memory that was previously lost. Subjects may be monitored by routine tests known in the art.

In other embodiments the Alzheimer's subject is one that has late stage Alzheimer's disease. Many of the drugs suggested for treating Alzheimer's disease are designed to treat the early stages of the disease by preventing plaque buildup. The compounds of the invention are useful for treating both early stages and late stages of dementia because they actually improve memory and cognition rather than preventing only plaque accumulation.

Cognitive Function Disorders/Impairment

The invention provides methods of treating and/or preventing cognitive function disorders/impairments in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity).

Impaired cognitive function refers to cognitive function that is not as robust as that observed in an age-matched normal subject and includes states in which cognitive function is reduced. In some cases, cognitive function is reduced by about 5%, about 10%, about 30%, or more, compared to cognitive function measured in an age-matched normal subject. Cognitive function may be promoted to any detectable degree, but in humans preferably is promoted sufficiently to allow an impaired subject to carry out daily activities of normal life.

In some embodiments, the cognitive function disorders or impairments in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity) are associated with, but not limited to, Alzheimer's disease, Huntington's disease, seizure induced memory loss, schizophrenia, Rubinstein Taybi syndrome, Rett Syndrome, Fragile X, Lewey body dementia, Vascular dementia, bipolar disorder and social, cognitive and learning disorders associated with autism, attention deficit hyperactivity disorder (ADHD), dyslexia, learning disorders, traumatic head injury, stroke induced cognitive and motor impairment, traumatic brain injury, neurodegeneration and neuronal loss mediated cognitive impairment, and attention deficit disorder.

In some embodiments, the cognitive function disorders or impairments are associated with, but not limited to, anxiety disorders, conditioned fear response, panic disorders, obsessive compulsive disorders, post-traumatic stress disorder, phobias, social anxiety disorders, substance dependence recovery or Age Associated Memory Impairment (AAMI), and Age Related Cognitive Decline (ARCD).

In some embodiments, the invention provides methods of treating and/or preventing vascular dementia. Vascular dementia, also referred to as "multi-infarct dementia", refers to a group of syndromes caused by different mechanisms all resulting in vascular lesions in the brain. The main subtypes of vascular dementia are, for example vascular mild cognitive impairment, multi-infarct dementia, vascular dementia due to a strategic single infarct (affecting the thalamus, the anterior cerebral artery, the parietal lobes or the cingulate gyms), vascular dementia due to hemorrhagic lesions, small vessel disease (including, e.g., vascular dementia due to lacunar lesions and Binswanger disease), and mixed Alzheimer's Disease with vascular dementia.

In some embodiments, the invention provides treating and/or preventing Huntington's disease. Huntington's disease is a neurological disease which results in cognitive decline associated with inexorable progression to death. Cognitive symptoms associated with Huntington's disease include loss of intellectual speed, attention, and short term memory and/or behavioral symptoms.

Cognitive function may be assessed, and thus optionally defined, via one or more tests or assays for cognitive function. Non-limiting examples of a test or assay for cognitive function include CANTAB (see for example Fray et al. "CANTAB battery: proposed utility in neurotoxicology." Neurotoxicol Teratol 1996; 18(4):499-504), Stroop Test, Trail Making, Wechsler Digit Span, or the CogState computerized cognitive test (see also Dehaene et al. "Reward-dependent learning in neuronal networks for planning and decision making." Brain Res. 2000; 126:21729; Iverson et al. "Interpreting change on the WAIS-III/WMS-III in clinical samples." Arch Clin Neuropsychol. 2001; 16(2):183-91; and Weaver et al. "Mild memory impairment in healthy older adults is distinct from normal aging." Cogn. 2006; 60(2):146-55). The methods of the invention may be used to promote cognitive function in a normal subject or to treat and/or prevent a subject from having a cognitive dysfunction. A normal subject, as used herein, is a subject that has not been diagnosed with a disorder associated with impaired cognitive function.

Extinction Learning Disorders

In one aspect, the invention provides methods of treating and/or preventing extinction learning disorders in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity), e.g., a fear extinction deficit.

It has been demonstrated that administration of the HDAC inhibitors sodium butyrate or trichostatin A facilitates fear extinction in mice and this enhancement mirrors that caused by commonly used behavioral manipulation and is consistent with other studies demonstrating a role for the hippocampus in the extinction of contextual fear (Lattal, et al., 2007, Behav. Neurosci. 121, 5, 1125-1131).

Compounds of the invention can be used to facilitate the psychological process of extinction learning and thus are useful for treating and/or preventing neuropsychiatric disorders and other related disorders in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity). Unlike traditional anti-anxiety drugs that are administered on a chronic basis and address physiological symptoms of anxiety, the compounds of the invention can be used on a chronic or acute basis in conjunction with a second therapy e.g., psychotherapy.

In one aspect, the present invention is directed to methods for treating and/or preventing a subject from having a neuropsychiatric disorder in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity). The methods comprise subjecting the subject to one or more sessions of a combination therapy protocol, where the combination therapy protocol comprises an acute administration of a therapeutically effective amount of a compound of the invention that enhances learning or conditioning in combination with a session of psychotherapy. By "acute administration" is intended a single exposure of the subject to the therapeutically effective amount of the compound that enhances learning or conditioning. In one aspect, the exposure to the compound occurs within about 24 hours prior to initiating the session of psychotherapy, preferably within about 12 hours, and more preferably within about 6 hours prior to initiating the session of psychotherapy. A full course of treatment for the neuropsychiatric disorder entails at least one session of this combination therapy protocol.

For purposes of the present invention, a subject may have a single disorder, or may have a constellation of disorders that are to be treated and/or prevented by the methods described herein.

The neuropsychiatric disorders contemplated in the present invention include, but are not limited to, fear and anxiety disorders, addictive disorders including substance-abuse disorders, and mood disorders. Within the fear and anxiety disorder category, the invention encompasses the treatment or prevention of panic disorder, specific phobia, post-traumatic stress disorder (PTSD), obsessive-compulsive disorder, and movement disorders such as Tourette's syndrome. The disorders contemplated herein are defined in, for example, the DSM-IV (Diagnostic and Statistical Manual of Mental Disorders (4th ed., American Psychiatric Association, Washington D.C., 1994)), which is herein incorporated by reference.

Anxiety-related disorders relate to those disorders characterized by fear, anxiety, addiction, and the like. Patients with anxiety-related disorders can have a single such disorder, or can have a constellation of disorders. The anxiety-related disorders contemplated in the present invention include, but are not limited to, anxiety disorders, addictive disorders including substance-abuse disorders, mood disorders (e.g., depression and/or bipolar disorder), movement disorders such as Tourette's syndrome, psychogenic erectile dysfunction (impotence resulting from a man's inability to obtain or maintain an erection of his penis), insomnia (e.g., chronic insomnia), and eating disorders (e.g., anorexia).

Anxiety disorders include, but are not limited to, panic disorder, agoraphobia, social phobia, specific phobia, PTSD, obsessive-compulsive disorder, and generalized anxiety disorder. The disorders contemplated herein are defined in, for example, the DSM-IV (Diagnostic and Statistical Manual of Mental Disorders (4th ed., American Psychiatric Association, Washington D.C., 1994)).

Movement disorders are neurological conditions that affect the speed, fluency, quality, and ease of movement. Representative movement disorders include but are not limited to ataxia, chorea, myoclonus, dystonia, Parkinson's disease, restless leg syndrome, tics, and Tourette's syndrome. Movement disorders typically occur as a result of damage or disease in the basal ganglia region of the brain. Movement disorders can result from age-related changes, medications, genetic disorders, metabolic disorders, disease, stroke, or injury. Recovery of movement after stroke or injury may be facilitated when treated according to the methods of the invention.

Addictive disorders are disorders characterized by addiction to an activity or substance, and include, for example, alcohol addiction, drug addiction, and gambling addiction.

Depression refers to the clinical condition known as major depressive disorder, and is characterized by a state of intense sadness, melancholia, or despair that has advanced to the point of being disruptive to an individual's social functioning and/or activities of daily living. Depression is alleviated if either (or both) the severity or frequency of a symptom of the depression is reduced. However, a subject can be treated for depression in accordance with the methods of the invention irrespective of whether the treatment actually was successful in alleviating the depression.

Insomnia is defined herein as the inability to fall asleep or to stay asleep for a sufficient amount of time during regular sleeping hours. It includes acute insomnia, which occurs in either a transient or short term form, and chronic insomnia. It also includes initial insomnia, defined as difficulty in falling asleep; middle insomnia, defined as awakening in the middle of the night followed by eventually falling back to sleep, but with difficulty; and terminal insomnia, defined as awakening before one's usual waking time and being unable to return to sleep.

As defined by the National Institute of Mental Health, Autism Spectrum Disorders (ASD), also widely known as Pervasive Developmental Disorders (PDDs), cause severe and pervasive impairment in thinking, feeling, language, and the ability to relate to others. These disorders are usually first diagnosed in early childhood and range from a severe form, called autistic disorder, through pervasive development disorder not otherwise specified (PDD-NOS), to a much milder form, Asperger syndrome. They also include two rare disorders, Rett syndrome and childhood disintegrative disorder.

Attention-Deficit Hyperactivity Disorder (ADHD) is one of the most common mental disorders that develop in children. Children with ADHD typically have impaired functioning in multiple settings, including home, school, and in relationships with peers. Symptoms of ADHD include impulsiveness, hyperactivity, and inattention.

Typical treatments encompassed by the present invention include combination therapies. For instance, the combination therapy may be a pharmacotherapy (i.e., a compound of the invention) and a behavioral therapy. Behavioral therapy comprises, but is not limited to, electroconvulsive seizure therapy, exercise, group therapy, talk therapy, or conditioning. In another embodiment, the behavioral therapy is cognitive-behavioral therapy. Examples of behavioral therapy that may be used in the ongoing methods are described, for example, in Cognitive-Behavioral Therapies by K. Dobson, ed., Guilford Publications, Inc., 2002; The new Handbook of Cognitive Therapy: Basics and Beyond by Judith S. S. Beck, Guilford Publications, Inc. 1995 herein incorporated by reference in their entireties. Any pharmaceutical active ingredient that is recognized by the skilled artisan as being a pharmacologic agent that enhances learning or conditioning can be used in the methods of the invention. For example, one such class of pharmaceutical active ingredients contemplated herein comprises compounds that increase the level of norepinephrine in the brain. Such compounds include those acting as norepinephrine reuptake inhibitors, for example tomoxetine, reboxetine, duloxetine, venlafaxine, and milnacipran, and those compounds that cause release of norepinephrine, for example amphetamine, dextroamphetamine, pemoline, and methylphenidate. Another class of such pharmaceutical active ingredients is those compounds that increase the level of acetylcholine in the brain, including, for example, compounds that block its breakdown. Examples of such compounds include, but are not limited to, donepezil HCl or Aricept™ and tacrine, which inhibit cholinesterase activity.

Methods of the invention also encompass the use in combination with a compound of the invention of any type of psychotherapy that is suitable for the particular psychiatric disorder for which the subject is undergoing treatment. Suitable methods of psychotherapy include exposure based psychotherapy, cognitive psychotherapy, and psychodynamically oriented psychotherapy. Methods of the invention also encompass exposing the subject to cognitive behavioral therapy (CBT), behavioral exposure treatments, virtual reality exposure (VRE) or cognitive remediation therapy.

Methods of the invention also encompass extinction training. The goal of extinction training is to pair a stimulus that previously provoked a deleterious, unwanted response with a new learning that will not lead to a negative outcome, thereby generating in a subject a new, more appropriate response to the stimulus to compete with and ideally replace the previous undesirable response. Extinction training frequently exposes a subject to a stimulus or situation in the absence of an aversive consequence, e.g., a subject that has deleterious, high anxiety responses to a given stimulus or situation is exposed to that stimulus or situation in the absence of an aversive consequence. A typical goal of extinction training is to produce new learning in the subject that results from the pairing of the original stimulus or situation with a non-deleterious outcome, thereby generating, in subsequent exposures to the stimulus, a more appropriate response in place of the unwanted response. An extinction learning event refers to a completed stimulus/response extinction training cycle.

One form of extinction training entails psychotherapy. For example, the methods of the invention contemplate treating and/or preventing anxiety disorders by: (i) administering psychotherapy to treat and/or prevent an anxiety-related disorder in a suitable human subject, and (ii) administering a therapeutically effective dose a compound of the invention to said subject on an achronic, post-training, pre-sleep basis. Suitable methods of psychotherapy include but are not limited to exposure-based psychotherapy, cognitive psychotherapy, and psychodynamically oriented psychotherapy.

One method of psychotherapy that is specifically contemplated is the use of virtual reality (VR) exposure therapy to treat and/or prevent an anxiety disorder using the methods of the invention.

Another method of psychotherapy that is particularly beneficial when utilized in combination with a compound or composition of the present invention is cognitive behavioral therapy ("CBT"). CBT is a form of psychotherapy that combines cognitive therapy and behavior therapy, and emphasizes the critical role of thinking in causing people to act and feel as they do. Therefore, if an individual is experiencing unwanted feelings and behaviors, CBT teaches that it is important to identify the thinking that is causing the undesirable feelings and/or behaviors and to learn how to replace this deleterious thinking with thoughts that lead to more desirable reactions. CBT is widely used to help people who are experiencing a range of mental health difficulties, some of which do not conveniently fit definitions of a particular medical affliction. CBT has been used to treat anxiety disorders, mood disorders, addictive disorders, eating disorders, insomnia, chronic pain, schizophrenia, fibromyalgia, ADHD, and autism spectrum disorders, among others. Post-extinction training pre-sleep administration of a compound of the invention, subsequent to CBT treatment, can be used to augment the effectiveness of the CBT treatment for these medical conditions.

In one embodiment, subjects suffering from social anxiety disorder undergo weekly cognitive behavioral therapy sessions to treat the affliction. After each therapy session, subjects are administered a therapeutically effective formulation of compounds of the invention on a post-extinction training pre-sleep basis. Relative to subjects treated only via cognitive behavioral therapy, or to subjects treated via cognitive behavioral therapy and a placebo, anxiety associated with social anxiety disorder is expected to be reduced to a greater extent in subjects treated with a combination of cognitive behavioral therapy and achronic administration of a compound of the invention on a post-extinction training pre-sleep basis.

In another embodiment of the invention, a compound of the invention is administered after extinction training only if the extinction training yields positive results on that day. For example, a subject undergoing cognitive behavioral therapy for PTSD is administered a compound of the invention on a post-extinction training only if the cognitive behavioral therapy was deemed to be successful, as determined by the subject and/or therapist. In one aspect, the compound is administered on a post-extinction, pre-sleep basis. In another aspect, a subject undergoing cognitive behavioral therapy for PTSD is administered a compound of the invention on a pre-extinction training. In one aspect, the compound is administered on a pre-extinction, pre-sleep basis. This method may also be useful when applied to treatment of autism spectrum disorders or attention-deficit hyperactivity disorder.

In another embodiment of the invention, subjects afflicted with anxiety disorders such as PTSD receive extinction training using Eye Movement Desensitization and Reprocessing (EMDR), and subsequently are administered a therapeutically effective dose of a compound of the invention on a post-extinction training pre-sleep basis. Another form of extinction training is provided by biofeedback, which is particularly useful in enabling subjects to learn to control physiological processes that normally occur involuntarily, such as blood pressure, heart rate, muscle tension, and skin temperature. As used herein, "biofeedback" refers to a technique in which subjects are trained to improve their health by using signals from their own bodies to control their own physiological responses.

In one embodiment of the invention, a subject suffering from chronic pain undergoes biofeedback sessions to help alleviate the pain. Upon the conclusion of each session wherein the subject has made progress in learning/developing responses that reduce the chronic pain, the subject is administered a compound of the invention on a post-extinction training pre-sleep basis in order to consolidate the desired learning.

In another embodiment, a subject suffering from phantom limb syndrome undergoes thermal biofeedback sessions to reduce and hopefully eliminate the symptoms. After each session, the subject is administered a therapeutically effective formulation of a compound of the invention on a post-extinction training pre-sleep basis.

In another embodiment, extinction training can be provided by physical therapy, or virtual reality physical therapy such as virtual reality gait therapy. For example, a stroke victim re-learning how to walk can undergo virtual reality gait therapy, and then be administered a compound of the invention on an achronic, post-extinction training pre-sleep basis.

Another form of extinction training can be provided by pharmacotherapy. For example, a man afflicted with erectile dysfunction can have an extinction learning event based on a positive sexual outcome, including instances wherein the positive sexual outcome was achieved with the pharmacological assistance of a PDE-5 inhibitor such as sildenafil, tadalafil, vardenafil, and/or udenafil. By administering a compound of the invention on a post-extinction training pre-sleep basis to a subject with erectile dysfunction, following a successful sexual outcome wherein the subject utilized sildenafil, the heightened confidence and reduced sexual performance anxiety resulting from a successful outcome can be consolidated in said subject's psyche, thereby facilitating extinction of any deleterious performance anxiety associated with sexual intercourse.

Extinction training does not always require intervention of a trained specialist. Individuals can carry out extinction training on themselves.

Infectious Disease

In one aspect, the invention provides methods and compositions for treating and/or preventing an infectious disease in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity) (e.g., fungal infections and protozoal infections).

Fungal Diseases or Infections

In some aspects, the invention provides a method for treating and/or preventing a fungal disease or infection in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity), comprising administering to a subject a compound of the invention. The invention provides a method for treating and/or preventing a hospital-acquired fungal infections that attack immunocompromised patients including those with HIV and cancer. In one embodiment, the invention provides a method for treating and/or preventing a fungal disease in a subject not suffering from cancer.

Protozoal Infections

In some aspects, the invention provides a method for treating and/or preventing a protozoal infection in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity), comprising administering to a subject a compound of the invention. The invention provides a method for treating and/or preventing a protozoal infection. A protozoal infection may be caused by an infection from an organism including, but not limited to, *Entamoeba histolytica*, *Toxoplasma gondii*, *Schistosoma mansoni*, *Cryptosporidium* sp., *Leishmania donovani*, *Neospora caninum*, and *Plasmodium* spp. In one embodiment, the invention provides a method for treating and/or preventing malaria.

Inflammatory Disease

In some aspects, the invention provides a method for treating, and/or preventing an inflammatory disease in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity), including but not limited to stroke, rheumatoid arthritis, lupus erythematosus, ulcerative colitis, traumatic brain injuries, osteoarthritis, septic arthritis, gout, pseudogout, juvenile arthritis, Still's disease, ankylosing spondylitis, Henoch-Schonlein purpura, psoriatic arthritis, reactive arthritis (Reiter's syndrome), hemochromatosis, hepatitis, Wegener's granulomatosis, TRAPS (TNF-alpha receptor associated periodic fever syndrome), inflammatory bowel disease, Crohn's Disease, recurrent fever, anemia, leukocytosis, asthma, chronic obstructive pulmonary disease, myalgia, Adult Still's disease, lupus arthritis, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis, allergic contact dermatitis, urticarial dermatitis, psoriasis, eczema and related conditions, insect bites, erythroderma, mycosis fungoides and related conditions, pyoderma gangrenosum, erythema multiforme, rosacea, onychomycosis, and acne and related conditions.

In some aspects, the methods described herein are used to treat an inflammatory skin condition in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity). Inflammatory skin conditions are those conditions of the skin in which inflammatory cells (e.g., polymorphonuclear neutrophils and lymphocytes) infiltrate the skin with no overt or known infectious etiology. Symptoms of inflammatory skin conditions generally include erythema (redness), edema (swelling), pain, pruritus, increased surface temperature and loss of function. As used herein, inflammatory skin conditions include, but are not limited to, allergic contact dermatitis, urticarial dermatitis, psoriasis, eczema and related conditions, insect bites, erythroderma, mycosis fungoides and related conditions, pyoderma gangrenosum, erythema multiforme, rosacea, onychomycosis, and acne and related conditions, but excluding psoriasis and its related conditions.

Autoimmune Disease

In some aspects, the invention provides a method for treating and/or preventing an autoimmune disease in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity), including but not limited to arthritis, psoriatic arthritis, osteoarthritis, Still's disease, juvenile arthritis, lupus, diabetes (type I or type II), myasthenia gravis, Hashimoto's thyroiditis, Ord's thyroiditis, Graves' disease, Sjogren's syndrome, multiple sclerosis, Guillain-Barre syndrome, acute disseminated encephalomyelitis, Addison's disease, opsoclonusmyoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behget's disease, chronic fatigue, dysautonomia, endometriosis, interstitial cystitis, neuromyotonia, and vulvodynia.

In some aspects, compounds of the invention are used to treat and/or prevent diseases or conditions that are mediated or linked to T-cell dysregulation. Inhibition of HDAC6 has been found to enhance Treg function and restore immune homeostasis. HDAC inhibitors have been implicated in treatment of colitis and allograft rejection as HDAC6 inhibition has been shown to enhance Treg mediated immunosuppresion (Kalin and Bergman, 2013, J. Med. Chem., DOI: 10.1021/jm4001659). HDAC inhibitors may have broad treatment potential as anti-inflammatory and immunosuppressive agents (Hancock et al., 2012, Ann. Rheum. Dis., (Supp II): i46-i54.). Non-limiting examples of disease that may be mediated or linked to T-cell deregulation include arthritis (e.g., rheumatoid arthritis and juvenile idiopathic arthritis), colitis, allograft rejection, lupus, asthma, psoriasis, inflammation, allergy, allergic encephalomyelitis, autoimmune lymphoproliferative disorder, autoimmune polyglandular syndrome type II, type I diabetes, lymphomas (e.g., T-cell lymphoma and lymphoid interstitial lymphoma), Wiskott-Aldrich syndrome, myasthenia gravis, and infectious diseases (e.g., HIV, *H. pylori* infection, hepatitis B infection, and hepatitis C infection).

In some aspects, a compound of the invention is used to treat and/or prevent diseases or conditions that are mediated or linked to IL-Ib secretion and activity e.g., autoimmune diseases or conditions in which IL-Ib is contributor to the signs and symptoms of the diseases or conditions (Burger et al., Best Practice & Research Clinical Rheumatology, Vol. 20, No. 5, pp. 879-896, 2006; Dayer et al., Current Opinions in Rheum., 2001, 13:170-176; Abramson et al., Rheumatology, 2002; 41; 972-980). A compound of the invention may be used to inhibit IL-Ib secretion and thus find utility in the treatment of diseases or conditions that are linked to IL-Ib secretion and activity, which include, but are not limited to, osteoarthritis, rheumatoid arthritis, septic arthritis, gout, pseudogout, juvenile arthritis, Still's disease, ankylosing spondylitis, systemic lupus erythematosus (SLE), Henoch-Schonlein purpura, psoriatic arthritis, reactive arthritis (Reiter's syndrome), hemochromatosis, hepatitis, Wegener's granulomatosis, Familial Mediterranean fever (FMF), HIDS (hyperimmunoglobulinemia D and periodic fever syndrome), TRAPS (TNF-alpha receptor associated periodic fever syndrome), inflammatory bowel disease, Crohn's Disease, ulcerative colitis, recurrent fever, anemia, leukocytosis, asthma, chronic obstructive pulmonary disease, myalgia.

Heteroimmune Conditions or Disease

In some aspects, the invention provides a method for treating and/or preventing a heteroimmune condition or disease in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity). A heteroimmune condition or disease is when an immune response occurs in response to an exogenous antigen (e.g., drugs or pathogens). Heteroimmune conditions or diseases include but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some aspects, the invention provides a method related to organ transplant rejection in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity). In one aspect, the transplant organ is any organ. In one aspect, the organ is selected from heart, kidney, eye, liver, lung, pancreas, intestine, and thymus.

Neoplastic Disease

In some aspects, the invention provides methods of selectively inducing terminal differentiation, and arresting cell growth and/or apoptosis of neoplastic cells, thereby inhibiting proliferation of such cells. In some aspects, the invention provides methods treating and/preventing a neoplastic disease in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity). The compounds of the present invention are useful in treating and/or preventing cancer in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity) in a subject. The utility of HDAC inhibitors in the treatment of cancer is reviewed in Acharya et al., 2005, Mol. Pharm. 68 (4): 917-932.

The term "cancer" refers to any cancer caused by the proliferation of neoplastic cells, such as solid tumors, neoplasms, carcinomas, sarcomas, leukemias, lymphomas and the like. In particular, cancers that may be treated and/or prevented by the compounds of the invention include, but are not limited to: cardiac cancer, lung cancer, gastrointestinal cancer, genitourinary tract cancer, liver cancer, nervous system cancer, gynecological cancer, hematologic cancer, skin cancer, ovarian cancer and adrenal gland cancer.

In some embodiments, the compounds of the invention relate to treating or preventing cardiac cancers selected from sarcoma (angiosarcoma, fibrosarcoma, rhabdomyosarcoma, liposarcoma), myxoma, rhabdomyoma, fibroma, lipoma and teratoma.

In some embodiments, the compounds of the invention relate to treating or preventing lung cancer selected from bronchogenic carcinoma (squamous cell, undifferentiated small cell, undifferentiated large cell, adenocarcinoma), alveolar (bronchiolar) carcinoma, bronchial adenoma, sarcoma, chondromatous hamartoma, and mesothelioma.

In some embodiments, the compounds of the invention relate to treating or preventing gastrointestinal cancer selected from esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), and large bowel (adenocarcinoma, tubular adenoma, villous adenoma, hamartoma, leiomyoma).

In some embodiments, the compounds of the invention relate to treating and/or preventing genitourinary tract cancer selected from kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

In some embodiments, the compounds of the invention relate to treating and/or preventing liver cancer selected from hepatoma (hepatocellular carcinoma), cholangiocarcinoma, hepatoblastoma, angiosarcoma, hepatocellular adenoma, and hemangioma.

In some embodiments, the compounds of the invention relate to treating and/or preventing bone cancer selected from osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors. In some embodiments, the compounds of the invention relate to treating, and/or preventing multiple myeloma.

In some embodiments, the compounds of the invention relate to treating and/or preventing nervous system cancer selected from skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), and spinal cord (neurofibroma, meningioma, glioma, sarcoma).

In some embodiments, the compounds of the invention relate to treating, and/or preventing gynecological cancer selected from uterus (endometrial carcinoma, uterine clear cell carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma, ovarian clear cell carcinoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

In some embodiments, the compounds of the invention relate to treating and/or preventing skin cancer selected from malignant melanoma, basal cell carcinoma, squamous cell carcinoma, Karposi's sarcoma, moles dysplastic nevi, lipoma, angioma, dermatofibroma, keloids, and psoriasis.

In some embodiments, the compounds of the invention are useful in the treatment of breast cancer. In some embodiments, the compounds of the invention useful in the treatment of breast cancer are selective for, or more greatly inhibit, HDAC1, 6 and/or 8, or subsets thereof. HDAC1, 6 and 8 are more highly expressed in a highly metatstic breast cancer cell line and HDAC1, 6 and 8 are involved in invasion of breast cancer cells (Park et al., 2011, Oncology Reports, 25: 1677-1681).

In some embodiments, the compounds are useful in the treatment and/or preventing of cancers that include, but are not limited to: leukemias including acute leukemias and chronic leukemias such as acute lymphocytic leukemia (ALL), Acute myeloid leukemia (AML), chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; mesothelioma, primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genito urinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer. In some embodiments, the compounds are useful in the treating and/or prevention of breast cancer.

In some embodiments, the compounds of the invention are useful for treating and/or preventing T-cell lymphoma. In some embodiments, the T-cell lymphoma is T cell lymphoblastic leukemia/lymphoma.

In some embodiments, the compounds of the invention are useful for treating and/or preventing neuroblastoma.

Neuroblastoma is a form of cancer that originates from nerve cells. Sometimes, this cancer can form in your adrenal gland (located above your kidneys), stomach, chest and/or pelvis. Typically, neuroblastoma affects children 5 or younger. It is the most prevalent cancer found in infants. In some embodiments, the compounds of the invention relate to methods of treating and/or preventing adrenal gland cancer selected from adrenal neuroblastoma. In some embodiments, compounds of the invention that inhibit the function of HDAC8 are useful for treating or preventing neuroblastoma as high expression of HDAC8 is associated with poor prognosis in conjunction with neuroblastoma (Oehme et al., 2009, Clin. Cancer. Res. 15:91-99.). In some embodiments, compounds of the invention that selectively inhibit the function of HDAC8 are useful for treating or preventing neuroblastoma. In some embodiments, compounds of the invention that inhibit HDAC8 to a greater extent than other subclasses of HDACs are useful for treating or preventing neuroblastoma.

In some embodiments, the compounds of the inventions are useful for treating and/or preventing clear cell carcinoma. Clear cell carcinoma is a type of adenocarcinoma. Clear cell carcinomas include, but are not limited to: uterine clear cell carcinoma, ovarian clear cell carcinoma, vaginal clear cell carcinoma, clear cell carcinoma of the lung, clear cell squamous cell carcinoma of the lung, clear cell adenocarcinoma of the lung. In some embodiments, the compounds of the invention relate to methods of treating and/or preventing clear cell carcinoma.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

Hemagologicl Diseases

In some aspects, the invention provides methods of treating or preventing hematolical diseases in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity). Hematologic diseases include abnormal growth of blood cells which can lead to dysplastic changes in blood cells and hematologic malignancies such as various leukemias. Examples of hematologic diseases include but are not limited to acute myeloid leukemia, acute promyelocytic leukemia, acute lymphoblastic leukemia, chronic myelogenous leukemia, the myelodysplastic syndromes, and sickle cell anemia. In some aspect, the invention provides methods of treating and/or preventing a leukemia.

Acute myeloid leukemia (AML) is the most common type of acute leukemia that occurs in adults. Several inherited genetic disorders and immunodeficiency states are associated with an increased risk of AML. These include disorders with defects in DNA stability, leading to random chormosomal breakage, such as Bloom's syndrome, Fanconi's anemia, Li-Fraumeni kindreds, ataxia-telangiectasia, and X-linked agammaglobulinemia.

Acute promyelocytic leukemia (APML) represents a distinct subgroup of AML. This subtype is characterized by promyelocytic blasts containing the 15;17 chromosomal translocation. This translocation leads to the generation of the fusion transcript comprised of the retinoic acid receptor and a sequence PML.

Acute lymphoblastic leukemia (ALL) is a heterogenerous disease with distinct clinical features displayed by various subtypes. Reoccurring cytogenetic abnormalities have been demonstrated in ALL. The most common cytogenetic abnormality is the 9;22 translocation. The resultant Philadelphia chromosome represents poor prognosis of the patient.

Chronic myelogenous leukemia (CML) is a clonal myeloproliferative disorder of a pluripotent stem cell. CML is characterized by a specific chromosomal abnormality involving the translocation of chromosomes 9 and 22, creating the Philadelphia chromosome. Ionizing radiation is associated with the development of CML.

The myelodysplastic syndromes (MDS) are heterogeneous clonal hematopoietic stem cell disorders grouped together because of the presence of dysplastic changes in one or more of the hematopoietic lineages including dysplastic changes in the myeloid, erythroid, and megakaryocytic series. These changes result in cytopenias in one or more of the three lineages. Patients afflicted with MDS typically develop complications related to anemia, neutropenia (infections), or thrombocytopenia (bleeding). Generally, from about 10% to about 70% of patients with MDS develop acute leukemia.

Sickle cell disease is attributable to homozygous inheritance of a single amino acid substitution in the β-globin gene that leads to polymerization of deoxygenated hemoglobin, deformation of red blood cells, microvascular occlusion, hemolysis, and consequent disease manifestations, including pain, strokes, and pulmonary complications (Bunn H F, 1997, J. Med. 337:762-769). Abundant biochemical, epidemiological, and clinical evidence have shown that a high level of γ globin, the fetal form of β globin, inhibits the aberrant polymerization of sickle hemoglobin and ameliorates the disease phenotype. The only Food and Drug Administration (FDA)-approved drug for sickle cell disease, hydroxyurea, causes significant induction of fetal hemoglobin, decreased disease severity, and benefits overall mortality (Letvin et al., 1984, N Engl J Med 310:869-873; Platt O S, et al., 1984, J Clin Invest 74:652-656; Charache S, et al., 1995, N Engl J. Med 332: 317-1322; Steinberg M H, et al., 2003, JAMA 289:1645-1651). Nevertheless, hydroxyurea has bone marrow-suppressive effects and is ineffective in a significant portion of patients (Charache S, et al.; Steinberg M H, et al., 2003; Steinberg M H, 1999, N Engl J. Med 340:1021-1030). A drug that induces fetal hemoglobin more substantially with less myelosuppression would be expected to have greater therapeutic utility in sickle cell disease.

Transcriptional regulation of the human globin gene locus has been investigated intensively. Gamma-globin gene expression is influenced by transcription factors (GATA-1, EKLF, NF-E4p22, Ikaros) and chromatin modifying enzymes [SWI/SNF complex, HATs, and histone deacetylase (HDACs)] as part of multiprotein complexes, and a unique, dynamic chromatin structure termed the β-globin active chromatin hub (βACH) (8-11). Polymorphisms in BCL11A, a transcriptional repressor, alter baseline fetal hemoglobin levels, and a multiprotein complex containing BCL11a binds to the β-globin locus, resulting in repression of γ-globin expression (Menzel S, et al., 2007, Nat Genet 39:1197-1199; Lettre G, et al., 2008, Proc Natl Acad Sci USA 105:11869-11874; Sankaran V G, et al., 2008, Science 322:1839-1842; Uda M, et al., 2008, Proc NATL Acad Sci USA 105:1620-1625; Sankaran V G, et al., 2009, Nature 460:1093-1097). Despite this granularity, discrete targets amenable to ligand discovery efforts have not been identified and functionally validated.

Other Conditions, Diseases or Disorders

In some aspects, the invention provides methods of treating and/or preventing other conditions, diseases, or disorders in which an HDAC (e.g., HDAC class I (e.g., HDAC8) and/or HDAC class II (e.g., HDAC6)) is involved (e.g., the expression or activity of the HDAC is upregulated, or the function of the substrate is altered, for example, by changes in its post-translational modifications modulated by HDAC activity).

In one aspect, the disorder is muscle atrophy. In one aspect, the disorder is polycycstic ovarian syndrome. In one aspect, the disorder is male pattern baldness. In one aspect, the disorder is uterine fibroids. In one aspect, the disorder is endometriosis.

Formulations

The compounds of the invention may be administered alone (e.g., in saline or buffer) or using any delivery vehicles known in the art. For instance the following delivery vehicles have been described: Cochleates; Emulsomes, ISCOMs; Liposomes; Live bacterial vectors (e.g., *Salmonella, Escherichia coli, Bacillus* calmatte-guerin, *Shigella, Lactobacillus*); Live viral vectors (e.g., Vaccinia, adenovirus, Herpes Simplex); Microspheres; Nucleic acid vaccines; Polymers; Polymer rings; Proteosomes; Sodium Fluoride; Transgenic plants; Virosomes; Virus-like particles. Other delivery vehicles are known in the art and some additional examples are provided below.

The term an "effective amount" of a compound of the invention refers to the amount necessary or sufficient to realize a desired biologic effect. For example, an effective amount of a compound of the invention is that amount sufficient to treat a condition. In another aspect, an effective amount of a compound iss that amount sufficient to prevent a condition. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the condition being treated, the particular compounds being administered the size of the subject, or the severity of the condition.

The compounds of the invention may be administered by any route known, such as, for example, orally, transdermally, intravenously, cutaneously, subcutaneously, nasally, intramuscularly, intraperitoneally, intracranially, and intracerebroventricularly.

In certain embodiments, compounds of the invention are administered at dosage levels greater than about 0.001 mg/kg, such as greater than about 0.01 mg/kg or greater than about 0.1 mg/kg. For example, the dosage level may be from about 0.001 mg/kg to about 50 mg/kg such as from about 0.01 mg/kg to about 25 mg/kg, from about 0.1 mg/kg to about 10 mg/kg, or from about 1 mg/kg to about 5 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can also be administered to a subject.

In one embodiment, the compound of the invention is administered once-daily, twice-daily, or three-times daily. In one embodiment, the compound of the invention is administered continuously (i.e., every day) or intermittently (e.g., 3-5 days a week). In another embodiment, administration could be on an intermittent schedule.

Further, administration less frequently than daily, such as, for example, every other day may be chosen. In additional embodiments, administration with at least 2 days between doses may be chosen. By way of example only, dosing may be every third day, bi-weekly or weekly. As another example, a single, acute dose may be administered. Alternatively, compounds of the invention can be administered on a non-regular basis e.g., whenever symptoms begin. For any compound described herein the effective amount can be initially determined from animal models.

Toxicity and efficacy of the compounds of the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage of the compounds of the invention for use in humans. The dosage of such agents lies preferably within a range of circulating concentrations that include the ED50 with little or no toxicity. The dosage may vary within this range depending upon the dosage form employed and the route of administration utilized. For any compound used in the method of the invention, the effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography. In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Multiple doses of the compounds of the invention are also contemplated.

The formulations of the invention are administered in pharmaceutically acceptable solutions, which may routinely contain pharmaceutically acceptable concentrations of salt, buffering agents, preservatives, compatible carriers, and optionally other therapeutic ingredients.

For use in therapy, an effective amount of one or more compounds of the invention can be administered to a subject by any mode that delivers the compound(s) to the desired surface, e.g., mucosal, systemic. Administering the pharmaceutical composition of the present invention may be accomplished by any means known to the skilled artisan. Compounds of the invention may be administered orally, transdermally, intravenously, cutaneously, subcutaneously, nasally, intramuscularly, intraperitoneally, intracranially, or intracerebroventricularly.

For oral administration, one or more compounds of the invention can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated.

Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of one or more compounds of the invention. The compound(s) may be chemically modified so that oral delivery of the derivative is efficacious. Generally, the chemical modification contemplated is the attachment of at least one moiety to the compound itself, where said moiety permits (a) inhibition of proteolysis; and (b) uptake into the blood stream from the stomach or intestine. Also desired is the increase in overall stability of the compound(s) and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4: 185-189. Other polymers that could be used are poly-1,3-dioxolane and poly-1,3,6-tioxocane. Preferred for pharmaceutical usage, as indicated above, are polyethylene glycol moieties.

The location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound or by release of the biologically active material beyond the stomach environment, such as in the intestine.

To ensure full gastric resistance a coating impermeable to at least pH 5.0 is important. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The compound of the invention can be included in the formulation as fine multiparticulates in the form of granules or pellets of particle size about 1 mm. The formulation of the material for capsule administration could also be as a powder, lightly compressed plugs or even as tablets. The compound of the invention could be prepared by compression.

Colorants and flavoring agents may all be included. For example, the compound of the invention may be formulated (such as by liposome or microsphere encapsulation) and then further contained within an edible product, such as a refrigerated beverage containing colorants and flavoring agents.

One may dilute or increase the volume of compound delivered with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell. Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants is the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the compound of the invention to prevent sticking during the formulation process. Lubricants may be used as a layer between the compound and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000. Glidants that might improve the flow properties of the drug during formulation and to aid rearrangement during compression might be added. The glidants may include starch, talc, pyrogenic silica and hydrated silicoaluminate.

To aid dissolution of the compound into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

Also contemplated herein is pulmonary delivery of the compounds of the invention. The compound is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63: 135-144 (leuprolide acetate); Braquet et al., 1989, Journal of Cardiovascular Pharmacology, 13(suppl. 5): 143-146 (endothelin-1); Hubbard et al., 1989, Annals of Internal Medicine, Vol. IJJ, pp. 206-212 (al-antitrypsin); Smith et al., 1989, J. Clin. Invest. 84: 1 145-1 146 (a-1-proteinase); Oswein et al., 1990, "Aerosolization of Proteins", Proceedings of Symposium on Respiratory Drug Delivery II, Keystone, Colorado, March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of compound. Typically, each formulation is specific to the type of device employed and may involve the use of an appropriate propellant material, in addition to the usual diluents, and/or carriers useful in therapy. Also, the use of liposomes, microcapsules or microspheres, inclusion complexes, or other types of carriers is contemplated. Chemically modified compound may also be prepared in different formulations depending on the type of chemical modification or the type of device employed. Formulations suitable for use with a nebulizer, either jet or ultrasonic, will typically comprise compound dissolved in water at a concentration of about 0.1 to 25 mg of biologically active compound per mL of solution. The formulation may also include a buffer and a simple sugar (e.g., for stabilization and regulation of osmotic pressure). The nebulizer formulation may also contain a surfactant, to reduce or prevent surface induced aggregation of the compound caused by atomization of the solution in forming the aerosol.

Formulations for use with a metered-dose inhaler device will generally comprise a finely divided powder containing the compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifiuoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound and may also include a bulking agent, such as lactose, sorbitol, sucrose, or mannitol in amounts which facilitate dispersal of the powder from the device, e.g., 50 to 90% by weight of the formulation. The compound should most advantageously be prepared in particulate form with an average particle size of less than 10 mm (or microns), most preferably 0.5 to 5 mm, for most effective delivery to the distal lung.

Nasal delivery of a compound of the invention is also contemplated. Nasal delivery allows the passage of a compound of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compound, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions.

Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249: 1527-1533, 1990, which is incorporated herein by reference.

The compounds of the invention may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a compound of the invention optionally included in a pharmaceutically acceptable carrier. The term pharmaceutically acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the invention, and with each other, in a manner such that there is no interaction which would substantially impair the desired pharmaceutical efficiency.

The compounds of the invention may be delivered to the brain using a formulation capable of delivering a compound across the blood brain barrier. One obstacle to delivering compounds to the brain is the physiology and structure of the brain. The blood-brain barrier is made up of specialized capillaries lined with a single layer of endothelial cells. The region between cells is sealed with a tight junction, so the only access to the brain from the blood is through the endothelial cells. The barrier allows only certain substances, such as lipophilic molecules through and keeps other harmful compounds and pathogens out. Thus, lipophilic carriers are useful for delivering non-lipohilic compounds to the brain. For instance, DHA, a fatty acid naturally occurring in the human brain has been found to be useful for delivering drugs covalently attached thereto to the brain (Such as those described in U.S. Pat. No. 6,407,137). U.S. Pat. No. 5,525,727 describes a dihydropyridine pyridinium salt carrier redox system for the specific and sustained delivery of drug species to the brain. U.S. Pat. No. 5,618,803 describes targeted drug delivery with phosphonate derivatives. U.S. Pat. No. 7,119,074 describes amphiphilic prodrugs of a therapeutic compound conjugated to an PEG-oligomer/polymer for delivering the compound across the blood brain barrier. The compounds described herein may be modified by covalent attachment to a lipophilic carrier or co-formulation with a lipophilic carrier. Others are known to those of skill in the art.

The compounds of the invention may be delivered with other methods for enhancing memory retrieval or treating other symptoms or causes of disorders associated with the memory loss. For instance, environmental enrichment (EE) has been used for enhancing memories. EE involves creating a stimulating environment around a subject. Other therapeutics may also be combined to treat the underlying disorder or to enhance memory.

Combination Therapies

As used herein, "combination therapy" or "co-therapy" includes the administration of a compound of the present invention, or a pharmaceutically acceptable salt, prodrug, or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In one aspect, the combination therapies comprise administering one or more compounds of the invention in combination with one or more inhibitors of histone deacetylases other than the compounds of the invention selected from phenyl acetate, phenylbutyrate, valproic acid and AN-9, SAHA, m-carboxycinnamic acid bishydroxamic acid, suberic bishydroxamic acid, pyroxamide, TSA, oxamflatin, and NVP-LAQ824, TPX, AOE, and depudecin, apicidin, FK-228, and FR901228, MS-275 and CI-994, CHAPs, scriptaid, tubacin, JNJ16241199, A-161906, 6-(3-chlorophenylureido)caproic hydroxamic acid, and PXD101.

In one aspect the combination therapies comprise administering one or more compounds of the invention in combination one or more of the following: DNA methyltransferase inhibitors (e.g., 5-aza-2'deoxycitidine), tamoxifen, phenylbutyrate, compounds that target chromatin DNA (e.g., etoposide, camptothecin, cisplatin, doxorubicin, 5-fluoruracil, cyclophosphamide, ellipcitine), topoisomerase II inhibitors, tyrosine kinase inhibitors (e.g., imatinib mesylate, arsenic trioxide), proteasome inhibitors (e.g., bortezomib, Epoxomicin, lactacystin, MG132, MG341, MG115, XAV939, TMC-95 A-D, Disulfiram, Epigallocatechin-3-gallate, carfilzomib, 3,3'-Diamino-4'-methoxyflavone, AdaAhx$_3$L$_3$VS, AdaLys(Bio)Ahx$_3$L$_3$VS, ALLN, Anaphase- Promoting Complex Inhibitor Negative Control, Anaphase-Promoting Complex Inhibitor, Celastrol, clasto-Lactacystin β-Lactone, DUB Inhibitor IV, DUB Inhibitor V, and DUB Inhibitor VI), and all-trans-retinoic acid (HDAC inhibitor combination therapies for cancer reviewed in Acharya et al., 2005, Mol. Pharm. 68 (4): 917-932). In some embodiments, compounds of the present invention used in combination therapy are selective HDAC inhibitors. In some embodiments, a compound of the present invention is a selective HDAC inhibitor and is used in combination with anticancer agents including: paclitaxel, etoposide, doxorubicin, SAHA (suberoylanilide hydroxamic acid), bortezomib or subsets thereof (Namdar et al., 2010, PNAS, 107(46):20003-20008).

The invention includes combination therapies including the methods of treating and/or preventing a condition described herein. Combination therapy includes administering one or more compounds of the invention in combination with one or more pharmaceutically active ingredients or exposing the subject to cognitive behavioral therapy (CBT), psychotherapy, behavioral exposure treatments, virtual reality exposure (VRE) or cognitive remediation therapy. In one aspect, the combination therapy is a dual therapy. In one aspect, the combination therapy is a triple therapy.

In one aspect, the combination therapy is for a method of treating or preventing a neurological disorder. In one aspect, the combination therapy is for methods of treating or preventing Alzheimer's disease. The combination therapies comprise the administration of an effective amount of one or more (e.g., one) compounds of the invention and the administration of an effective amount of one or more (e.g., one) other pharmaceutically active ingredients (e.g., drugs). The compounds of the invention and the other pharmaceutically active ingredients can be administered separately (i.e., each is in its own separate dosage form), or the compounds of the invention can be combined with the other pharmaceutically active ingredients in the same dosage form.

Pharmaceutically active ingredients that are useful in combination therapies of the invention include e.g., BACE inhibitors (beta secretase inhibitors), muscarinic antagonists, cholinesterase inhibitors (e.g., acetyl- and/or butyrylcholinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; GABA inverse agonists; inhibitors of amyloid aggregation; glycogen synthase kinase beta inhibitors; tau kinase inhibitors (e.g., GSK3beta inhibitors, cdk5 inhibitors, ERK inhibitors), promoters of alpha secretase activity; PDE-10 inhibitors and cholesterol absorption inhibitors. Further examples of pharmaceutically active ingredients that are useful for combination therapies of the invention are (+)-2,3-dihydro-5,6-dimethoxy-2-[[1-(phenylmethyl)-4-piperidinyl]methy-1]-1H-inden-1-one hydrochloride, i.e., donepezil hydrochloride, available as the Aricept™ brand of donepezil hydrochloride, Exelon (rivastigmine), Cognex (tacrine), anti-Abeta vaccine (active immunization), amyloid precursor protein (APP) ligands, agents that upregulate insulin degrading enzyme and/or neprilysin, cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe, fibrates (for example, clofibrate, Clofibride, Etofibrate, Aluminium Clofibrate), LXR agonists, LRP mimics, 5-HT6 receptor antagonists, nicotinic receptor agonists, H3 receptor antagonists, other histone deacetylase inhibitors, hsp90 inhibitors, muscarinic receptor agonists, 5-HT6 receptor antagonists mGluR1 or mGluR5 positive allosteric modulators or agonists, mGluR2/3 antagonists, anti-inflammatory agents that can reduce neuroinflammation, prostaglandin EP2 receptor antagonists, PAI-1 inhibitors and agents that can induce Abeta efflux such as gelsolin.

Examples of combination therapies of the compounds of the invention with other pharmaceutically active ingredients include combinations with: anti-Alzheimer's agents, beta-secretase inhibitors, gamma-secretase inhibitors, HMG-CoA reductase inhibitors, NSAID's including ibuprofen, N-methyl-D-aspartate (NMDA) receptor antagonists, such as memantine, cholinesterase inhibitors such as galantamine, rivastigmine, donepezil, and tacrine, vitamin E, CB-I receptor antagonists or CB-I receptor inverse agonists, antibiotics such as doxycycline and rifampin, anti-amyloid antibodies, or other pharmaceutically active ingredients that affect receptors or enzymes that either increase the efficacy, safety, convenience, or reduce unwanted side effects or toxicity of the compounds of the invention. The compounds of the invention may also be delivered in a cocktail of multiple HDAC inhibitors. Combination therapies of the invention may be in either unit dose or kit form.

The compounds of the invention are also useful in combination with known pharmaceutically active ingredients such as anti-cancer agents for the treatment and/or prevention of cancer. Combinations of the compounds of the invention with other anti-cancer or chemotherapeutic agents are within the scope of the invention. Examples of such agents can be found in Cancer Principles and Practice of Oncology by V. T. Devita and S. Hellman (editors), 6.sup.th edition (Feb. 15, 2001), Lippincott Williams & Wilkins Publishers. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents, agents that interfere with cell cycle checkpoints, agents that interfere with receptor tyrosine kinases (RTKs) and cancer vaccines. The compounds of the invention are particularly useful when co-administered with radiation therapy.

In some embodiments, the compounds of the invention are useful for the treatment and/or prevention of multiple myeloma in combination with a proteasome inhibitor. In some embodiments, the proteasome inhibitor is bortezomib.

In some embodiments, the compounds of the invention are also useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

Additional combination therapies are discussed herein under the extinction learning section.

The invention also includes articles, which refers to any one or collection of components. In some embodiments the articles are kits. The articles include pharmaceutical or diagnostic grade compounds of the invention in one or more containers. The article may include instructions or labels promoting or describing the use of the compounds of the invention.

Compounds of the invention can be evaluated using a variety of methods known in the art. For example, the following methods can be used to evaluate compounds of the invention: the inhibition of HDAC activity can be determined using a trypsin-coupled protocol and/or a non-trypsin-coupled Caliper protocol (Schultz, B. E. Biochemistry, 2004, 43, 11083 and U.S. patent application Ser. No. 61/628,562 entitled "Fluorescent Substrates for Determining Lysine Deacetylase Activity" filed Nov. 2, 2011); the inhibition of HDAC activity can be determined using various cells suitable for determing HDAC inhibition, e.g., HeLa cells; mass spectrometry can be used to identify changes in histone acetylation and methylation states induced in various types of cells (e.g., neuron cells) by treatment with the compounds; the identification of gene expression changes upon treatment with compounds of the invention in various types cells (e.g., neuron cells) can be determined using RNA for transcript profile analysis on Illumina microarrays; and the ability of the compounds to selectively inhibit HDACs6/8 to effect unique conformational changes in the enzymes induced by assembly into these multi-protein complexes can be evaluated by immunoprecipitating HDAC6/8 complexes from mouse forebrain and by determining the presence and activity of complex members (e.g., CoREST, mSin3a, and Mta3) using in vitro assays.

The following Examples are illustrative and should not be interpreted in any way so as to limit the scope of the invention.

EXAMPLES

Compounds of the invention are prepared according to methods exemplified below:

Example 1

N-Hydroxy-1-Methyl-1,2,5,6-Tetrahydropyridine-3-Carboxamide (30A)

Method A:

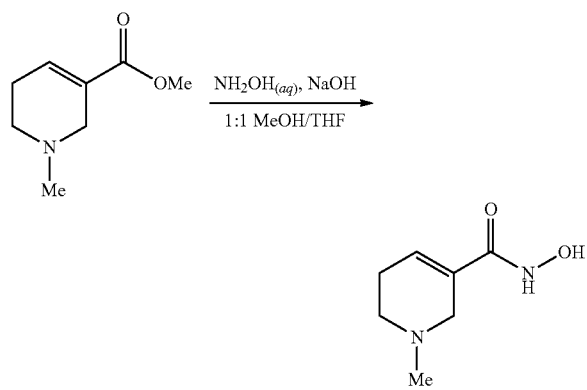

To a solution of methyl 1-methyl-1,2,5,6-tetrahydropyridine-3-carboxylate hydrochloride (0.70 g, 0.45 mmol) in 2 mL of a 1:1 mixture of THF/MeOH was added 50% aqueous hydroxylamine (0.884 mL, 14.43 mmol, 32 equiv) and solid sodium hydroxide (0.09 g, 2.25 mmol, 5 equiv). The reaction was stirred at room temperature for 3 h. After completion, the reaction was diluted in water and the remaining methanol and THF were removed under reduced pressure. The pH was adjusted to 7 with 1N HCl$_{(aq)}$, and the solvent was removed under reduced pressure. Purification using reverse-phase flash chromatography afforded 0.025 g of N-hydroxy-1-methyl-1,2,5,6-tetrahydropyridine-3-carboxamide (Yield=35%).

$^1$H NMR (300 MHz, CD$_3$OD) δ 6.63 (s 1H), 4.17 (d, 1H, J=15.4 Hz), 3.76 (d, 1H, J=15.4 Hz), 3.65-3.50 (m, 1H), 3.27-3.11 (m, 1H), 2.99 (s, 3H), 2.71-2.56 (m, 2H); HPLC purity (UV/Vis)>99.0%. ESI+MS: m/z 157.2 ([M+H]$^+$).

Example 2

N-Hydroxycyclohex-1-Enecarboxamide (19A)

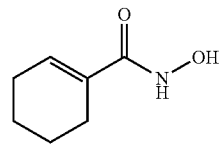

(19A)

Compound 19A was synthesized by subjecting methyl cyclohex-1-enecarboxylate to Method A.

$^1$H NMR (300 MHz, d$^6$-DMSO) δ 10.50 (br s, 1H), 8.75 (brs, 1H), 6.40 (br s, 1H), 2.15-2.05 (m, 4H), 1.63-1.47 (m, 4H); $^{13}$C NMR (300 MHz, d$^6$-DMSO) δ 165.8, 131.5, 131.4, 24.6, 23.7, 21.7, 21.3; HRMS (ES$^+$) calcd for C$_7$H$_{11}$NO$_2$H 142.0823 found 142.0864; HPLC purity (UV/Vis)>99.0%.

Example 3

N-Hydroxy-3,6-Dihydro-2H-Pyran-4-Carboxamide (20A)

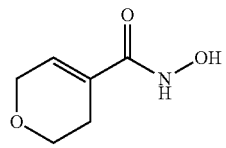

(20A)

Compound 20A was synthesized by subjecting methyl 3,6-dihydro-2H-pyran-4-carboxylate to Method A.

$^1$H NMR (300 mHz, d$^6$-DMSO) δ 10.65 (br s, 1H), 6.46 (s, 1H), 4.13 (m, 2H), 3.67 (t, 2H, J=5.4 Hz), 2.20 (m, 2H); $^{13}$C NMR (300 MHz, d$^6$-DMSO) δ 164.2, 130.6, 128.9, 64.5, 63.3, 24.2. ESI+MS: m/z 144.3 ([M+H]$^+$).

Example 4

N-Hydroxycyclopent-1-Enecarboxamide (21A)

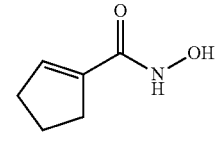

(21A)

Compound 21A was synthesized by subjecting methyl cyclopent-1-enecarboxylate to Method A.

¹H NMR (300 MHz, DMSO) δ 10.50 (br s, 1H), 8.80 (br s, 1H) 6.39 (s, 1H), 2.50-2.25 (m, 4H), 1.90-1.70 (m, 2H); ¹³C NMR (300 MHz, d⁶-DMSO) δ 162.4, 137.2, 136.0, 32.5, 31.2, 22.6; HRMS (ES⁺) calcd for $C_6H_9NO_2H$ 128.0667 found 128.0708; HPLC purity (UV/Vis)>99.0%.

Example 5

(3R,4S,5R)-N,3,4,5-Tetrahydroxycyclohex-1-En-ecarboxamide (22A)

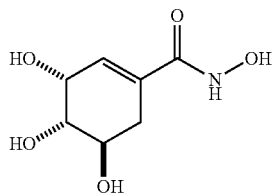
(22A)

Compound 22A was synthesized by subjecting (3R,4S,5R)-methyl 3,4,5-trihydroxycyclohex-1-enecarboxylate to Method A.

¹H NMR (300 MHz, D₂O) δ 6.33 (m, 1H), 4.37 (t, 1H, J=3.9 Hz), 3.99 (m, 1H), 3.72 (dd, 1H, J=8.6, 4.2 Hz), 2.68 (dd, 1H, J=17.6, 5.3 Hz), 2.17 (dd, 1H, J=17.6, 6.7 Hz); HPLC purity (UV/Vis)>99.0%. ESI+MS: m/z 212.2 ([M+Na]⁺)

Example 6

N-Hydroxy-3-((4-Methoxybenzyl)Amino)Cyclohex-1-Enecarboxamide (7A)

Method B:

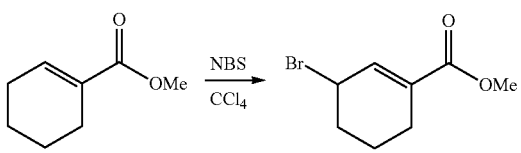

To a solution of methyl cyclohex-1-enecarboxylate (2.00 g, 14.3 mmol) in 21 mL of carbon tetrachloride was added N-bromosuccinamide (2.54 g, 14.3 mmol, 1.00 equiv). The reaction was heated to reflux and stirred for 4 h. Upon completion, the reaction mixture was filtered and the filter cake was rinsed with additional cold carbon tetrachloride. The filtrate was concentrated under reduced pressure, and the resulting residue was purified by flash chromatography to afford methyl 3-bromocyclohex-1-enecarboxylate (0.240 g, 7% yield).

Method C:

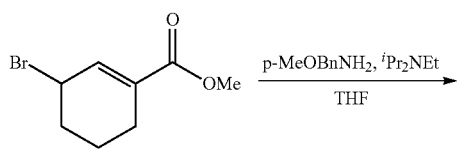

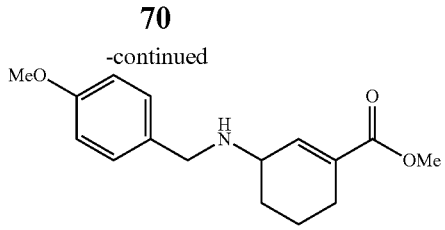

A solution of methyl 3-bromocyclohex-1-enecarboxylate (0.200 g, 0.910 mmol) (synthesized by Method B) and ⁱPr₂Net (52.0 mL, 3.01 mmol, 3.30 equiv) in 2.00 mL of THF was added dropwise to a solution of p-MeOBnNH₂ (0.375 g, 2.74 mmol, 3.00 equiv) in 2.5 mL of THF. The reaction was initially stirred at room temperature for 30 min and then stirred at 65° C. for 16 h. The reaction was diluted with saturated NaHCO₃₍ₐq₎ and extracted with EtOAc. The combined organic extracts were dried with Na₂SO₄, filtered, and concentrated under reduced pressure. The resulting residue was purified by flash chromatography to afford methyl 3-((4-methoxybenzyl)amino)cyclohex-1-enecarboxylate (0.112 g, 44% yield).

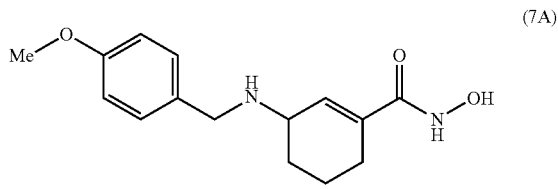 [SMILES: COc1ccc(CNC2C=C(C(=O)NO)CCC2)cc1]
(7A)

Compound 7A was synthesized by subjecting 3-((4-methoxybenzyl)amino)cyclohex-1-enecarboxylate to Method A.

¹H NMR (300 MHz, CD₃OD) δ 7.43 (d, 2H, J=8.6 Hz), 7.00 (d, 2H, J=8.6 Hz), 6.54 (br s, 1H), 4.23 (s, 2H), 4.00 (br s, 1H), 3.81 (s, 3H), 2.36-2.27 (m, 2H), 2.25-2.15 (m, 1H), 2.02-1.95 (m, 1H), 1.78-1.65 (m, 2H); HPLC purity (UV/Vis)>99.0%. ESI+MS: m/z 276.3 ([M+H]⁺).

Example 7

N-Hydroxy-3-(Phenylthio)Cyclohex-1-Enecarboxamide (10A)

Method D:

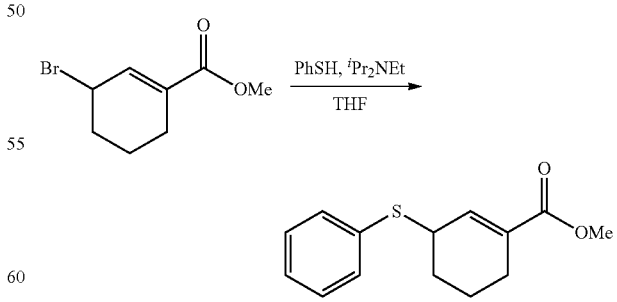

To a solution of methyl 3-bromocyclohex-1-enecarboxylate (0.050 g, 0.23 mmol) (synthesized by Method B) and K₂CO₃ (0.035 g, 0.25 mmol, 1.1 equiv) in 1.0 mL of DMF was added benzenethiol (0.23 mL, 2.3 mmol, 10 equiv), and the reaction was stirred at room temperature for 30 mins.

Upon completion, the reaction mixture was diluted with saturated NaHCO$_{3(aq)}$ and extracted with EtOAc. The combined organic extracts were dried with Na$_2$SO$_4$, filtered, and concentrated under reduced pressure. The resulting residue was purified by flash chromatography to afford methyl 3-(phenylthio)cyclohex-1-enecarboxylate (0.040 g, 70% yield).

(10A)

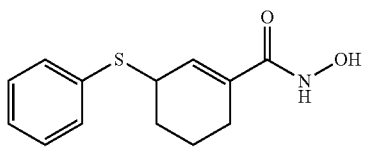

Compound 10A was synthesized by subjecting methyl 3-(phenylthio)cyclohex-1-enecarboxylate (synthesized by Method D) to Method A with the following modifications. The aqueous phase was extracted with EtOAc subsequent to neutralization. The combined organic extracts were dried with Na$_2$SO$_4$, filtered, and concentrated under reduced pressure. The resulting residue was purified by preparatory HPLC to afford the desired compound (52% yield).

$^1$H NMR (300 MHz, CD$_3$OD) δ 7.46-7.42 (m, 2H), 7.36-7.21 (m, 4H), 6.53-6.49 (m, 1H), 4.00-3.92 (m, 1H), 2.26-2.08 (m 2H), 1.96-1.85 (m, 2H), 1.77-1.64 (m, 2H); HPLC purity (UV/Vis)>99.0%. ESI+MS: m/z 250.2 ([M+H]$^+$).

Example 8

N-(3-(Hydroxycarbamoyl)Cyclohex-2-En-1-Yl)-4-Methoxybenzamide (33A)

Method E:

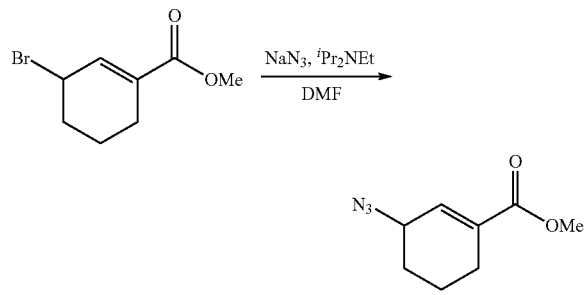

A solution of methyl 3-bromocyclohex-1-enecarboxylate (0.410 g, 1.87 mmol) (synthesized by Method B) in 5.30 mL of DMF was cooled to 0° C. before the addition of NaN$_3$ (0.146 g, 2.24 mmol, 1.20 equiv). The reaction was stirred for 1 h at 0° C. and for 2 h at room temperature. The reaction mixture was diluted with EtOAc and washed with water. The organic phase was dried with Na$_2$SO$_4$, filtered, and concentrated under reduced pressure to afford methyl 3-azidocyclohex-1-enecarboxylate, which was used without further purification.

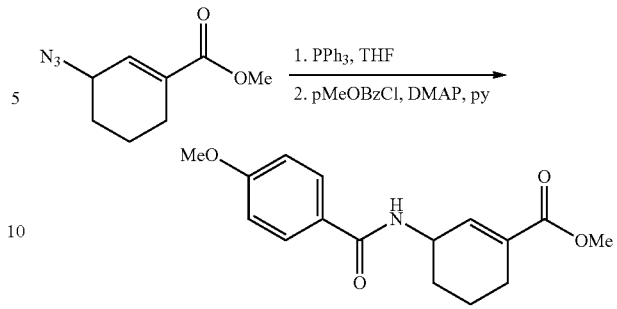

To a solution of methyl 3-azidocyclohex-1-enecarboxylate (0.090 g, 0.50 mmol) in 7.5 mL of THF was added PPh$_3$ (0.26 g, 1.0 mmol, 2.0 equiv) and a few drops of water. The reaction was heated to 60° C. and stirred for 16 h. After cooling to room temperature, the reaction mixture was concentrated and redissolved in 1.6 mL of pyridine. Then, 4-dimethylaminopyridine (0.006 g, 0.05 mmol, 0.1 equiv) was added followed by the dropwise addition of pMeOBzCl (0.067 mL, 0.5 mmol, 1.0 equiv). The reaction was stirred at room temperature for 4 h, diluted in EtOAc, and washed with 1N HCl$_{(aq)}$. The organic phase was dried with Na$_2$SO$_4$, filtered, and concentrated under reduced pressure. The resulting residue was purified by flash chromatography to afford methyl 3-(4-methoxybenzamido)cyclohex-1-enecarboxylate (0.03 g, 21% yield).

(33A)

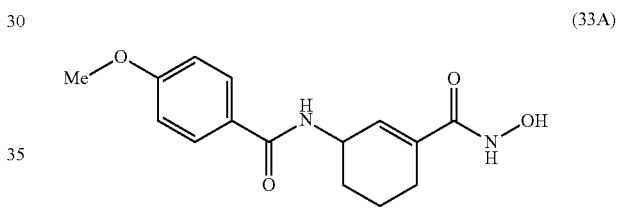

Compound 33A was synthesized by subjecting methyl 3-(4-methoxybenzamido)cyclohex-1-enecarboxylate to Method A with the following modifications. The aqueous phase was extracted with EtOAc subsequent to neutralization. The combined organic extracts were dried with Na$_2$SO$_4$, filtered, and concentrated under reduced pressure to afford a sample of the desired compound deemed sufficiently pure (0.015 g, 75%).

$^1$H NMR (300 MHz, DMSO-d$_6$) δ 10.63 (s, 1H), 8.79 (s, 1H), 7.56 (d, 2H, J=8.8 Hz), 6.98 (d, 2H, J=8.8 Hz), 6.28 (br s, 1H), 4.65-4.54 (m, 1H), 3.80 (s, 3H), 3.32 (s, 1H), 2.19-2.10 (m, 2H), 1.88-1.77 (m, 2H), 1.64-1.46 (m, 2H); HPLC purity (UV/Vis)=90.9%. ESI+MS: m/z 291.2 ([M+H]$^+$).

Example 9

N-Hydroxy-3,4-Dihydronaphthalene-2-Carboxamide (32A)

Method F:

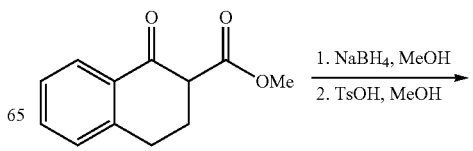

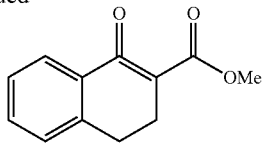

A solution of methyl 1-oxo-1,2,3,4-tetrahydronaphthalene-2-carboxylate (0.200 g, 0.980 mmol) in 3.00 mL of MeOH was cooled to 0° C. before the slow addition of NaBH$_4$ (0.041 g, 1.07 mmol, 1.1 equiv). The reaction was stirred for 30 min, diluted in MeOH, washed with saturated NH$_4$Cl$_{(aq)}$. The organic phase was dried with Na$_2$SO$_4$, filtered, and concentrated under reduced pressure. The resulting residue was redissolved in MeOH, and p-toluenesulfonic acid monohydrate (0.167 g, 0.980, 1.00 equiv) was added. The reaction mixture was heated to 60° C., stirred for 2 h, and concentrated under reduced pressure. The resulting residue was purified by flash chromatography to afford methyl 3,4-dihydronaphthalene-2-carboxylate (0.020 g, 10% yield).

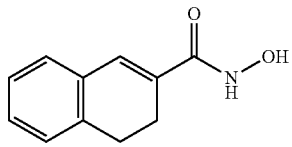

(32A)

Compound 32A was synthesized by subjecting 3,4-dihydronaphthalene-2-carboxylate to Method A with the following modifications. The aqueous phase was extracted with EtOAc subsequent to neutralization. The combined organic extracts were dried with Na$_2$SO$_4$, filtered, and concentrated under reduced pressure. The resulting residue was purified by preparatory HPLC to afford the desired compound (0.008 g, 40% yield).

$^1$H NMR (300 MHz, CD$_3$OD) δ 7.26-7.10 (m, 5H), 2.86 (t, 2H, J=8.2 Hz), 2.50 (t, 2H, J=8.2 Hz); HPLC purity (UV/Vis)=86%. ESI+MS: m/z 190.1 ([M+H]$^+$).

Example 10

N-Hydroxy-3-Methyl-1H-Indene-2-Carboxamide (29A)

Method G:

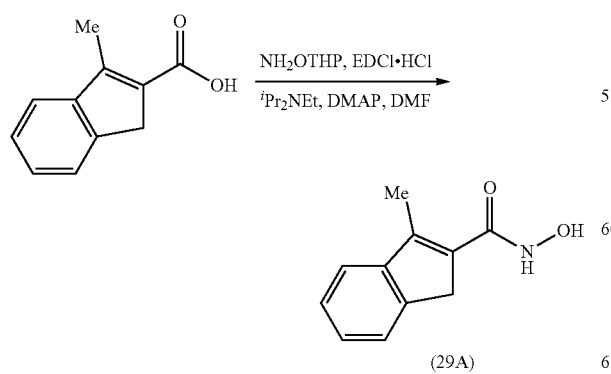

To a solution of 3-methyl-1H-indene-2-carboxylic acid (0.100 g, 0.570 mmol), O-(tetrahydro-2H-pyran-2-yl)hydroxylamine (0.202 g, 1.72 mmol, 3.00 equiv), 4-dimethylaminopyridine (0.014 g, 0.11 mmol, 0.20 equiv), $^i$Pr$_2$NEt (0.60 mL, 3.4 mmol, 6.0 equiv) in 2.0 mL of DMF was added EDCI.HCl (0.220 g, 1.15 mmol, 2.00 equiv). The reaction was stirred overnight at room temperature, diluted in EtOAc, washed with 1N HCl, and then washed with brine. The organic phase was dried over MgSO$_4$, filtered, and concentrated under reduced pressure. The resulting residue was redissolved in MeOH and p-toluenesulfonic acid monohydrate (0.110 g, 0.570 mmol, 1 equiv) was added. The reaction mixture was stirred at room temperature for 1 h and concentrated under reduce pressure. The product was obtained upon purification using preparatory HPLC (0.013 g, 12% yield).

$^1$H NMR (300 MHz, CD$_3$OD) δ 7.49-7.44 (m, 2H), 7.37-7.26 (m, 2H), 3.59-3.55 (m, 2H), 2.45 (t, 3H, J=2.3 Hz); HPLC purity (UV/Vis)>99.0%; ESI+MS: m/z 189.9 ([M]$^+$).

Example 11

N-Hydroxy-1-Tosyl-1,2,3,6-Tetrahydropyridine-4-Carboxamide (31A)

Method H:

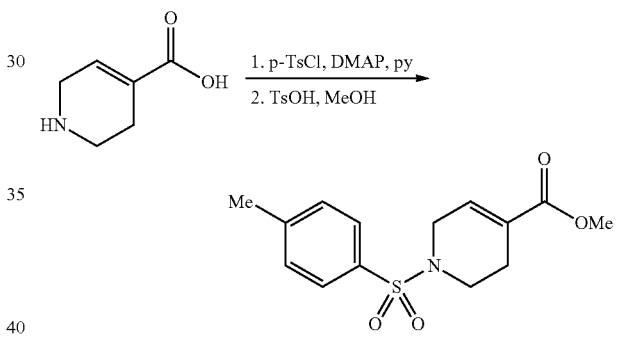

To a solution of N-hydroxy-1,2,3,6-tetrahydropyridine-4-carboxamide hydrochloride (0.10 g, 0.61 mmol) and 4-dimethylaminopyridine (0.007 g, 0.06 mmol, 0.1 equiv) in 2 mL of pyridine was added p-tosyl chloride (0.128 g, 0.67 mmol, 1.1 equiv). The reaction was stirred at room temperature for 2 h, diluted in EtOAc, and washed with 1M HCl$_{(aq)}$. The organic phase was concentrated under reduced pressure, and the resulting residue was redissolved in 2 mL of MeOH. Next, p-toluenesulfonic acid monohydrate (0.01 g, 0.05 mmol, 0.08 equiv) was added, and the reaction mixture was stirred and heated to 50° C. overnight. Concentration under reduced pressure followed by purification using flash chromatography afforded methyl 1-tosyl-1,2,3,6-tetrahydropyridine-4-carboxylate (0.055 g, 30.5% yield).

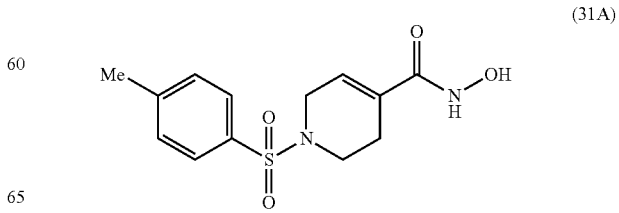

(31A)

Compound 31A was synthesized by subjecting methyl 1-tosyl-1,2,3,6-tetrahydropyridine-4-carboxylate to Method A with the following modifications. The resulting residue was purified by preparatory HPLC to afford the desired compound (0.043 g, 78% yield).

$^1$H NMR (300 MHz, CD$_3$OD) δ 7.69 (d, 2H, J=8.0 Hz), 7.42 (d, 2H, J=8.0 Hz), 6.40 (br s, 1H), 3.69 (br s, 2H), 3.17 (t, 2H, J=5.1 Hz), 2.43 (s, 3H), 2.41-2.32 (m, 2H); HPLC purity (UV/Vis)>99.0%. ESI+MS: m/z 296.5 ([M+H]$^+$)

Example 12

N-Hydroxy-1-(4-Methoxybenzoyl)-1,2,3,6-Tetrahydropyridine-4-Carboxamide (14A)

Method I:

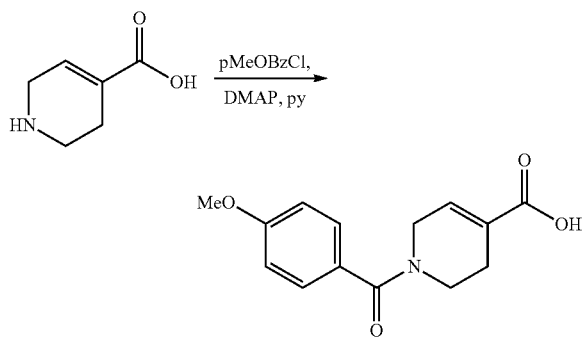

To a solution of N-hydroxy-1,2,3,6-tetrahydropyridine-4-carboxamide hydrochloride (0.321 g, 1.96 mmol) and 4-dimethylaminopyridine (0.024 g, 0.20 mmol, 0.10 equiv) in 6.5 mL of pyridine was added p-methoxybenzoyl chloride (0.260 mL, 1.96 mmol, 1.00 equiv) dropwise. The reaction mixture was stirred at room temperature for 3 h, diluted with EtOAc then washed with 1M HCl$_{(aq)}$. The organic phase was dried over Na$_2$SO$_4$, filtered, and concentrated under reduced pressure. The resulting residue was purified using flash chromatography to afford methyl 1-(4-methoxybenzoyl)-1,2,3,6-tetrahydropyridine-4-carboxylate (0.116 g, 23% yield).

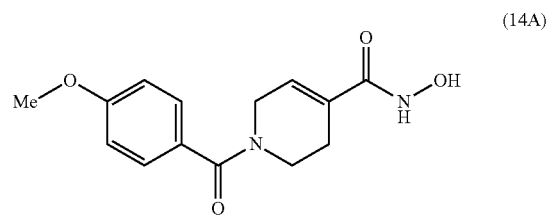 [SMILES: COc1ccc(C(=O)N2CC=C(C(=O)NO)CC2)cc1]

(14A)

Compound 14A was synthesized by subjecting the corresponding carboxylic acid (synthesized by Method I) to Method G (0.002 g, 1% yield).

$^1$H NMR (300 MHz, D$_2$O) δ 7.40 (d, 2H, J=8.7 Hz), 7.03 (d, 2H, J=8.7 Hz), 6.56 (br s, 1H), 4.29 (br s, 1H), 4.15 (br s, 1H), 3.85 (s, 3H), 3.79-3.73 (m, 1H), 3.55-3.47 (m, 1H), 2.43-2.27 (m, 2H); ESI+MS: m/z 277.2 ([M+H]$^+$).

Example 13

Inhibition of Histone Deacetylase Enzymatic Activity

The following microfluidic lab-on-a-chip assay as described herein was used to assay the compounds of the invention. See; Holson, E. et al., WO201214950 (A1)—Inhibitors of Histone Deacetylases.

All HDACs were purchased from BPS Bioscience. All other reagents were purchased from Sigma. Caliper EZ reader II system was used to collect all the data.

In short, purified HDACs were incubated with 2 μM carboxyfluorescein (FAM)-labeled acetylated peptide substrate and test compound for 60 min at room temperature, in HDAC assay buffer that contained 50 mM HEPES (pH 7.4), 100 mM KCl, 0.01% BSA and 0.001% Tween-20. Reactions were terminated by the addition of the known pan HDAC inhibitor LBH-589 (panobinostat) with a final concentration of 1.5 μM. Substrate and product were separated electrophoretically and fluorescence intensity in the substrate and product peaks was determined and analyzed by Labchip EZ Reader. The reactions were performed in duplicate for each sample. IC$_{50}$ values were automatically calculated by Origion8 using 4 Parameter Logistic Model. The percent inhibition was plotted against the compound concentration, and the IC50 value was determined from the logistic dose-response curve fitting by Origin 8.0 software. (Madan Katragadda, Paola Magotti, Georgia Sfyroera, and John D. Lambris, *J. Med. Chem.* 2006, 49, 4616-4622).

The compounds of the invention were assayed for histone deacetylase inhibitory activity. The data is presented in Table 2 below. It will be recognized by one skilled in the art that the compounds can be assessed against other histone deacetylase enzymes and that the presentation of data is illustrative and in no way intended to limit the scope of the present invention. The compounds of the invention can be assayed against a range of histone deacetylase enzymes depending upon the performance activity desired to be gathered.

TABLE 2

| | HDAC Isoform Inhibition IC$_{50}$ (μM) | | | | | | | | |
|---|---|---|---|---|---|---|---|---|---|
| Compound | 1 | 2 | 3 | 4 | 5 | 6 | 7 | 8 | 9 |
| 21A | 0.727 | 3.439 | 0.734 | 29.673 | 21.138 | 0.024 | 9.967 | 1.851 | >33 |
| 32A | 1.864 | 2.597 | 2.323 | 4.645 | 14.045 | 0.014 | 2.460 | 0.626 | 4.083 |
| 29A | 0.275 | 0.584 | 0.713 | 15.976 | 23.632 | 0.049 | 17.942 | 1.128 | 11.165 |
| 22A | >33 | >33 | >33 | >33 | >33 | >33 | >33 | 9.142 | >33 |
| 31A | 0.084 | 0.375 | 0.099 | 14.814 | 7.412 | 0.014 | 11.607 | 0.494 | 12.977 |
| 30A | >33 | >33 | >33 | >33 | >33 | >33 | >33 | 2.632 | >33 |
| 12A | >33 | >33 | >33 | >33 | >33 | 6.197 | >33 | 23.201 | >33 |

TABLE 2-continued

| Compound | HDAC Isoform Inhibition IC$_{50}$ (µM) | | | | | | | | |
| --- | --- | --- | --- | --- | --- | --- | --- | --- | --- |
| | 1 | 2 | 3 | 4 | 5 | 6 | 7 | 8 | 9 |
| 7A | >33 | >33 | >33 | >33 | >33 | 2.677 | >33 | 2.159 | >33 |
| 10A | 2.095 | 1.705 | 3.222 | 7.933 | 10.858 | 0.106 | 6.914 | 0.055 | 15.971 |
| 20A | 1.077 | 1.898 | 1.396 | >33 | 52.583 | 0.016 | 26.845 | 1.380 | >33 |
| 19A | 0.423 | 1.400 | 0.493 | 10.137 | 15.210 | 0.011 | 2.320 | 0.523 | 11.709 |

The standardized protocol for running the HDAC selectivity panel on Caliper LabChip EZ-Reader Instrument is found in Holson, E. et al., WO201214950 (A1), Example 15.

Example 14

Detection of Acetylated α-Tubulin (Ac-Tubulin) and Acetyl Histone H3 (Ac-H3) in HeLa Cells HeLa cells were treated with compounds for 24 h, at which time lysates were collected using RIPA buffer with added protease (Roche) and phosphatase (Roche) inhibitors. Electrophoresis was performed using NuPage 4-12% Bis-Tris gels (Invitrogen). Proteins were transferred to a nitrocellulose membrane and probed using antibodies for Ac-tubulin (Sigma-Aldrich), Ac-H3 (Millipore) and GAPDH (Cell Signalling). Chemiluminescence was induced by subsequent incubation with HRP-linked secondary antibodies (GE Healthcare UK Ltd.) and treatment of the membrane with the appropriate ECL solutions (Thermo Scientific). Visualization was accomplished using a Gel Logic 4000 Pro (Carestream), and the raw data files were converted to jpegs using ImageJ (NIH). The results are shown in FIG. 1.

What is claimed:
1. A compound of formula I:

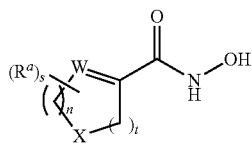

(I)

or a pharmaceutically acceptable salt or tautomer thereof, wherein
n is 0, 1, 2, 3, 4, or 5;
t is 1, 2, 3, 4, or 5;
s is 0, 1, 2, 3, 4, 5, 6, 7 or 8;
X is $CR^bR^c$, $NR^d$, or $S(O)_z$;
W is $CR^e$ or N;
$R^e$ is hydrogen, OH, $C_1$-$C_4$ alkyl, or halogen;
z is 0, 1, or 2;
each $R^a$ is independently selected from halogen, CN, $CF_3$, $OR^f$, $OCF_3$, $C(O)R^g$, $C_1$-$C_8$ alkoxyl, $NR^hR^i$, $C_2$-$C_8$ alkyl, $C_2$-$C_8$ alkenyl, $C_2$-$C_8$ alkynyl, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring, $(CH_2)_k$-6 to 10-membered aromatic ring, and $(CH_2)_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more $R^1$, provided that when X is $CH_2$, W is CH, and n+t is 3, s is not 0;

each $R^b$, $R^c$, and $R^d$ is independently selected from hydrogen, halogen, CN, $CF_3$, $OR^f$, $OCF_3$, $C(O)R^g$, $C_1$-$C_8$ alkoxyl, $NR^hR^i$, $S(O)_zR^j$, $C_1$-$C_8$ alkyl, $C_2$-$C_8$ alkenyl, $C_2$-$C_8$ alkynyl, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring, $(CH_2)_k$ -6 to 10-membered aromatic ring, and $(CH_2)_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more $R^1$;
or $R^e$ is attached to $R^a$ to form a fused ring, wherein said ring is selected from $C_3$-$C_8$ cycloalkyl, $C_4$-$C_8$ cycloalkenyl, 3 to 10-membered saturated or unsaturated heterocyclic ring, 6 to 10-membered aromatic ring, and 3 to 10-membered heteroaromatic ring, wherein said fused ring is unsubstituted or substituted with one or more $R^2$;
or taken together two $R^a$ are attached to form a fused ring, wherein said ring is selected from $C_3$-$C_8$ cycloalkyl, $C_4$-$C_8$ cycloalkenyl, 3 to 10-membered saturated or unsaturated heterocyclic ring, 6 to 10-membered aromatic ring, and 3 to 10-membered heteroaromatic ring, wherein said fused ring is unsubstituted or substituted with one or more $R^2$;
or one $R^b$, $R^c$, or $R^d$ is attached to $R^e$ or $R^a$ to form a fused ring, wherein said ring is selected from $C_3$-$C_8$ cycloalkyl, $C_4$-$C_8$ cycloalkenyl, 3 to 10-membered saturated or unsaturated heterocyclic ring, 6 to 10-membered aromatic ring, and 3 to 10-membered heteroaromatic ring, wherein said fused ring is unsubstituted or substituted with one or more $R^2$;
or taken together two $R^a$ are attached to form a bridged ring;
or $R^a$ is attached to one $R^b$, $R^c$, or $R^d$ to form a bridged ring;
or $R^b$ and $R^c$ taken together with the carbon atom to which they are attached form C=O;
or two $R^a$ taken together with the carbon atom to which they are attached form a spirocyclic ring selected from a $C_3$-$C_8$ cycloalkyl, $C_4$-$C_8$ cycloalkenyl, or 3 to 10-membered saturated or unsaturated heterocyclic ring, wherein said spirocyclic ring is unsubstituted or substituted with one or more $R^2$, provided that when n is 2, t is 0, W is CH, and X is O or S, said fused ring is not unsubstituted phenyl;
or $R^b$ and $R^c$ taken together with the carbon atom to which they are attached form a spirocyclic ring selected from a $C_3$-$C_8$ cycloalkyl, $C_4$-$C_8$ cycloalkenyl, or 3 to 10-membered saturated or unsaturated heterocyclic ring, wherein said spirocyclic ring is unsubstituted or substituted with one or more $R^2$;
each $R^g$ is selected from hydrogen, $OR^L$, $NR^mR^o$, $CF_3$, $C_1$-$C_8$ alkyl, $C_2$-$C_8$ alkenyl, $C_2$-$C_8$ alkynyl, $(CH_2)_k$—$C_3$-$C_8$ cycloalkyl, $(CH_2)_k$—$C_4$-$C_8$ cycloalkenyl, $(CH_2)_k$ -3 to 10-membered saturated or unsaturated heterocyclic ring, $(CH_2)_k$-6 to 10-membered aromatic ring, and $(CH_2)_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more $R^3$;

each $R^f$, $R^i$, $R^j$, $R^L$, $R^m$, and $R^o$ is independently selected from hydrogen, $C_1$-$C_8$ alkyl, $C_2$-$C_8$ alkenyl, $C_2$-$C_8$ alkynyl, $C(O)R^p$, $S(O)_zR^{jj}$, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring, $(CH_2)_k$ -6 to 10-membered aromatic ring, and $(CH_2)_k$-3 to 10-membered heteroaromatic ring, wherein said alkyl, alkenyl, alkynyl; cycloalkyl, cycloalkenyl, heterocyclic ring, aromatic ring; and heteroaromatic ring are unsubstituted or substituted with one or more $R^4$;

$R^h$ is selected from $C_1$-$C_8$ alkyl; $C_2$-$C_8$ alkenyl, $C_2$-$C_8$ alkynyl, $C(O)R^p$, $S(O)_zR^{jj}$, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring, $(CH_2)_k$ -6 to 10-membered aromatic ring, and $(CH_2)_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more $R^4$;

each $R^p$ and $R^{jj}$ is independently selected from $OR^q$; $NR^rR^u$, $CF_3$, $C_1$-$C_8$ alkyl, $C_2$-$C_8$ alkenyl, $C_2$-$C_8$ alkynyl, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring, $(CH_2)_k$-6 to 10-membered aromatic ring, and $(CH_2)_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more $R^5$;

each $R^q$, $R^r$, and $R^u$ is independently selected from hydrogen, $C_1$-$C_8$ alkyl, $C_2$-$C_8$ alkenyl, $C_2$-$C_8$ alkynyl, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring, $(CH_2)_k$-6 to 10-membered aromatic ring, and $(CH_2)k$-3 to 10-membered heteroaromatic ring; wherein said alkyl; alkenyl, alkynyl, cycloalkyl, cycloalkenyl, heterocyclic ring, aromatic ring, and heteroaromatic ring are unsubstituted or substituted with one or more $R^6$;

each $R^3$, $R^4$, $R^5$, and $R^6$ is independently selected from halogen, $CF_3$, $OCF_3$, $C_1$-$C_8$ alkyl, $C_2$-$C_8$ alkenyl, $C_2$-$C_8$ alkynyl, $OC_1$-$C_8$ alkyl, $NH_2$, $NHC_1$-$C_8$ alkyl, $N(C_1$-$C_8$ alkyl$)_2$, $C(O)NR^vR^y$, $C(O)R^{aa}$, and $C(O)OR^{bb}$, and $(CH_2)_k$-6 to 10-membered aromatic ring, wherein said aromatic ring is unsubstituted or substituted with one or more $R^7$;

$R^1$ is selected from halogen, $CF_3$, $OCF_3$, $C_1$-$C_8$ alkyl, $C_2$-$C_8$ alkenyl, $C_2$-$C_8$ alkynyl, $OC_1$-$C_8$ alkyl, $NHC_1$-$C_8$ alkyl, $N(C_1$-$C_8$ alkyl$)_2$, $C(O)NR^vR^y$, $C(O)R^{aa}$, and $C(O)OR^{bb}$, and $(CH_2)_k$-6 to 10-membered aromatic ling, wherein said aromatic ring is unsubstituted or substituted with one or more $R^7$;

$R^2$ is selected from $CF_3$, $OCF_3$, $C_1$-$C_8$ alkyl, $C_2$-$C_8$ alkenyl, $C_2$-$C_8$ alkynyl, $NH_2$, $NHC_1$-$C_8$ alkyl, $N(C_1$-$C_8$ alkyl$)_2$, $C(O)NR^vR^y$, $C(O)R^{aa}$, and $C(O)OR^{bb}$, and $(CH_2)_k$-6 to 10-membered aromatic ring, wherein said aromatic ring is unsubstituted or substituted with one or more $R^7$;

each $R^v$, $R^y$, $R^{aa}$, and $R^{bb}$ is independently selected from hydrogen, $C_1$-$C_8$ alkyl, $C_2$-$C_8$ alkenyl, $C_2$-$C_8$ alkynyl, $(CH_2)_k$—$C_3$-$C_8$ cycloalkyl $(CH_2)_k$—$C_4$-$C_8$ cycloalkenyl, $(CH_2)_k$-3 to 10-membered saturated or unsaturated heterocyclic ring, $(CH_2)_k$-6 to 10-membered aromatic ring, and $(CH_2)_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more $R^7$;

each $R^7$ is selected from halogen, $CF_3$, $OCF_3$, $C_1$-$C_8$ alkyl, $C_2$-$C_8$ alkenyl, $C_2$-$C_8$ alkynyl, $OC_1$-$C_8$ alkyl, $NH_2$, $NHC_1$-$C_8$ alkyl, and $N(C_1$-$C_8$ alkyl$)_2$; and k is 0, 1, 2; or 3.

2. The compound of claim 1, or a pharmaceutically acceptable salt or tautomer thereof, wherein:

X is $CR^bR^c$; and

W is $CR^e$.

3. The compound of claim 2, or a pharmaceutically acceptable salt or tautomer thereof, wherein n is 0, 1, or 2, and t is 1, 2, or 3.

4. The compound of claim 2, wherein the compound is of formula II:

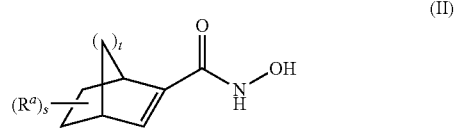

(II)

or a pharmaceutically acceptable salt or tautomer thereof, wherein t is 1 or 2.

5. The compound of claim 2, wherein the compound is of formula Va, Vb, or Vc:

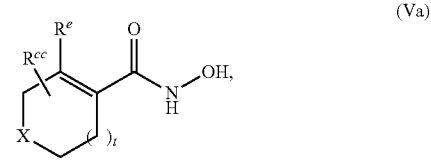

(Va)

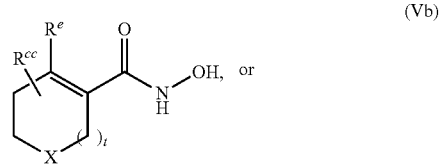

(Vb)

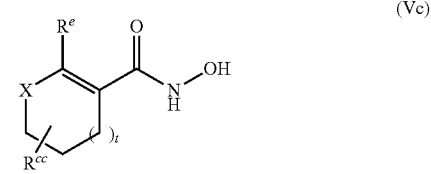

(Vc)

or a pharmaceutically acceptable salt or tautomer thereof wherein $R^{cc}$ is selected from hydrogen, halogen, CN, $CF_3$, $OR^f$, $OCF_3$, $C(O)R^g$, $C_1$-$C_8$ alkoxyl, $NR^hR^i$ $C_2$-$C_8$ alkyl, $C_2$-$C_8$ alkenyl, $C_2$-$C_8$ alkynyl, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring, $(CH_2)_k$-6 to 10-membered aromatic ring, and $(CH_2)_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more $R^1$, provided that when X is $CH_2$ and t is 1, $R^{cc}$ is not hydrogen; and t is 1 or 2;

or $R^{cc}$ is attached to one of $R^b$, $R^c$, or $R^d$ is to form a bridged ring;

or one of $R^b$, $R^c$, or $R^d$ is attached to $R^e$ to form a fused ring, wherein said ring is selected from $C_3$-$C_8$ cycloalkyl, $C_4$-$C_8$ cycloalkenyl, 3 to 10-membered saturated or unsaturated heterocyclic ring, 6 to 10-membered aromatic ring, and 3 to 10-membered heteroaromatic ring, further wherein said fused ring is unsubstituted or substituted with one or more $R^2$;

or $R^{cc}$ is attached to $R^e$ to form a fused ring, wherein said ring is selected from $C_3$-$C_8$ cycloalkyl, $C_4$-$C_8$ cycloalkenyl, 3 to 10-membered saturated or unsaturated heterocyclic ring, 6 to 10-membered aromatic ring, and 3 to 10-membered heteroaromatic ring, further wherein said fused ring is unsubstituted or substituted with one or more $R^2$;

or one of $R^b$, $R^c$, or $R^d$ is attached to $R^{cc}$ form a fused ring, wherein said ring is selected from $C_3$-$C_8$ cycloalkyl, $C_4$-$C_8$ cycloalkenyl, 3 to 10-membered saturated or unsaturated heterocyclic ring, 6 to 10-membered aromatic ring, and 3 to 10-membered heteroaromatic ring, further wherein said fused ring is unsubstituted or substituted with one or more $R^2$;

or $R^b$ and $R^c$ taken together with the carbon atom to which they are attached form a spirocyclic ring selected from $C_3$-$C_8$ cycloalkyl, $C_4$-$C_3$ cycloalkenyl, or 3 to 10-membered saturated or unsaturated heterocyclic ring, wherein said spirocyclic ring is unsubstituted or substituted with one or more $R^2$;

or $R^b$ and $R^c$ taken together with the carbon atom to which they are attached form C=O.

6. The compound of claim 2, wherein the compound is of formula VI:

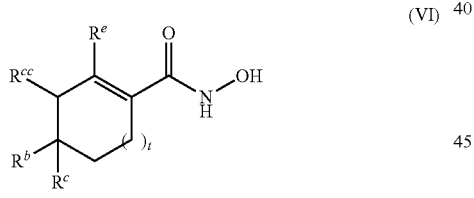

(VI)

or a pharmaceutically acceptable salt or tautomer thereof wherein $R^{cc}$ is selected from hydrogen, halogen, CN, $CF_3$, $OR^f$, $OCF_3$, $C(O)R^g$, $C_1$-$C_8$ alkoxyl, $NR^hR^i$ $C_2$-$C_8$ alkyl, $C_2$-$C_8$ alkenyl, $C_2$-$C_8$ alkynyl, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring, $(CH_2)_k$-6 to 10-membered aromatic ring, and $(CH_2)_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more $R^1$; and t is 1 or 2, provided that when t is 1, at least one of $R^b$, $R^c$, and $R^{cc}$ is not hydrogen;

or one of $R^b$ or $R^c$ is attached to $R^{cc}$ to form a fused ring, wherein said ring is selected from $C_3$-$C_8$ cycloalkyl, $C_4$-$C_8$ cycloalkenyl, 3 to 10-membered saturated or unsaturated heterocyclic ring, 6 to 10-membered aromatic ring, and 3 to 10-membered heteroaromatic ring, further wherein said fused ring is unsubstituted or substituted with one or more $R^2$;

or $R^{cc}$ is attached to $R^e$ to form a fused ring, wherein said ring is selected from $C_3$-$C_8$ cycloalkyl, $C_4$-$C_8$ cycloalkenyl, 3 to 10-membered saturated or unsaturated heterocyclic ring, 6 to 10-membered aromatic ring, and 3 to 10-membered heteroaromatic ring, further wherein said fused ring is unsubstituted or substituted with one or more $R^2$;

or $R^b$ and $R^c$ taken together with the carbon atom to which they are attached to form a spirocyclic ring selected from $C_3$-$C_8$ cycloalkyl, $C_4$-$C_8$ cycloalkenyl, or 3 to 10-membered saturated or unsaturated heterocyclic ring, wherein said spirocyclic ring is unsubstituted or substituted with one or more $R^2$;

or $R^b$ and $R^c$ taken together with the carbon atom to which they are attached form C=O.

7. The compound of claim 5, or a pharmaceutically acceptable salt or tautomer thereof, wherein:

one of $R^b$ or $R^c$ is attached to $R^{cc}$ to form a fused ring; or $R^{cc}$ is attached to $R^e$ to form a fused ring.

8. The compound of claim 6, or a pharmaceutically acceptable salt or tautomer thereof, wherein:

one of $R^b$ or $R^c$ is attached to $R^{cc}$ to form a fused ring; or $R^{cc}$ is attached to $R^e$ to form a fused ring.

9. The compound of claim 6, or a pharmaceutically acceptable salt or tautomer thereof, wherein $R^b$ and $R^c$ taken together with the carbon atom to which they are attached form a spirocyclic ring.

10. The compound of claim 1 of formula VIIa or VIIb:

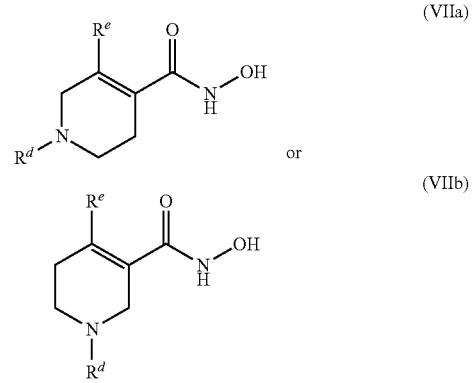

or a pharmaceutically acceptable salt or tautomer thereof.

11. The compound of claim 1, wherein the compound is of the formula:

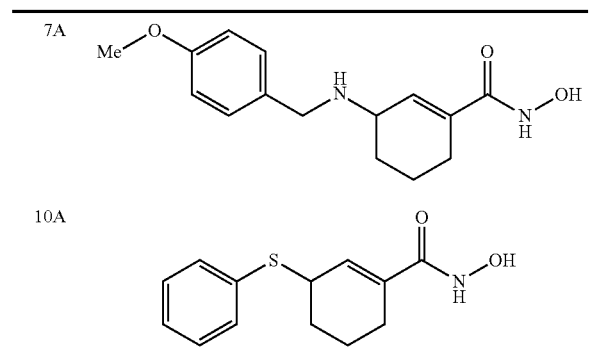

-continued

14A
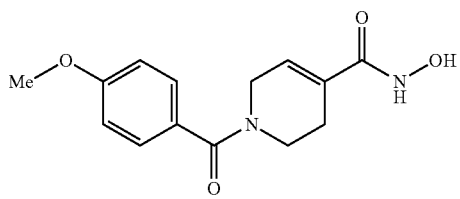 [SMILES: COc1ccc(C(=O)N2CC=C(C(=O)NO)CC2)cc1]

21A
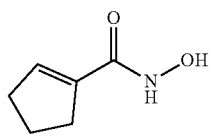

22A
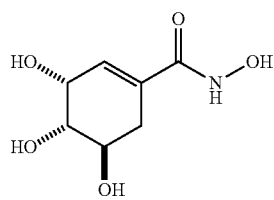 [SMILES: O=C(NO)C1=C[C@@H](O)[C@@H](O)[C@H](O)C1]

29A
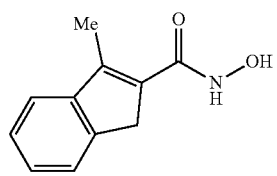 [SMILES: CC1=C(C(=O)NO)Cc2ccccc21]

30A
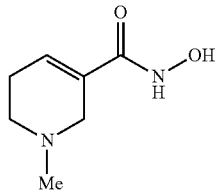 [SMILES: CN1CCC=C(C(=O)NO)C1]

31A
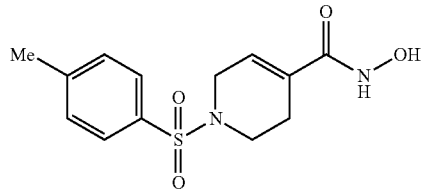 [SMILES: Cc1ccc(S(=O)(=O)N2CC=C(C(=O)NO)CC2)cc1]

32A
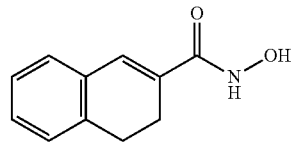 [SMILES: O=C(NO)C1=Cc2ccccc2CC1]

33A
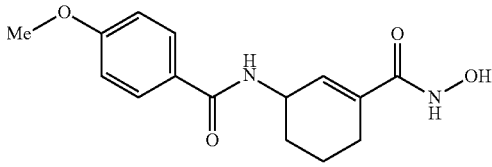 [SMILES: COc1ccc(C(=O)NC2C=C(C(=O)NO)CCC2)cc1]

or a pharmaceutically acceptable salt or tautomer thereof.

12. A pharmaceutical composition comprising an effective amount of a compound of claim 1, or a pharmaceutically acceptable salt or tautomer thereof and a pharmaceutical carrier, diluent, or excipient.

13. A kit containing one or more compounds of claim 1, or a pharmaceutically acceptable salt or tautomer thereof.

14. The compound of claim 1, or a pharmaceutically acceptable salt or tautomer thereof, wherein W is $CR^e$.

15. The compound of claim 1, or a pharmaceutically acceptable salt or tautomer thereof, wherein W is N.

16. The compound of claim 2, or a pharmaceutically acceptable salt or tautomer thereof, wherein:
n is 0, and t is 2;
n is 1, and t is 1;
n is 1 and t is 2; or
n is 2 and t is 1.

17. The compound of claim 2, or a pharmaceutically acceptable salt or tautomer thereof, wherein:
$R^e$ is hydrogen, OH, $C_1$-$C_4$ alkyl, or halogen;
each $R^a$ is independently selected from halogen, CN, $CF_3$, $OR^f$, $OCF_3$, $C(O)R^g$, $C_1$-$C_8$ alkoxyl, $NR^hR^i$, $C_2$-$C_8$ alkyl, $C_2$-$C_8$ alkenyl, $C_2$-$C_8$ alkynyl, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring; $(CH_2)_k$-6 to 10-membered aromatic ring, and $(CH_2)k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more $R^1$; provided that when X is $CH_2$, W is CH, and n+t is 3, s is not 0; and
each $R^b$ and $R^c$ is independently selected from hydrogen, halogen, CN, $CF_3$, $OR^f$, $OCF_3$, $C(O)R^g$, $C_1$-$C_8$ alkoxyl, $NR^hR^i$, $S(O)_zR^j$, $C_1$-$C_8$ alkyl, $C_2$-$C_8$ alkenyl, $C_2$-$C_8$ alkynyl, $(CH_2)_k$—$C_3$-$C_8$ cycloalkyl, $(CH_2)_k$—$C_4$-$C_8$ cycloalkenyl, $(CH_2)_k$-3 to 10-membered saturated or unsaturated heterocyclic ring, $(CH_2)_k$-6 to 10-membered aromatic ring, and $(CH_2)_k$-3 to 10-membered heteroaromatic ring, wherein said alkyl, alkenyl, alkynyl, cycloalkyl, cycloalkenyl, heterocyclic ring, aromatic ring and heteroaromatic ring are unsubstituted or substituted with one or more $R^1$;
or $R^b$ and $R^c$ taken together with the carbon atom to which they are attached form C=O.

18. The compound of claim 2, or a pharmaceutically acceptable salt or tautomer thereof, wherein:
$R^e$ is attached to $R^a$ to form a fused ring, wherein said ring is selected from $C_3$-$C_8$ cycloalkyl, $C_4$-$C_8$ cycloalkenyl, 3 to 10-membered saturated or unsaturated heterocyclic ring, 6 to 10-membered aromatic ring, and 3 to 10-membered heteroaromatic ring, wherein said fused ring is unsubstituted or substituted with one or more $R^2$;
or one $R^b$ or $R^c$ is attached to $R^e$ to form a fused ring, wherein said ring is selected from $C_3$-$C_8$ cycloalkyl, $C_4$-$C_8$ cycloalkenyl, 3 to 10-membered saturated or unsaturated heterocyclic ring, 6 to 10-membered aromatic ring, and 3 to 10-membered heteroaromatic ring, wherein said fused ring is unsubstituted or substituted with one or more $R^2$.

19. The compound of claim 2, or a pharmaceutically acceptable salt or tautomer thereof, wherein:
taken together two $R^a$ are attached to form a fused ring, wherein said ring is selected from $C_3$-$C_8$ cycloalkyl, $C_4$-$C_8$ cycloalkenyl, 3 to 10-membered saturated or unsaturated heterocyclic ring, 6 to 10-membered aromatic ring, and 3 to 10-membered heteroaromatic ring, wherein said fused ring is unsubstituted or substituted with one or more $R^2$;
or one $R^b$ or $R^c$ is attached to $R^a$ to form a fused ring, wherein said ring is selected from $C_3$-$C_8$ cycloalkyl, $C_4$-$C_8$ cycloalkenyl, 3 to 10-membered saturated or unsaturated heterocyclic ring, 6 to 10-membered aromatic ring, and 3 to 10-membered heteroaromatic ring, wherein said fused ring is unsubstituted or substituted with one or more $R^2$.
20. The compound of claim 2, wherein the compound is of the formula:
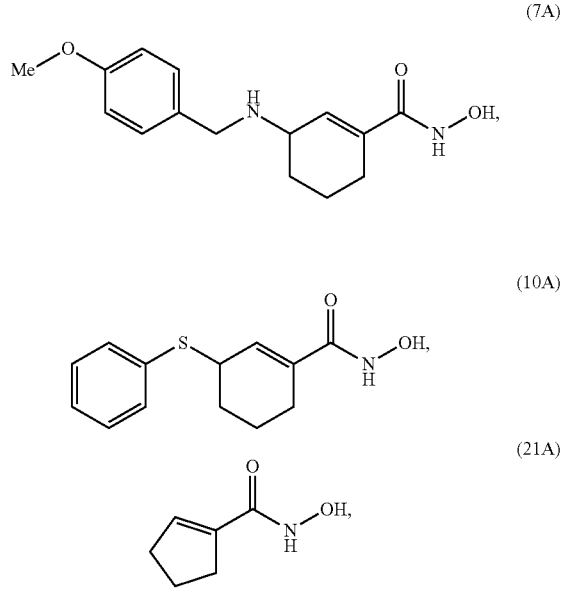
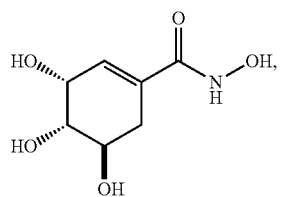
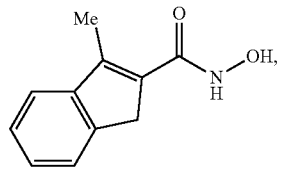
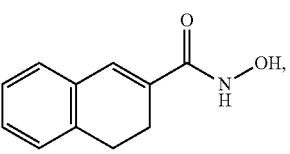
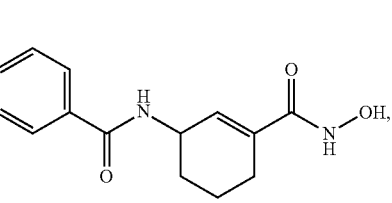
or a pharmaceutically acceptable salt or tautomer thereof.
* * * * *